United States Patent
Barrett et al.

(10) Patent No.: US 7,030,119 B1
(45) Date of Patent: *Apr. 18, 2006

(54) METHOD FOR TREATING CHRONIC PAIN USING MEK INHIBITORS

(75) Inventors: Stephen Douglas Barrett, Livonia, MI (US); Alexander James Bridges, Saline, MI (US); Haile Tecle, Ann Arbor, MI (US); Alistair Dixon, Cambridge (GB); Kevin Lee, Kenilworh (GB); Robert Pinnock, Cambridge (GB)

(73) Assignee: Warner-Lambert Company, Morris Plains, NJ (US)

( * ) Notice: Subject to any disclaimer, the term of this patent is extended or adjusted under 35 U.S.C. 154(b) by 192 days.

This patent is subject to a terminal disclaimer.

(21) Appl. No.: 10/031,037

(22) PCT Filed: Jul. 5, 2000

(86) PCT No.: PCT/US00/18345

§ 371 (c)(1),
(2), (4) Date: May 13, 2002

(87) PCT Pub. No.: WO01/05390

PCT Pub. Date: Jan. 25, 2001

Related U.S. Application Data

(60) Provisional application No. 60/144,418, filed on Jul. 16, 1999.

(51) Int. Cl.
*A61K 31/495* (2006.01)
*A61K 31/41* (2006.01)
*A61K 31/425* (2006.01)

(52) U.S. Cl. ............... 514/248; 514/359; 514/361; 514/362; 514/367

(58) Field of Classification Search ............... 514/248, 514/359, 361, 362, 367
See application file for complete search history.

(56) References Cited

U.S. PATENT DOCUMENTS 5,155,110 A 10/1992 Connor et al.
6,469,004 B1 * 10/2002 Barrett et al. ............... 514/248

FOREIGN PATENT DOCUMENTS

WO   WO 98/37881 A1   9/1998
WO   WO 00/35436 A2   6/2000
WO   WO 00/42022 A1   7/2000

OTHER PUBLICATIONS

Alessi, Dario R., et al., "PD 098059 Is a Specific Inhibitor of the Activation of Mitogen-activated Protein Kinase Kinase in Vitro and in Vivo", J. Biol. Chem., 1995, pp 27489-27494, vol. 270, No. 46.

(Continued)

*Primary Examiner*—San-Ming Hui
(74) *Attorney, Agent, or Firm*—Charles W. Ashbrook; Claude F. Purchase, Jr.; Pfizer, Inc.

(57) ABSTRACT

The invention features a method for treating chronic pain using a compound of formula (I).

28 Claims, 8 Drawing Sheets

OTHER PUBLICATIONS

Hwang, Daniel, et al., "Expression of Mitogen-Inducible Cyclooxygenase Induced by Lipopolysaccharide: Mediation through both mitogen-activated protein kinase and NF-KB signaling pathways in macrophages", Biochem Pharm, 1997, pp 87-96, vol. 54, Issue 1.

Larrivee, Jean-François, et al., "Role of the Mitogen-Activated Protein Kinases in the Expression of the Kinin B1 Receptors Induced by Tissue Injury ", J Immunol, 1998, pp 1419-1426, vol. 160, No. 3.

Polakiewicz, Roberto D., et al., "A Mitogen-activated Protein Kinase Pathway Is Required for µ-Opioid Receptor Desensitization", J. Biol. Chem., 1998, pp 12402-12406. vol. 273, No. 20.

PCT International Search Report PCT/US00/18345.

H. Bekemeier, et al., "Structure-Activity Relationship in Nonsteroidal Antiinflammatory Agents, Including Qsar in Fenamate Derivatives", Agents and Actions Supplements, Jul. 1, 1982, pp 17-34.

J. V. Duncia, et al., "MEK Inhibitors: The Chemistry and Biological Activity of U0126, Its Analogs, and Cyclization Products", Bioorganic & Medicinal Chemistry Letters, 1998, pp 2839-2844, No. 8.

N. S. Duesbery, et al., "MEK Waars, a new front in the Battle Against Cancer", Nature Medicine, Jul. 1999, pp 736-737, vol. 5, No. 7.

Ru-Rong Ji, et al., "Nociceptive-specific Activation of ERK in Spinal Neurons Contributes to Pain Hypersensitivity", Nature Neuroscience, Dec. 1999, pp 1114-1119, vol. 2, No. 12.

Office Action for 10/031,149 (A0000104-01-SMH) dated May 11, 2005.

* cited by examiner

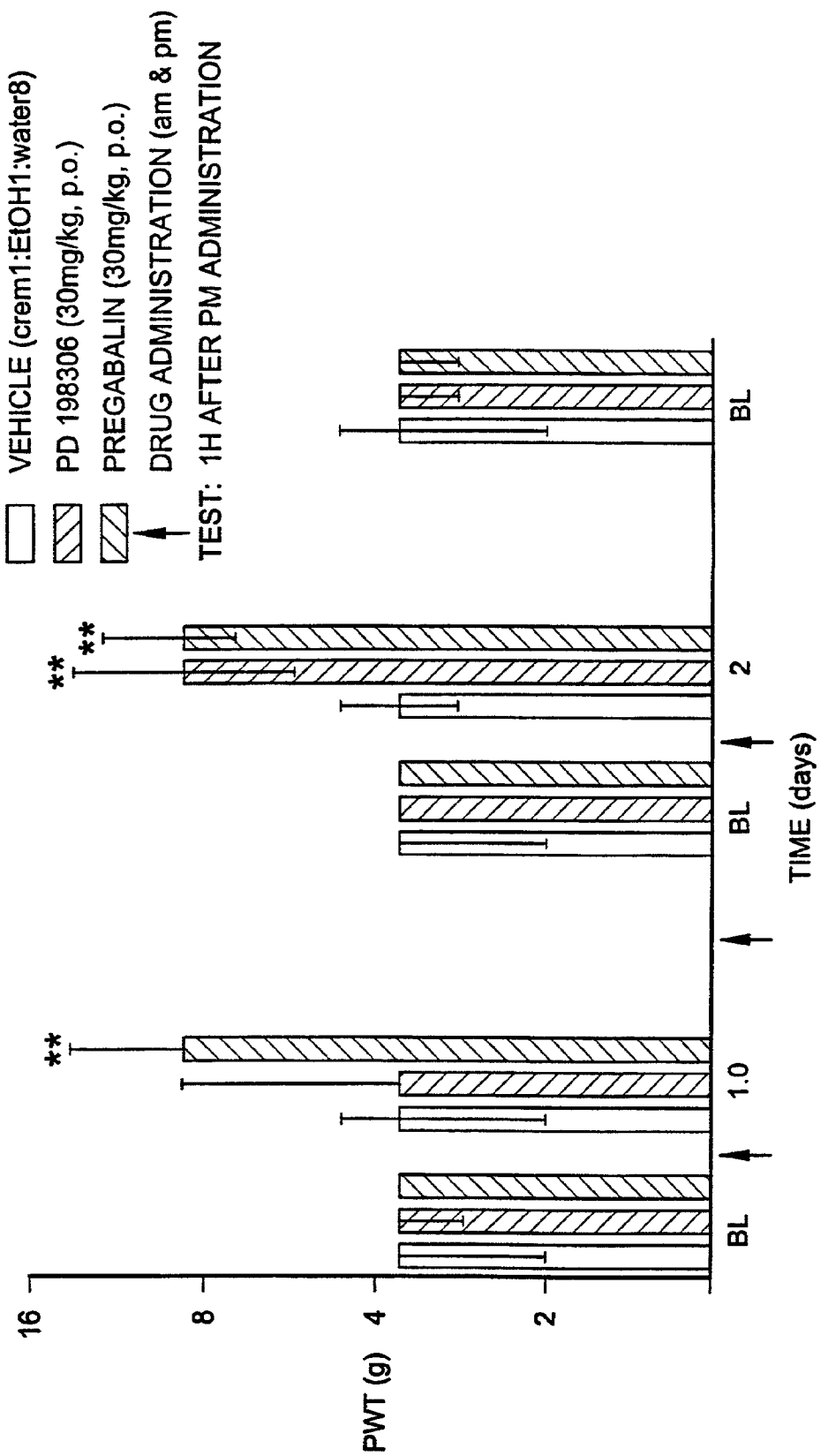

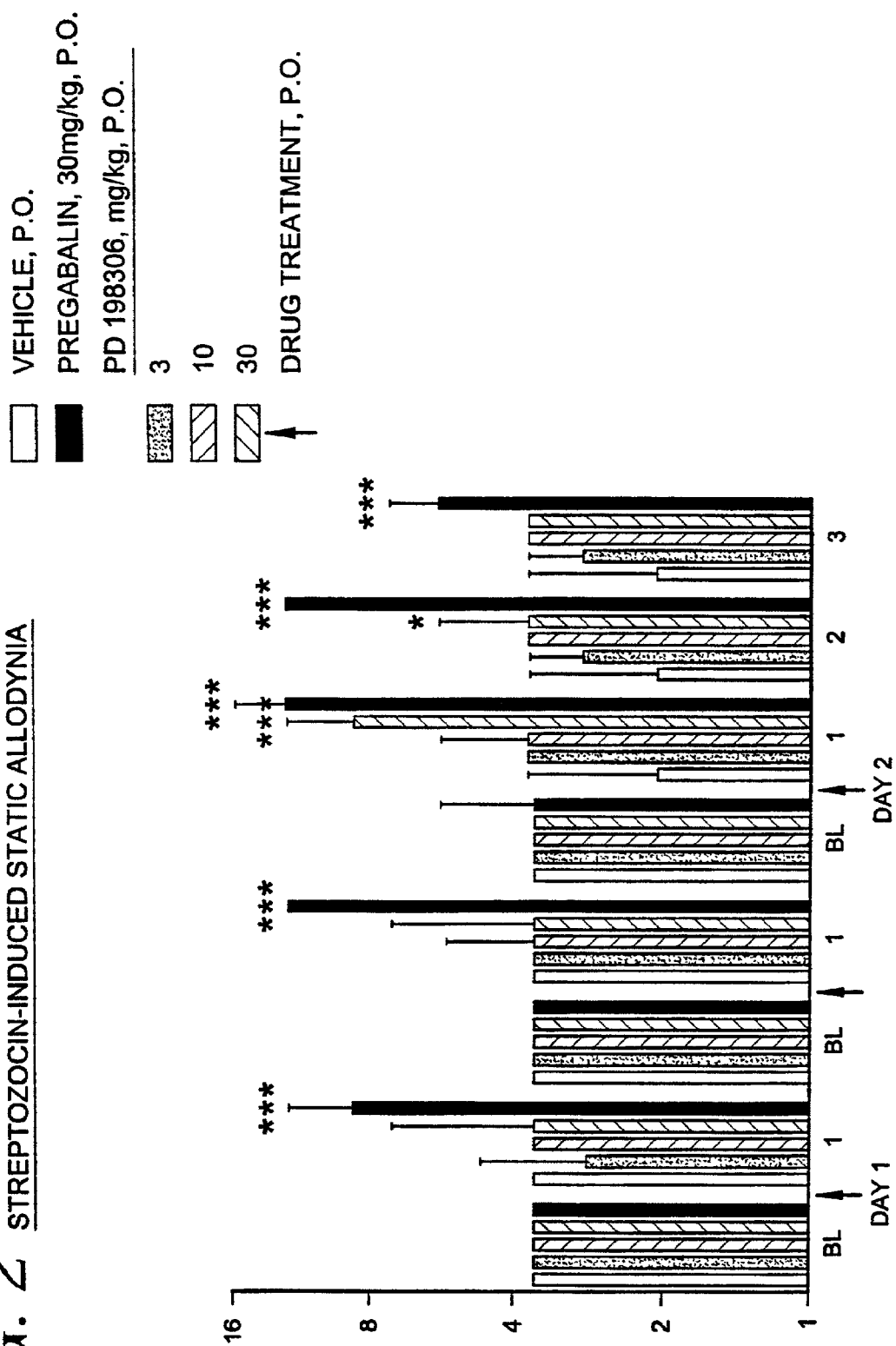

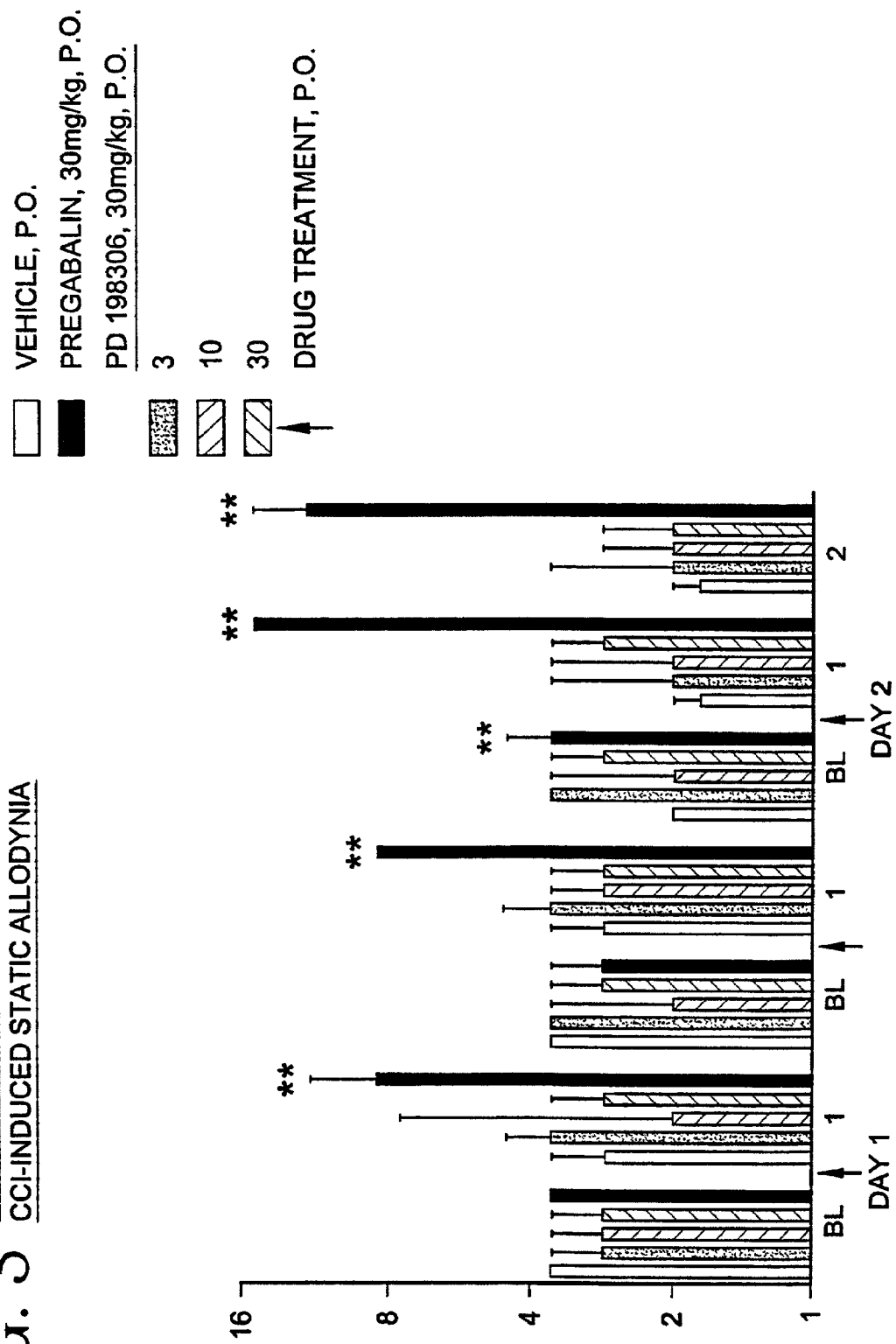
FIG. 3 EFFECT OF SYSTEMIC (p.o.) ADMINISTRATION OF PD 198306 ON CCI-INDUCED STATIC ALLODYNIA

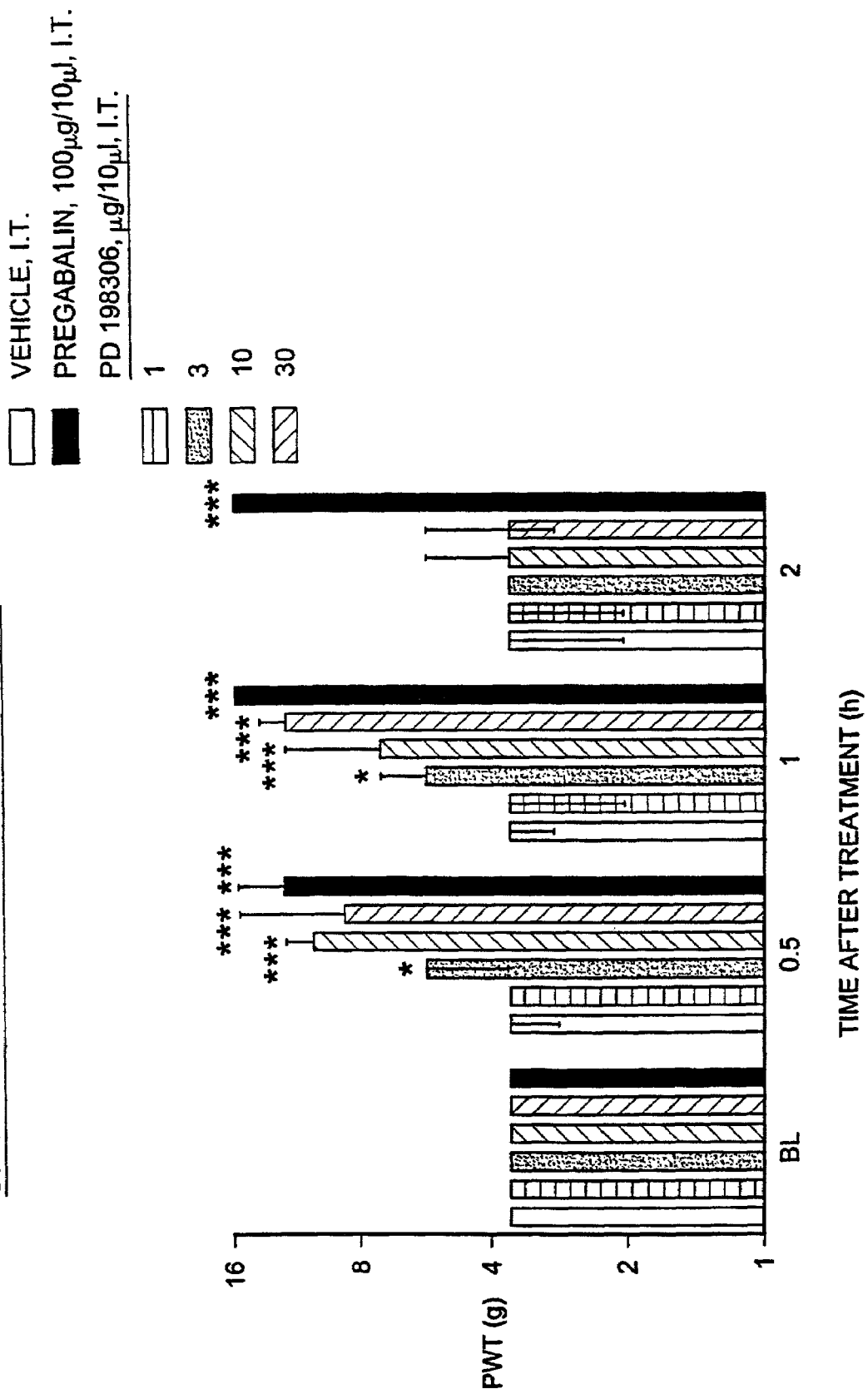
FIG. 4 EFFECT OF INTRATHECAL (i.t.) ADMINISTRATION OF PD 198306 ON STREPTOZOCIN-INDUCED STATIC ALLODYNIA

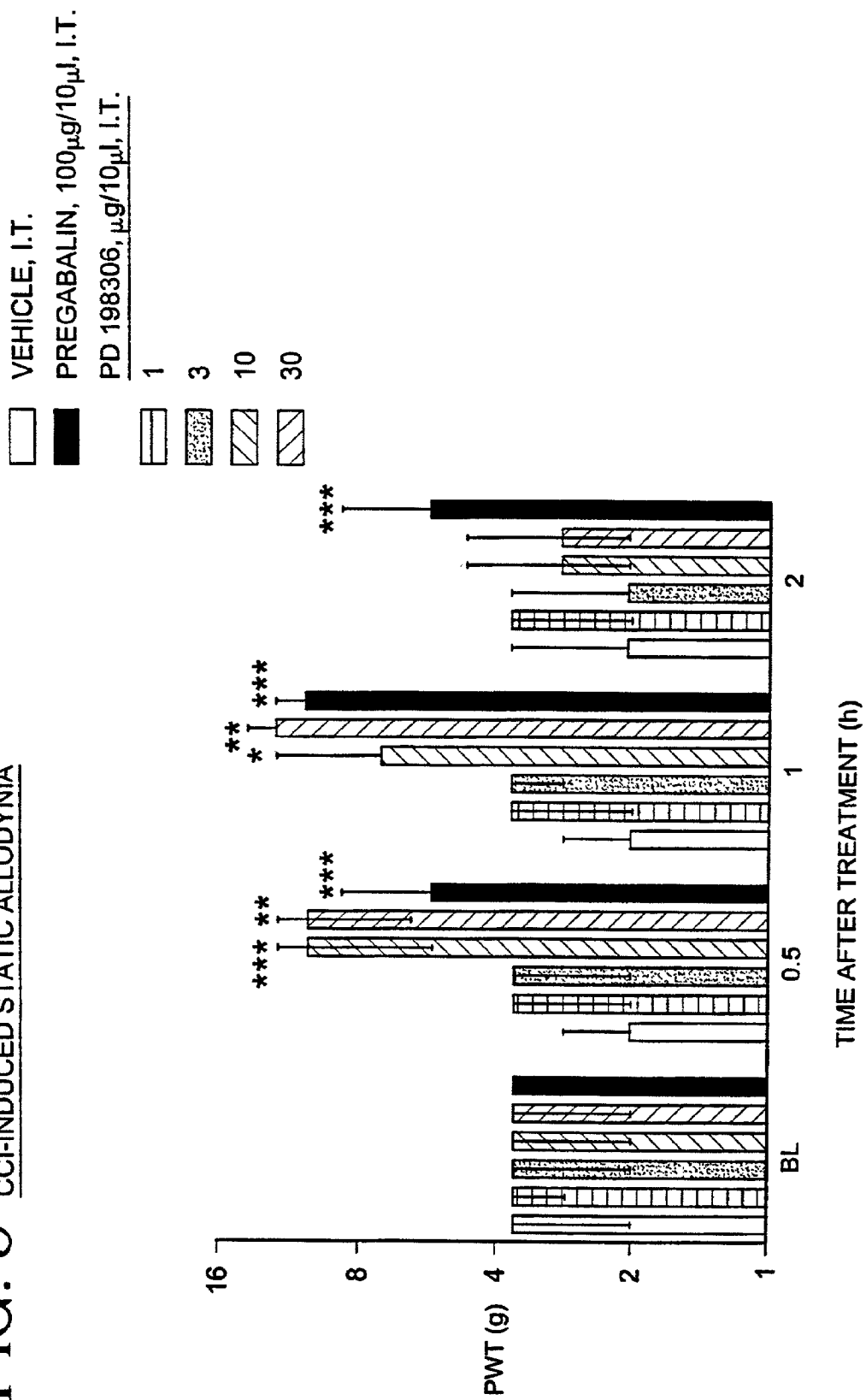

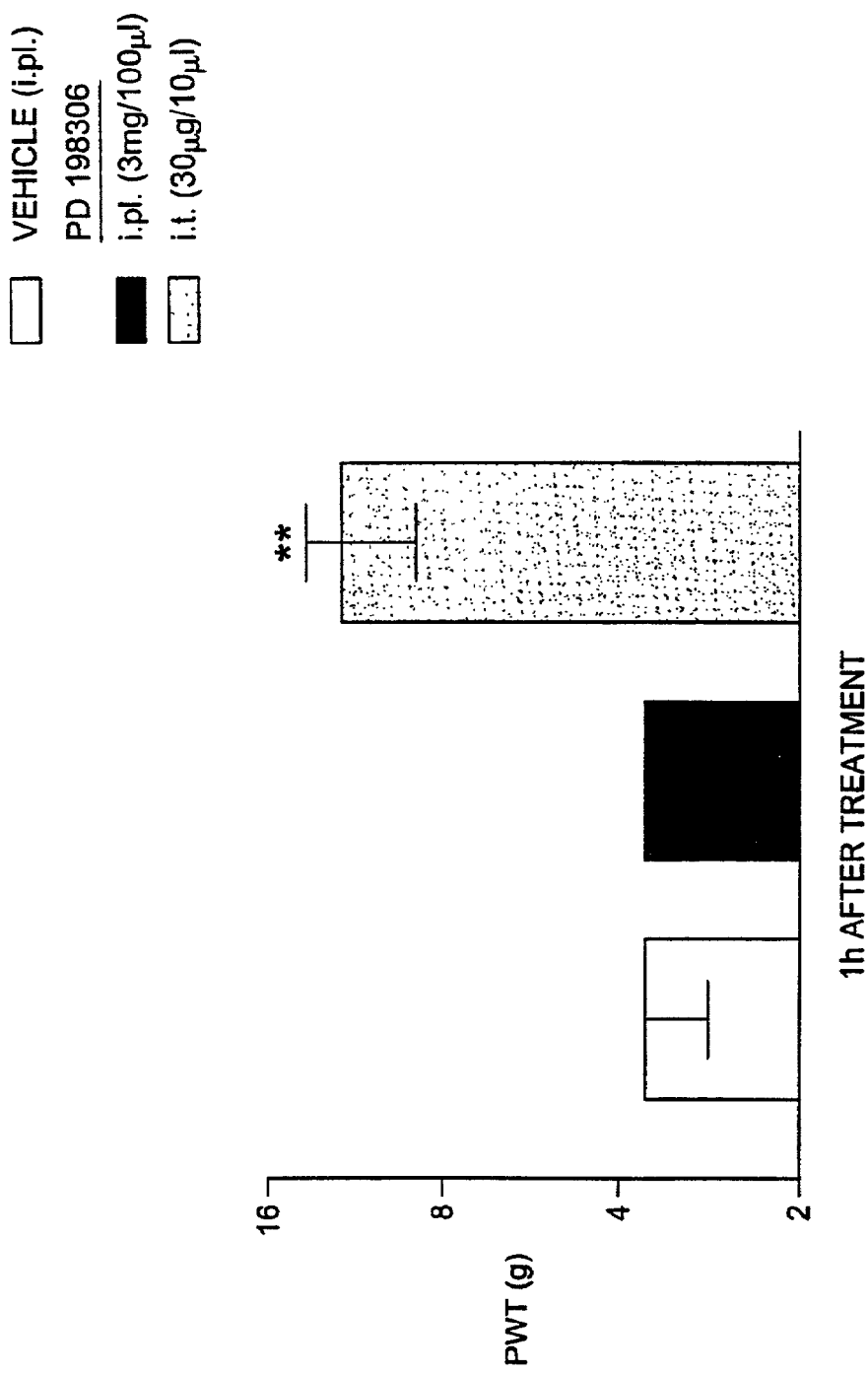
FIG. 6  EFFECT OF INTRAPLANTAR (i.pl.) ADMINISTRATION OF PD 198306 ON STREPTOZOCIN-INDUCED STATIC ALLODYNIA

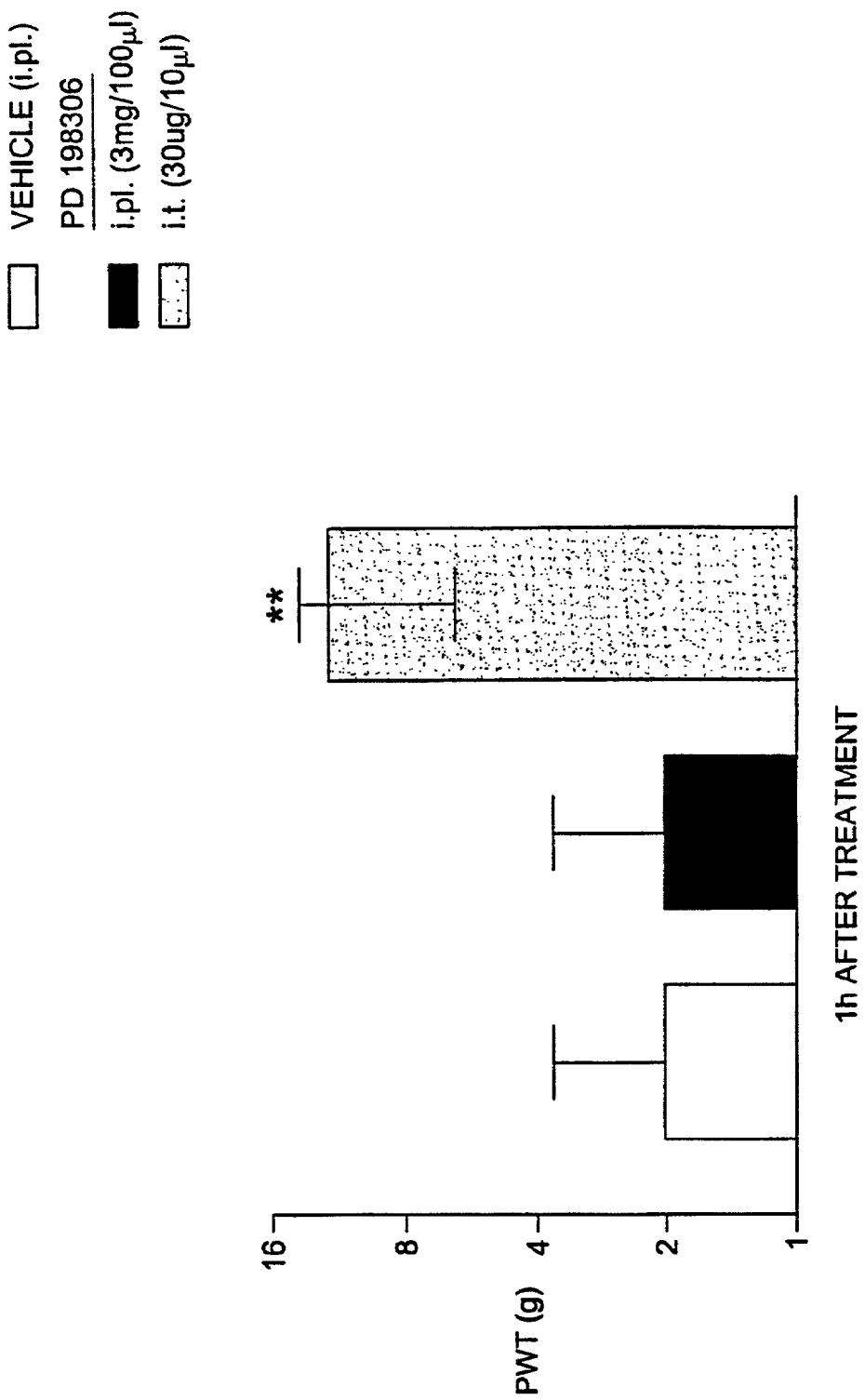
FIG. 7 EFFECT OF INTRAPLANTAR (i.pl.) ADMINISTRATION OF PD 198306 ON CCI-INDUCED STATIC ALLODYNIA

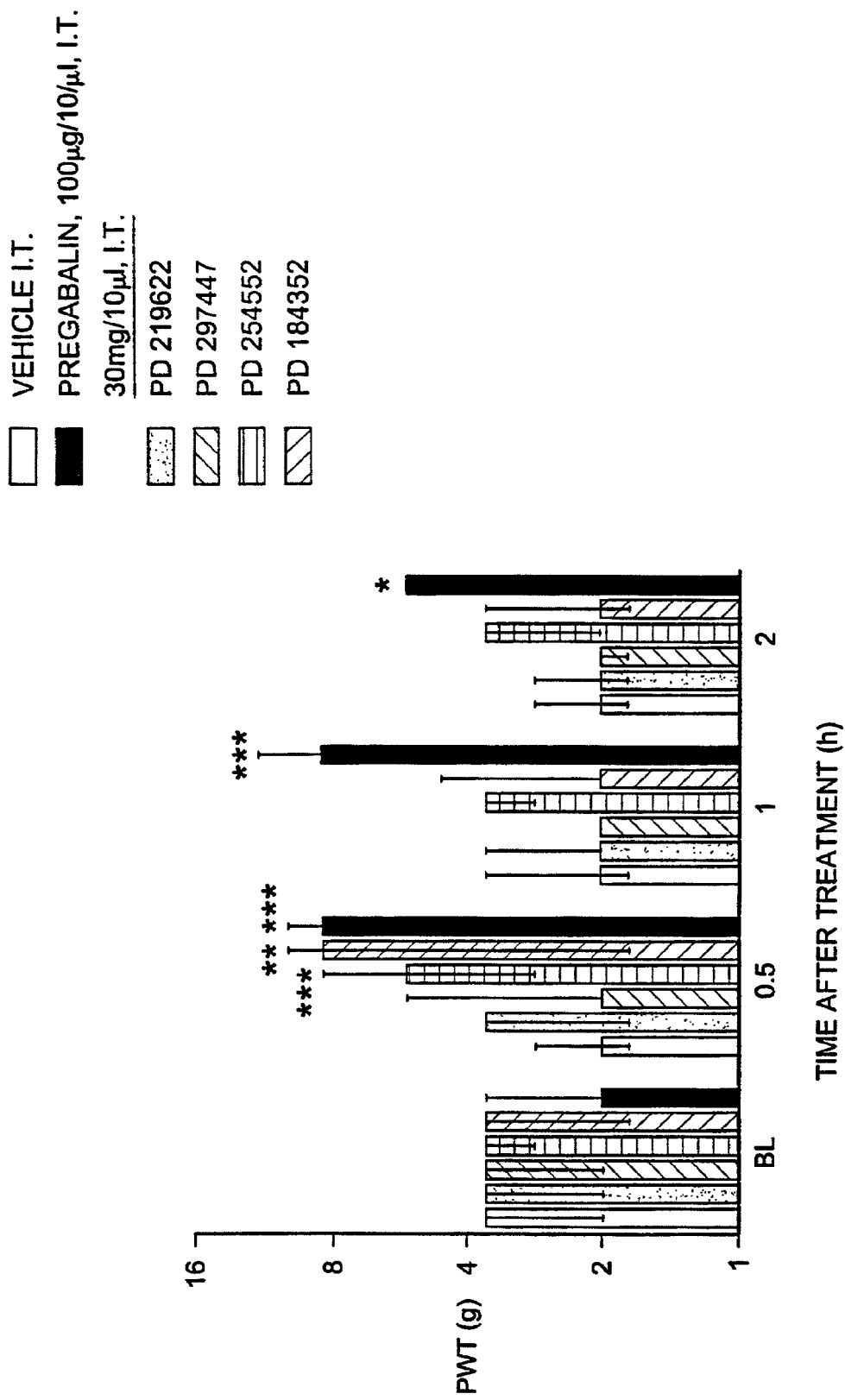
FIG. 8 EFFECT OF INTRATHECAL (i.t.) ADMINISTRATION OF PD 219622, PD 297447, PD 184352, PD 254552 OR PREGABALIN ON CCI-INDUCED STATIC ALLODYNIA

METHOD FOR TREATING CHRONIC PAIN USING MEK INHIBITORS

This application is a 371 application of PCT/US00/18345 filed Jul. 5, 2000, which claims the benefit of priority to U.S. provisional application Ser. No. 60/144,418 filed Jul. 16, 1999.

BACKGROUND

The invention features a method for treating chronic pain using MEK inhibitors. Chronic pain includes neuropathic pain, and chronic inflammatory pain.

Abnormality anywhere in a nerve pathway disrupts nerve signals, which in turn are abnormally interpreted in the brain, causing neuropathic pain. Neuropathic pain may be, for example, a deep ache, a burning sensation, or hypersensitivity to touch. Diseases or conditions associated with neuropathic pain include, without limitation, diabetic neuropathy, causalgia, plexus avulsion, neuroma, vasculitis, crush injury, viral infections (e.g., herpes virus infection or HIV), constriction injury, tissue injury, nerve injury from the periphery to the central nervous system, limb amputation, hypothyroidism, uremia, chronic alcoholism, post-operative pain, arthritis, back pain, and vitamin deficiencies.

Infections such as herpes zoster (shingles) can cause nerve inflammation and produce postherpetic neuralgia, a chronic burning localized to the area of viral infection. Hyperalgesia is when an already noxious stimulus becomes more painful, and allodynia, when a previously non-noxious stimulus becomes painful (such as contact of clothing or a breeze). Reflex sympathetic dystrophy is accompanied by swelling and sweating or changes in local blood flow, tissue atrophy, or osteoporosis. Causalgia, including severe burning pain and swelling, sweating, and changes in blood flow, may follow an injury or disease of a major nerve such as the sciatic nerve. Some types of chronic low back pain can have a neuropathic component (e.g., sciatica, postpoliomyelitis and CPRM). Neuropathic pain may also be induced by cancer or chemotherapy.

Neuropathic pain is currently treated with anticonvulsants such as carbamazepine and antidepressants such as amitryptaline. NSAIDS and opioids generally have little effect (Fields et al 1994 *Textbook of Pain* p 991–996 (pub: Churchill Livingstone), James & Page 1994 *J. Am. Pediatr. Med. Assoc.* 8: 439–447, Galer, 1995 *Neurology* 45 S17–S25. Neuropathic conditions that have been treated with gabapentin include: postherpetic neuralgia, postpoliomyelitis, CPRM, HIV-related neuropathy, trigeminal neuralgia, and reflex sympathetic dystrophy (RSD). The generally weak efficacy of antiinflammatory agents suggests that the mechanism for chronic pain is separate from hyperalgesia.

SUMMARY OF THE INVENTION

The invention features a method for treating chronic pain, which method includes the step of administering a composition including a MEK inhibitor to a patient in need of such treatment. Chronic pain includes neuropathic pain, idiopathic pain, and pain associated with vitamin deficiencies, uremia, hypothyroidism post-operative pain, arthritis, back pain, and chronic alcoholism. The invention also features compositions as disclosed, formulated for the treatment of chronic pain. Such a composition may include one or more MEK inhibitor compounds having a structure disclosed in patent applications U.S. Ser. No. 60/115,873, filed Jan. 13, 1999, PCT/US99/30483, international filing date Dec. 21, 1999.

Examples of MEK inhibitors include a compound having the formula (I) below:

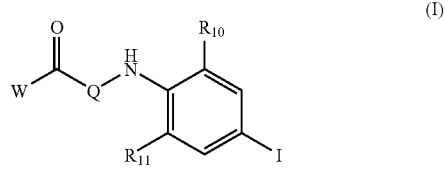

In formula (I), W is $OR_1$, $NR_2OR_1$, $NR_4R_B$, $NR_2NR_4R_B$, $O(CH_2)_{2-4}NR_4R_B$, or $NR_2(CH_2)_{2-4}NR_4R_B$. $R_1$ is H, $C_{1-8}$alkyl, $C_{3-8}$alkenyl, $C_{3-8}$alkynyl, $C_{3-8}$cycloalkyl, phenyl, (phenyl)$C_{1-4}$alkyl, (phenyl)$C_{3-4}$alkenyl, (phenyl)$C_{3-4}$alkynyl, ($C_{3-8}$cycloalkyl)$C_{1-4}$alkyl, ($C_{3-8}$cycloalkyl)$C_{3-4}$alkenyl, ($C_{3-8}$cycloalkyl)$C_{3-4}$alkynyl, $C_{3-8}$heterocyclic radical, ($C_{3-8}$ heterocyclic radical)$C_{1-4}$alkyl, ($C_{3-8}$heterocyclic radical)$C_{3-4}$alkenyl, ($C_{3-8}$heterocyclic radical)$C_{3-4}$alkynyl or $(CH_2)_{2-4}NR_CR_D$. $R_2$ is H, $C_{1-4}$alkyl, phenyl, $C_{3-6}$cycloalkyl, $C_{3-6}$heterocyclic radical, or ($C_{3-6}$cycloalkyl)methyl. $R_4$ is H, $C_{1-6}$alkyl, $C_{3-8}$alkenyl, $C_{3-8}$alkynyl, $C_{3-8}$cycloalkyl, phenyl, ($C_{3-8}$cycloalkyl)$C_{1-4}$alkyl, ($C_{3-8}$cycloalkyl)$C_{3-4}$alkenyl, ($C_{3-8}$cycloalkyl)$C_{3-4}$alkynyl, $C_{3-8}$heterocyclic radical, ($C_{3-8}$heterocyclic radical)$C_{1-4}$alkyl, (aminosulfonyl)phenyl, [(aminosulfonyl)phenyl]$C_{1-4}$alkyl, (aminosulfonyl)$C_{1-6}$alkyl, (aminosulfonyl)$C_{3-6}$cycloalkyl, [(aminosulfonyl)$C_{3-6}$cycloalkyl]$C_{1-4}$alkyl, or $(CH_2)_{2-4}NR_CR_D$. $R_B$ is H, $C_{1-8}$alkyl, $C_{3-8}$alkenyl, $C_{3-8}$alkynyl, $C_{3-8}$cycloalkyl, or phenyl. Q is one of the following formulae (i)–(iii):

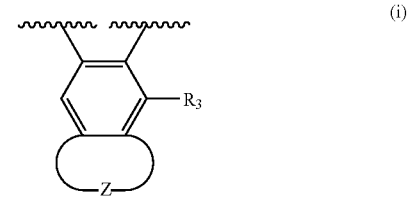

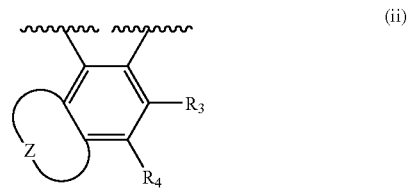

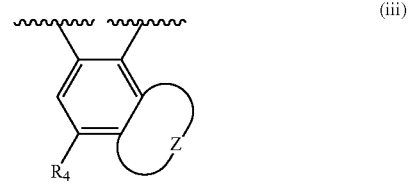

$R_3$ is H or F; $R_4$ is halo, $NO_2$, $SO_2NR_O(CH_2)_{2-4}NR_ER_F$, $SO_2NR_ER_F$ or (CO)T. T is $C_{1-8}$alkyl, $C_{3-8}$cycloalkyl, ($NR_E$ R$_F$)C$_{1-4}$alkyl, OR$_F$, —NR$_O$(CH$_2$)$_{2-4}$NR$_E$R$_F$, or NR$_E$R$_F$; Z is one of the following formulae (iv)–(viii):

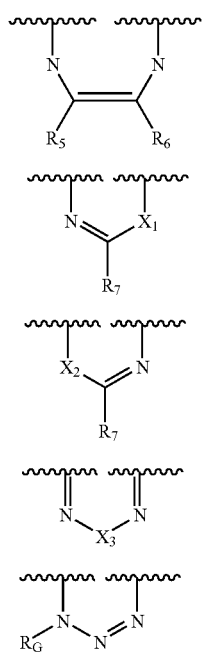

One of R$_5$ and R$_6$ is H or methyl and the other of R$_5$ and R$_6$ is H, C$_{1-6}$alkyl, C$_{2-6}$alkenyl, C$_{2-6}$alkynyl, phenyl, benzyl, or —M-E-G. M is O, CO, SO$_2$, NR$_J$, (CO)NR$_H$, NR$_H$ (CO), NR$_H$ (SO$_2$), (SO$_2$)NR$_H$, or CH$_2$. E is (CH$_2$)$_{1-4}$ or (CH$_2$)$_m$O(CH$_2$)$_p$ where $1 \leq$ (each of m and p) $\leq 3$ and $2 \leq (m+p) \leq 4$; or E is absent. G is R$_K$, OR$_J$ or NR$_J$R$_K$, provided that if p=1, then G is H. R$_7$ is H, C$_{1-4}$alkyl, C$_{2-4}$alkenyl, C$_{2-4}$alkynyl, C$_{3-6}$cycloalkyl, phenyl, 2-pyridyl, 3-pyridyl, 4-pyridyl, (CH$_2$)$_{1-2}$Ar, where Ar is phenyl, 2-pyridyl 3-pyridyl, or 4-pyridyl, SO$_2$NR$_H$(CH$_2$)$_{2-4}$NR$_J$R$_K$, (CO)(CH$_2$)$_{2-4}$NR$_J$R$_K$ or (CO)NR$_H$(CH$_2$)$_{2-4}$NR$_J$R$_K$. X$_1$ is O, S, NR$_8$, or CHR$_9$; X$_2$ is O, S, or CHR$_9$; and X$_3$ is O or S. In one embodiment, if X$_1$ or X$_2$ is CHR$_9$, the disclosed compound may also be a tautomerized indole. R$_8$ is H, C$_{1-4}$alkyl, phenyl, 2-pyridyl, 3-pyridyl, 4-pyridyl, (CH$_2$)$_{1-2}$Ar, where Ar is phenyl, 2-pyridyl, 3-pyridyl, or 4-pyridyl, C$_{2-4}$alkenyl, C$_{2-4}$alkynyl, C$_{3-6}$cycloalkyl, or (C$_{2-4}$alkyl)NR$_L$R$_M$ provided R$_7$ and R$_8$ together have no more than 14 carbon atoms, exclusive of R$_L$, R$_M$, R$_J$ and R$_K$. R$_G$ is C$_{1-4}$alkyl, phenyl, 2-pyridyl, 3-pyridyl, 4-pyridyl, C$_{3-4}$alkenyl, C$_{3-4}$alkynyl, C$_{3-6}$cycloalkyl, (CO)OR$_P$, (C$_{2-4}$alkyl)NR$_L$R$_M$, (CO)NR$_N$(CH$_2$)$_{2-4}$NR$_L$R$_M$, (CO)NR$_L$R$_M$, (CO)(CH$_2$)$_{2-4}$-NR$_L$R$_M$, or (CH$_2$)$_{1-2}$Ar, where Ar is phenyl, 2-pyridyl, 3-pyridyl, or 4-pyridyl. R$_9$ is C$_{1-4}$alkyl, phenyl, 2-pyridyl, 3-pyridyl, 4-pyridyl, C$_{2-4}$alkenyl, C$_{2-4}$alkynyl, C$_{3-6}$cycloalkyl, (CO)OR$_P$, (C$_{2-4}$alkyl)NR$_L$R$_M$, (CO)NR$_N$(CH$_2$)$_{2-4}$NR$_L$R$_M$, (CO)NR$_L$R$_M$, (CO)(CH$_2$)$_{2-4}$-NR$_L$R$_M$, or (CH$_2$)$_{1-2}$Ar', where Ar' is phenyl, 2-pyridyl, 3-pyridyl, or 4-pyridyl. R$_P$ is H, C$_{1-6}$alkyl, phenyl, C$_{3-4}$alkenyl, C$_{3-4}$alkynyl, C$_{3-6}$cycloalkyl, or (CH$_2$)$_{2-4}$NR$_L$R$_M$; R$_{10}$ is H, methyl, halo, or NO$_2$; R$_{11}$ is H, methyl, halo, or NO$_2$. Each of R$_C$, R$_D$, R$_E$, R$_F$, R$_I$, R$_J$, R$_K$, R$_L$ and R$_M$ is independently selected from H, C$_{1-4}$alkyl, C$_{3-4}$alkenyl, C$_{3-4}$alkynyl, C$_{3-6}$cycloalkyl, and phenyl; each of NR$_C$R$_D$, NR$_E$R$_F$, NR$_J$R$_K$, and NR$_L$R$_M$ can also independently be morpholinyl, piperazinyl, pyrrolidinyl, or piperadinyl. Each of R$_H$, R$_N$, and R$_O$ is independently H, methyl, or ethyl.

Finally, each hydrocarbon radical or heterocyclic radical above is optionally substituted with between 1 and 3 substituents independently selected from halo, C$_{1-4}$alkyl, C$_{3-6}$cycloalkyl, C$_{2-4}$alkenyl, C$_{2-4}$alkynyl, phenyl, hydroxyl, amino, (amino)sulfonyl, and NO$_2$, wherein each substituent alkyl, cycloalkyl, alkenyl, alkynyl or phenyl is in turn optionally substituted with between 1 and 3 substituents independently selected from halo, C$_{1-2}$alkyl, hydroxyl, amino, and NO$_2$. In addition to the above compounds, the invention also provides a pharmaceutically-acceptable salt or C$_{1-7}$ester thereof.

Preferred embodiments of the invention include methods using one or more of the following compounds:

(a) said MEK inhibitor has a structure selected from: 7-fluoro-6-(4-iodo-2-methyl-phenylamino)-1H-benzoimidazole-5-carboxylic acid cyclopropylmethoxy-amide; 7-fluoro-6-(4-iodo-2-methyl-phenylamino)-6,7-dihydro-1H-benzoimidazole-5-carboxylic acid (hydrochloride); 7-fluoro-6-(4-iodo-2-methyl-phenylamino)-1H-benzoimidazole-5-carboxylic acid; 7-fluoro-6-(4-iodo-2-methyl-phenylamino)-3H-benzoimidazole-5-carboxylic acid (2-hydroxy-ethoxy)-amide; 6-(2-chloro-4-iodo-phenylamino)-7-fluoro-1H-benzoimidazole-5-carboxylic acid; and 7-fluoro-6-(4-iodo-2-methyl-phenylamino)-1H-benzoimidazole-5-carboxylic acid pentafluorophenyl ester; and (b) said MEK inhibitor has a structure selected from: 7-fluoro-6-(4-iodo-2-methyl-phenylamino)-1H-benzoimidazole-5-carboxylic acid cyclopropylmethoxy-amide; and 7-fluoro-6-(4-iodo-2-methyl-phenylamino)-3H-benzoimidazole-5-carboxylic acid (2-hydroxy-ethoxy)-amide.

The invention also relates to a pharmaceutical composition including (a) a benzoheterocycle (e.g., of formula I) and (b) a pharmaceutically-acceptable carrier.

BRIEF DESCRIPTION OF THE FIGURES

FIG. 1 is a bar graph representing the paw withdrawal threshold (PWT) in grams as a function of time in days. The empty, cross-hatched, and single-hatched bars are vehicle, PD 198306, and pregabalin, respectively. The arrows indicate time of drug administration (30 mg/kg, p.o.).

FIG. 2. is a bar graph representing the force required in grams to elicit paw withdrawal using von Frey hair filaments as a function of time in days. Baseline (BL) measurements were taken before treatment. Animals received a single p.o. administration of PD 198306 (3–30 mg/kg), or pregabalin (30 mg/kg) and withdrawal thresholds were re-assessed 1 h after treatment. Treatments were repeated twice a day for two days. Results are expressed median±1$^{st}$ and 3$^{rd}$ quartiles. *P<0.05, P<0.01, *P<0.001 significantly different from vehicle treated animals (Mann-Whitney t test; n=7–8).

FIG. 3. is a bar graph representing the force required in grams to elicit paw withdrawal using von Frey hair filaments as a function of time in days. Baseline (BL) measurements were taken before treatment. Animals received a single p.o. administration of PD 198306 (3–30 mg/kg), or pregabalin (30 mg/kg) and withdrawal thresholds were re-assessed 1 h after treatment. Treatments were repeated twice a day for two days. Results are expressed median±1$^{st}$ and 3$^{rd}$ quartiles. **P<0.01 significantly different from vehicle treated animals (Mann-Whitney t test: n=6).

FIG. 4. is a bar graph representing the force required in grams to elicit paw withdrawal using von Frey hair filaments as a function of time in days. Baseline (BL) measurements were taken before treatment. Animals received a single i.t. administration of PD 198306 (1–30 μg/10 μl), or pregabalin (100 µg/10 µl) and withdrawal thresholds were re-assessed at 30 min, 1 h and 2 h after treatment. Results are expressed median±1$^{st}$ and 3$^{rd}$ quartiles. *P<0.05, ***P<0.001 significantly different from vehicle treated animals (Mann-Whitney t test; n=7–9).

FIG. 5. is a bar graph representing the force required in grams to elicit paw withdrawal using von Frey hair filaments as a function of time in days. Baseline (BL) measurements were taken before treatment. Animals received a single i.t. administration of PD 198306 (1–30 µg/10 µl), or pregabalin (100 µg/10 µl) and withdrawal thresholds were re-assessed at 30 min, 1 h and 2 h after treatment. Results are expressed median±1$^{st}$ and 3$^{rd}$ quartiles. *P<0.05, P<0.01, *P<0.001 significantly different from vehicle treated animals (Mann-Whitney t test; n=6–8).

FIG. 6 is a bar graph representing the force required in grams to elicit paw withdrawal using von Frey hair filaments as a function of time in days. Animals received a single intraplantar (i.pl.) administration of PD 198306 (3 mg/100 µl), or an intrathecal injection of PD 198306 (30 µg/10 µl) and withdrawal thresholds were re-assessed 1 h after treatment. Results are expressed median±1$^{st}$ and 3$^{rd}$ quartiles. **P<0.01 significantly different from vehicle treated animals (Mann-Whitney t test; n=6–9).

FIG. 7. is a bar graph representing the force required in grams to elicit paw withdrawal using von Frey hair filaments as a function of time in days. Animals received a single intraplantar (i.pl.) administration of PD 198306 (3 mg/100 µl), or an intrathecal injection of PD 198306 (30 µg/10 µl) and withdrawal thresholds were re-assessed 1 h after treatment. Results are expressed median±1$^{st}$ and 3$^{rd}$ quartiles. **P<0.01 significantly different from vehicle treated animals (Mann-Whitney t test; n=6).

FIG. 8 is a bar graph representing the force required in grams to elicit paw withdrawal using von Frey hair filaments. Baseline (BL) measurements were taken before treatment. Animals received a single i.t. administration of PD219622, PD297447, PD 184352, or PD 254552 (30 µg/10 µl), or pregabalin (100 µg/10 µl) and withdrawal thresholds were re-assessed at 30 min, 1 h and 2 h after treatment. Results are expressed median±1$^{st}$ and 3$^{rd}$ quartiles. *P<0.05, P<0.01, *P<0.001 significantly different from vehicle treated animals (Mann-Whitney t test; n=7–8).

DETAILED DESCRIPTION

The compounds disclosed herein are pharmaceutically active, for example, they inhibit MEK. MEK enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted form the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., MEK$_1$ and MEK$_2$) which then activates MAP kinase, ERK (ERK$_1$ and ERK$_2$). Activation of MAP kinase by mitogens appears to be essential for proliferation; constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid.

This double phosphorylation activates MAP kinase at least 100-fold. Activated MAP kinase can then catalyze the phosphorylation of a large number of proteins, including several transcription factors and other kinases. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

The effect of the MEK inhibitor PD 198306 has been investigated in two animal models of neuropathic pain by assessing static allodynia with von Frey hairs.

Oral administration of PD 198306 (3–30 mg/kg) had no effect in the model of chronic constriction injury of the sciatic nerve (CCI). However, after repeated administration (3 doses over two days) it had a transient effect in the diabetic neuropathy model (streptozocin). This may be due to disorders of the blood-brain barrier induced by the diabetic condition in these animals, thus allowing central action of the compound. Intrathecal administration of PD 198306 (1–30 µg) dose-dependently blocked static allodynia in both the streptozocin and the CCI models of neuropathic pain, with minimum effective doses (MED) of 3 and 10 µg respectively. The highest dose used (30 µg) totally blocked the maintenance of static allodynia, for up to 1 h. Intraplantar administration of PD 198306 (3 mg/100 µl) at a dose 100-fold higher than the dose shown to be effective intrathecally (30 µg/10 µl) had no effect on static allodynia in either of the neuropathic pain models. This finding confirms the lack of effect seen after systemic administration and suggests a central site of action for the compound.

From this study we can suggest the use of MEK inhibitors as potential new therapeutic tools for chronic pain. The study of potential side-effects, especially related to memory, of future brain-penetrant MEK inhibitors will indicate the therapeutic window for this novel class of compounds in the treatment of pain.

A. Terms

Certain terms are defined below and by their usage throughout this disclosure.

Alkyl groups include aliphatic (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, n-butyl, isobutyl, t-butyl, pentyl, isopentyl, 2,3-dimethylpropyl, hexyl, 2,3-dimethylhexyl, 1,1-dimethylpentyl, heptyl, and octyl. Cycloalkyl groups include cyclopropyl, cyclobutyl, cyclopentyl, cyclohexyl, cycloheptyl, and cyclooctyl.

Alkyl groups can be substituted with 1, 2, 3 or more substituents which are independently selected from halo (fluoro, chloro, bromo, or iodo), hydroxy, amino, alkoxy, alkylamino, dialkylamino, cycloalkyl, aryl, aryloxy, arylalkyloxy, heterocyclic radical, and (heterocyclic radical)oxy. Specific examples include fluoromethyl, hydroxyethyl, 2,3-dihydroxyethyl, (2- or 3-furanyl)methyl, cyclopropylmethyl, benzyloxyethyl, (3-pyridinyl)methyl, (2- or 3-furanyl) methyl, (2-thienyl)ethyl, hydroxypropyl, aminocyclohexyl, 2-dimethylaminobutyl, methoxymethyl, N-pyridinylethyl, diethylaminoethyl, and cyclobutylmethyl.

Alkenyl groups are analogous to alkyl groups, but have at least one double bond (two adjacent $sp^2$ carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof; like alkyl groups, unsaturated groups may be straight chain or branched, and they may be substituted as described both above for alkyl groups and throughout the disclosure by example. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl, and 2-methyl-2-propenyl. In formula (I), alkenyls and alkynyls can be $C_{2-4}$ or $C_{2-8}$, for example, and are preferably $C_{3-4}$ or $C_{3-8}$.

More general forms of substituted hydrocarbon radicals include hydroxyalkyl, hydroxyalkenyl, hydroxyalkynyl, hydroxycycloalkyl, hydroxyaryl, and corresponding forms for the prefixes amino-, halo- (e.g., fluoro-, chloro-, or bromo-), nitro-, alkyl-, phenyl-, cycloalkyl- and so on, or combinations of substituents. According to formula (I), therefore, substituted alkyls include hydroxyalkyl, aminoalkyl, nitroalkyl, haloalkyl, alkylalkyl (branched alkyls, such as methylpentyl), (cycloalkyl)alkyl, phenylalkyl, alkoxy, alkylaminoalkyl, dialkylaminoalkyl, arylalkyl, aryloxyalkyl, arylalkyloxyalkyl, (heterocyclic radical)alkyl, and (heterocyclic radical)oxyalkyl. $R_1$ thus includes hydroxyalkyl, hydroxyalkenyl, hydroxyalkynyl, hydroxycycloalkyl, hydroxyaryl, aminoalkyl, aminoalkenyl, aminoalkynyl, aminocycloalkyl, aminoaryl, alkylalkenyl, (alky-laryl)alkyl, (haloaryl)alkyl, (hydroxyaryl)alkynyl, and so forth. Similarly, $R_A$ includes hydroxyalkyl and aminoaryl, and $R_B$ includes hydroxyalkyl, aminoalkyl, and hydroxyalkyl(heterocyclic radical)alkyl.

Heterocyclic radicals, which include but are not limited to heteroaryls, include: furyl, oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their non-aromatic counterparts. Further examples of heterocyclic radicals include piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl.

Selective MEK 1 or MEK 2 inhibitors are those compounds which inhibit the MEK 1 or MEK 2 enzymes, respectively, without substantially inhibiting other enzymes such a MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth (1/50) that of its $IC_{50}$ for one of the above-named other enzymes. Preferably, a selective inhibitor has an $IC_{50}$ that is at least 1/100, more preferably 1/500, and even more preferably 1/1000, 1/5000, or less than that of its $IC_{50}$ or one or more of the above-named enzymes.

B. Compounds

One aspect of the invention features the use of compounds shown in formula (I) in the Summary section. Embodiments of the invention includes compounds of formula (I) wherein: (a) Q is formula (i); (b) $R_3$ is H or fluoro; (c) $R_4$ is fluoro, chloro, or bromo; (d) $R_{10}$ is H, methyl, fluoro, or chloro; (e) $R_{11}$ is methyl, chloro, fluoro, nitro, or hydrogen; (f) $R_{11}$ is H; (g) $R_{11}$ is fluoro; (h) each of $R_{10}$ and $R_{11}$ is fluoro; (i) $R_1$ is H, methyl, ethyl, propyl, isopropyl, isobutyl, benzyl, phenethyl, allyl, $C_{3-5}$alkenyl, $C_{3-6}$cycloalkyl, ($C_{3-5}$cycloalkyl)$C_{1-2}$alkyl, ($C_{3-5}$heterocyclic radical)$C_{1-2}$alkyl, or $(CH_2)_{2-4}NR_CR_D$; (j) $R_1$ is H or ($C_{3-4}$cycloalkyl)$C_{1-2}$alkyl; (k) $R_2$ is H or methyl; (l) $R_A$ has at least one hydroxyl substituent; (m) $R_A$ is H, methyl, ethyl, isobutyl, hydroxyethyl, phenyl, 2-piperidin-1-yl-ethyl, 2,3-dihydroxy-propyl, 3-[4-(2-hydroxyethyl)-piperazin-2-yl]-propyl, 2-pyrrolidin-1-yl-ethyl, or 2-diethylamino-ethyl; and $R_B$ is H; or where $R_B$ is methyl and $R_A$ is phenyl.; (n) W is $NR_AR_B$ or $NR_2NR_AR_B$; (o) W is $NR_2(CH_2)_{2-4}NR_AR_B$ or $O(CH_2)_{2-3}NR_AR_B$; (p) W is $NR_2OR_1$; (q) W is $OR_1$; (r) Z is formula (v); or (s) $X_1$ is $NR_8$, and $R_7$ is H; or (t) combinations thereof. In formula (I), the values for Z are shown left to right, or in a counter-clockwise orientation around the phenyl ring of Q.

According to one aspect of the invention, the compound of formula (I) has a structure wherein: Q is formula (i) or (ii); $R_3$ is H or fluoro; $R_4$ is fluoro, chloro, or bromo; $R_{10}$ is H, methyl, or chloro; $R_{11}$ is chloro, fluoro, or hydrogen; $R_1$ is H, methyl, ethyl, propyl, isopropyl, isobutyl, benzyl, phenethyl, allyl, $C_{3-5}$alkenyl, $C_{3-6}$cycloalkyl, ($C_{3-5}$cycloalkyl)$C_{1-2}$alkyl, ($C_{3-5}$heterocyclic radical)$C_{1-2}$alkyl, or $(CH_2)_{2-4}NR_CR_D$; $R_1$ is H or ($C_{3-4}$cycloalkyl)$C_{1-2}$alkyl; $R_2$ is H or methyl; and Z is formula (v) or (vi). One embodiment of this aspect, $X_1$ is $NR_8$. An example would be 7-fluoro-6-(4-iodo-2-methyl-phenylamino)-1[(2'-morpholinyl)-ethyl]-2-(phenyl)-benzoimidazole-5-carboxylic acid cyclopropyl-methoxy-amide.

Embodiments of the invention also include compounds wherein $R_{10}$ is H; $R_{10}$ is methyl or chloro; and where $R_{10}$ is chloro. In some embodiments, $R_7$ and $R_8$ together have no more than 14 carbon atoms, exclusive of $R_L$, $R_M$, $R_J$ and $R_K$. Examples of this include compounds wherein $R_7$ and $R_8$ together have no more than 13 carbon atoms; no more than 7, 8, or 10 carbon atoms; between 4 and 8 carbon atoms; between 1 and 10 carbon atoms; between 1 and 8 carbon atoms; and no more than 6 carbon atoms.

Preferably, where one of $R_1$, $R_2$, $R_A$, $R_B$, $R_C$, $R_D$, $R_E$, $R_F$, $R_I$, $R_J$, $R_K$, $R_L$, $R_M$, $R_G$, $R_H$, $R_N$, $R_O$, and $R_P$ is an alkenyl or alkynyl group, its double or triple bond, respectively, is not adjacent the point of attachment. For example, where W is $NR_2OR_1$, $R_2$ is preferably prop-2-ynyl, or but-2 or 3-enyl, and less preferably prop-1-ynyl or but-1-enyl.

Listed below are some of the preferred structures which can be synthesized utilizing Schemes 1, 2, 10, and 11. Free acids, free hydroxamic acids, and cyclopropylmethyl hydroxamates are grouped together. For example, compounds 1, 11, and 21 differ only by "W" (as defined in the claims); compounds 2, 12, and 22 are similarly related. Preferred compounds also include the 2-chloro (replacing 2-methyl) analogs of the listed compounds.

Examples of compounds include: 7-Fluoro-6-(4-iodo-2-methyl-phenylamino)-1H-benzoimidazole-5-carboxylic acid (APK $IC_{50}$=47±17 nM); 7-Fluoro-6-(4-iodo-2-methyl-phenylamino)-benzooxazole-5-carboxylic acid; 7-Fluoro-6-(4-iodo-2-methyl-phenylamino)-benzothiazole-5-carboxylic acid; 7-Fluoro-6-(4-iodo-2-methyl-phenylamino)-benzo[1,2,5]thiadiazole-5-carboxylic acid; 7-Fluoro-6-(4-iodo-2-methyl-phenylamino)-benzo[1,2,5]oxadiazole-5-carboxylic acid; 7-Fluoro-6-(4-iodo-2-methyl-phenylamino)-2-(2-hydroxyethyl)-1H-benzoimidazole-5-carboxylic acid; 7-Fluoro-6-(4-iodo-2-methyl-phenylamino)-2-(2-dimethylamino-ethyl)-1H-benzoimidazole-5-carboxylic acid; 7-Fluoro-6-(4-iodo-2-methyl-phenylamino)-1-acetyl-benzoimidazole-5-carboxylic acid; 8-Fluoro-7-(4-iodo-2-methyl-phenylamino)-quinoxaline-6-carboxylic acid; 7-Fluoro-6-(4-iodo-2-methyl-phenylamino)-1H-benzotriazole-5-carboxylic acid; 7-Fluoro-6-(4-iodo-2-methyl-phenylamino)-1H-benzoimidazole-5-carboxylic acid hydroxamide; 7-Fluoro-6-(4-iodo-2-methyl-phenylamino)-benzooxazole-5-carboxylic acid hydroxyamide; 7-Fluoro-6-(4-iodo-2-methyl-phenylamino)-benzothiazole-5-carboxylic acid hydroxyamide; 7-Fluoro-6-(4-iodo-2-methyl-phenylamino)-benzo[1,2,5]thiadiazole-5-carboxylic acid hydroxyamide; 7-Fluoro-6-(4-iodo-2-methyl-phenylamino)-benzo[1,2,5]oxadiazole-5-carboxylic acid hydroxyamide; 7-Fluoro-6-(4-iodo-2-methyl-phenylamino)-2-(2-hydroxyethyl)-1H-benzoimidazole-5-carboxylic acid hydroxyamide; 7-Fluoro-6-(4-iodo-2-methyl-phenylamino)-2-(2-dimethylaminoethyl)-1H-benzoimidazole-5-carboxylic acid hydroxyamide; 7-Fluoro-6-(4-iodo-2-methyl-phenylamino)-1-acetyl-benzoimidazole-5-carboxylic acid hydroxyamide; 8-Fluoro-7-(4-iodo-2-methyl-phenylamino)-quinoxaline-6-carboxylic acid hydroxyamide; 7-Fluoro-6-(4-iodo-2-methyl-phenylamino)-1H-benzotriazole-5-carboxylic acid hydroxyamide; 7-Fluoro-6-(4-iodo-2-methyl-phenylamino)-1H-benzoimidazole-5-carboxylic acid cyclopropylmethoxy-amide; 7-Fluoro-6-(4-iodo-2-methyl-phenylamino)-benzooxazole-5-carboxylic acid cyclopropylmethoxy-amide; 7-Fluoro-6-(4-iodo-2-methyl-phenylamino)-benzothiazole-5-carboxylic acid cyclopropylmethoxy-amide; 7-Fluoro-6-(4-iodo-2-methyl-phenylamino)-benzo[1,2,5]thiadiazole-5-carboxylic acid cyclopropylmethoxy-amide; 7-Fluoro-6-(4-iodo-2-methyl-phenylamino)-benzo[1,2,5]oxadiazole-5-carboxylic acid cyclopropylmethoxy-amide; 7-Fluoro-6-(4-iodo-2-methyl-phenylamino)-2-(2-hydroxyethyl)-1H-benzoimidazole-5-carboxylic acid cyclopropylmethoxy-amide; 7-Fluoro-6-(4-iodo-2-methyl-phenylamino)-2-(2-dimethylamino-ethyl)-1H-benzoimidazole-5-carboxylic acid cyclopropylmethoxy-amide; 7-Fluoro-6-(4-iodo-2-methyl-phenylamino)-1-acetyl-benzoimidazole-5-carboxylic acid cyclopropylmethoxy-amide; 8-Fluoro-7-(4-iodo-2-methyl-phenylamino)-quinoxaline-6-carboxylic acid cyclopropylmethoxy-amide; and 7-Fluoro-6-(4-iodo-2-methyl-phenylamino)-1H-benzotriazole-5-carboxylic acid cyclopropylmethoxy-amide.

The following is a list of examples representing schemes 3–9. As above, free acids, free hydroxamic acids, and cyclopropylmethyl hydroxamates are grouped together. For example, compounds 31, 45, and 59 differ only by "W" (as defined in the claims); compounds 32, 46, and 60 are similarly related. Preferred compounds also include the 2-chloro (replacing 2-methyl) analogs of the listed compounds.

Examples of compounds from schemes 3–9 include: 4-Fluoro-5-(4-iodo-2-methyl-phenylamino)-benzothiazole-6-carboxylic acid; 4-Fluoro-5-(4-iodo-2-methyl-phenylamino)-benzooxazole-6-carboxylic acid; 5-(2-Chloro-4-iodo-phenylamino)-6,7-difluoro-3H-benzoimidazole-4-carboxylic acid; 6,7-Difluoro-2-(2-hydroxy-ethyl)-5-(4-iodo-2-methyl-phenylamino)-3H-benzoimidazole-4-carboxylic acid; 6,7-Difluoro-5-(4-iodo-2-methyl-phenylamino)-benzooxazole-4-carboxylic acid; 6,7-Difluoro-5-(4-iodo-2-methyl-phenylamino)-benzothiazole-4-carboxylic acid; 7,8-Difluoro-6-(4-iodo-2-methyl-phenylamino)-quinoxaline-5-carboxylic acid; 6-(4-Iodo-2-methyl-phenylamino)-8-nitro-quinoxaline-5-carboxylic acid; 5-(4-Iodo-2-methyl-phenylamino)-8-nitro-quinoxaline-6-carboxylic acid; 8-Chloro-5-(4-iodo-2-methyl-phenylamino)-quinoxaline-6-carboxylic acid; 3-Cyclopropyl-7-(4-iodo-2-methyl-phenylamino)-3H-benzoimidazole-4,6-dicarboxylic acid 4-dimethylamide; 7-Bromo-4-(4-iodo-2-methyl-phenylamino)-benzooxazole-5-carboxylic acid; 7-(2-Chloro-4-iodo-phenylamino)-4-fluoro-benzothiazole-6-carboxylic acid; 7-(4-Iodo-2-methyl-phenylamino)-4-nitro-benzooxazole-6-carboxylic acid; 4-Fluoro-5-(4-iodo-2-methyl-phenylamino)-benzothiazole-6-carboxylic acid hydroxyamide; 4-Fluoro-5-(4-iodo-2-methyl-phenylamino)-benzooxazole-6-carboxylic acid hydroxyamide; 5-(2-Chloro-4-iodo-phenylamino)-6,7-difluoro-3H-benzoimidazole-4-carboxylic acid hydroxyamide; 6,7-Difluoro-2-(2-hydroxy-ethyl)-5-(4-iodo-2-methyl-phenylamino)-3H-benzoimidazole-4-carboxylic acid hydroxyamide; 6,7-Difluoro-5-(4-iodo-2-methyl-phenylamino)-benzooxazole-4-carboxylic acid hydroxyamide; 6,7-Difluoro-5-(4-iodo-2-methyl-phenylamino)-benzothiazole-4-carboxylic acid hydroxyamide; 7,8-Difluoro-6-(4-iodo-2-methyl-phenylamino)-quinoxaline-5-carboxylic acid hydroxyamide; 6-(4-Iodo-2-methyl-phenylamino)-8-nitro-quinoxaline-5-carboxylic acid hydroxyamide; 5-(4-Iodo-2-methyl-phenylamino)-8-nitro-quinoxaline-6-carboxylic acid hydroxyamide; 8-Chloro-5-(4-iodo-2-methyl-phenylamino)-quinoxaline-6-carboxylic acid hydroxyamide; 3-Cyclopropyl-7-(4-iodo-2-methyl-phenylamino)-3H-benzoimidazole-4,6-dicarboxylic acid 4-dimethylamide 6-hydroxyamide; 7-Bromo-4-(4-iodo-2-methyl-phenylamino)-benzooxazole-5-carboxylic acid hydroxyamide; 7-(2-Chloro-4-iodo-phenylamino)-4-fluoro-benzothiazole-6-carboxylic acid hydroxyamide; 7-(4-Iodo-2-methyl-phenylamino)-4-nitro-benzooxazole-6-carboxylic acid hydroxyamide; 4-Fluoro-5-(4-iodo-2-methyl-phenylamino)-benzothiazole-6-carboxylic acid cyclopropylmethoxy-amide; 4-Fluoro-5-(4-iodo-2-methyl-phenylamino)-benzooxazole-6-carboxylic acid cyclopropylmethoxy-amide; 5-(2-Chloro-4-iodo-phenylamino)-6,7-difluoro-3H-benzoimidazole-4-carboxylic acid cyclopropylmethoxy-amide; 6,7-Difluoro-2-(2-hydroxy-ethyl)-5-(4-iodo-2-methyl-phenylamino)-3H-benzoimidazole-4-carboxylic acid cyclopropylmethoxy-amide; 6,7-Difluoro-5-(4-iodo-2-methyl-phenylamino)-benzooxazole-4-carboxylic acid cyclopropylmethoxy-amide; 6,7-Difluoro-5-(4-iodo-2-methyl-phenylamino)-benzothiazole-4-carboxylic acid cyclopropylmethoxy-amide; 7,8-Difluoro-6-(4-iodo-2-methyl-phenylamino)-quinoxaline-5-carboxylic acid cyclopropylmethoxy-amide; 6-(4-Iodo-2-methyl-phenylamino)-8-nitro-quinoxaline-5-carboxylic acid cyclopropylmethoxy-amide; 5-(4-Iodo-2-methyl-phenylamino)-8-nitro-quinoxaline-6-carboxylic acid cyclopropylmethoxy-amide; 8-Chloro-5-(4-iodo-2-methyl-phenylamino)-quinoxaline-6-carboxylic acid cyclopropylmethoxy-amide; 3-Cyclopropyl-7-(4-iodo-2-methyl-phenylamino)-3H-benzoimidazole-4,6-dicarboxylic acid 4-dimethylamide 6-cyclopropylmethoxy-amide; 7-Bromo-4-(4-iodo-2-methyl-phenylamino)-benzooxazole-5-carboxylic acid cyclopropylmethoxy-amide; 7-(2-Chloro-4-iodo-phenylamino)-4-fluoro-benzothiazole-6-carboxylic acid cyclopropylmethoxy-amide; and 7-(4-Iodo-2-methyl-phenylamino)-4-nitro-benzooxazole-6-carboxylic acid cyclopropylmethoxy-amide.

C. Synthesis

The disclosed compounds can be synthesized according to the following eleven Schemes, or variants thereof. These synthetic strategies are further exemplified in Examples 1–22 below.

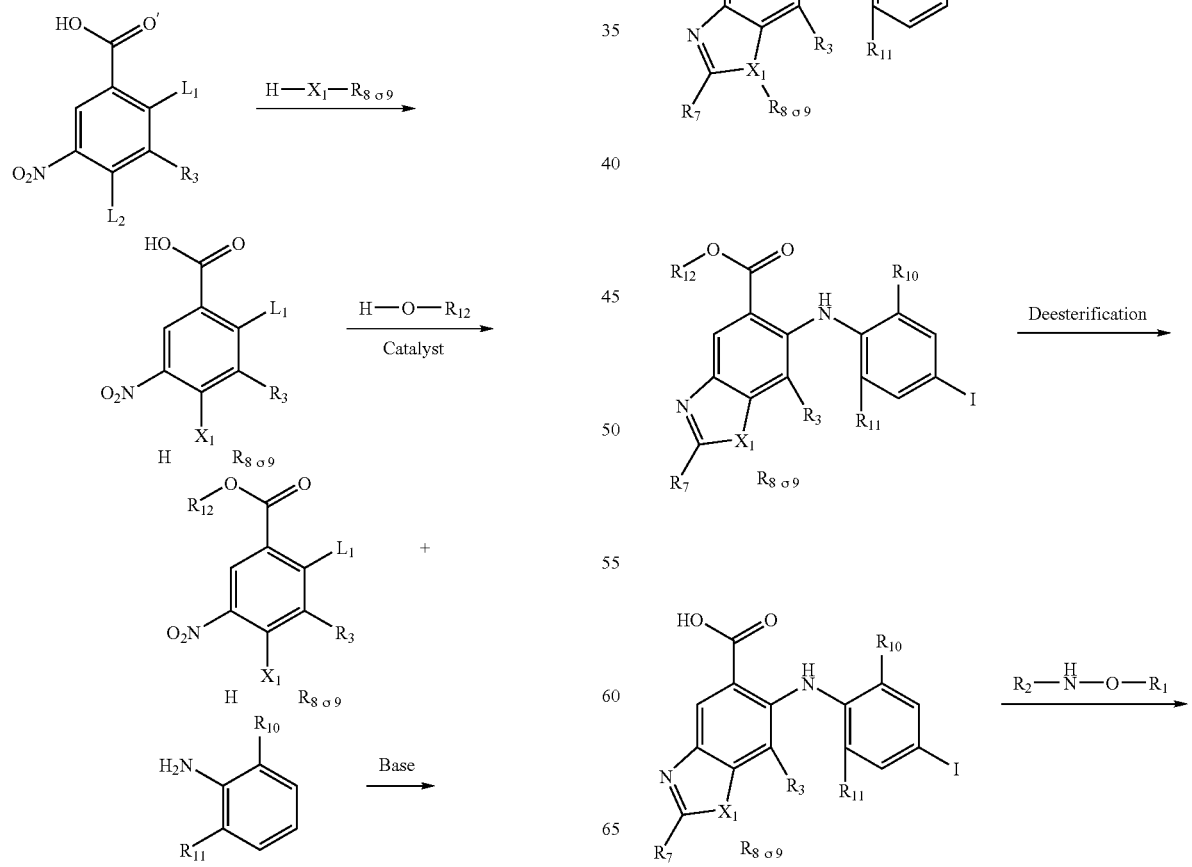

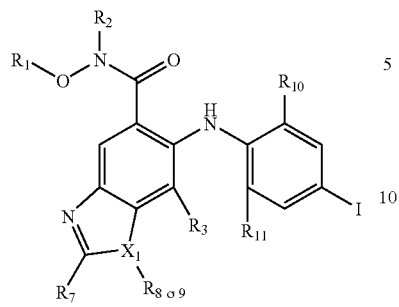
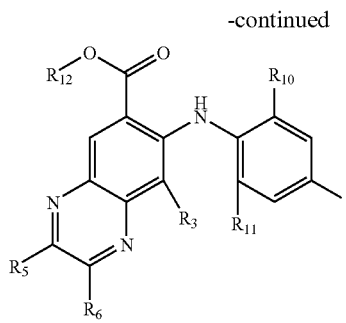
Scheme 2
Scheme 3
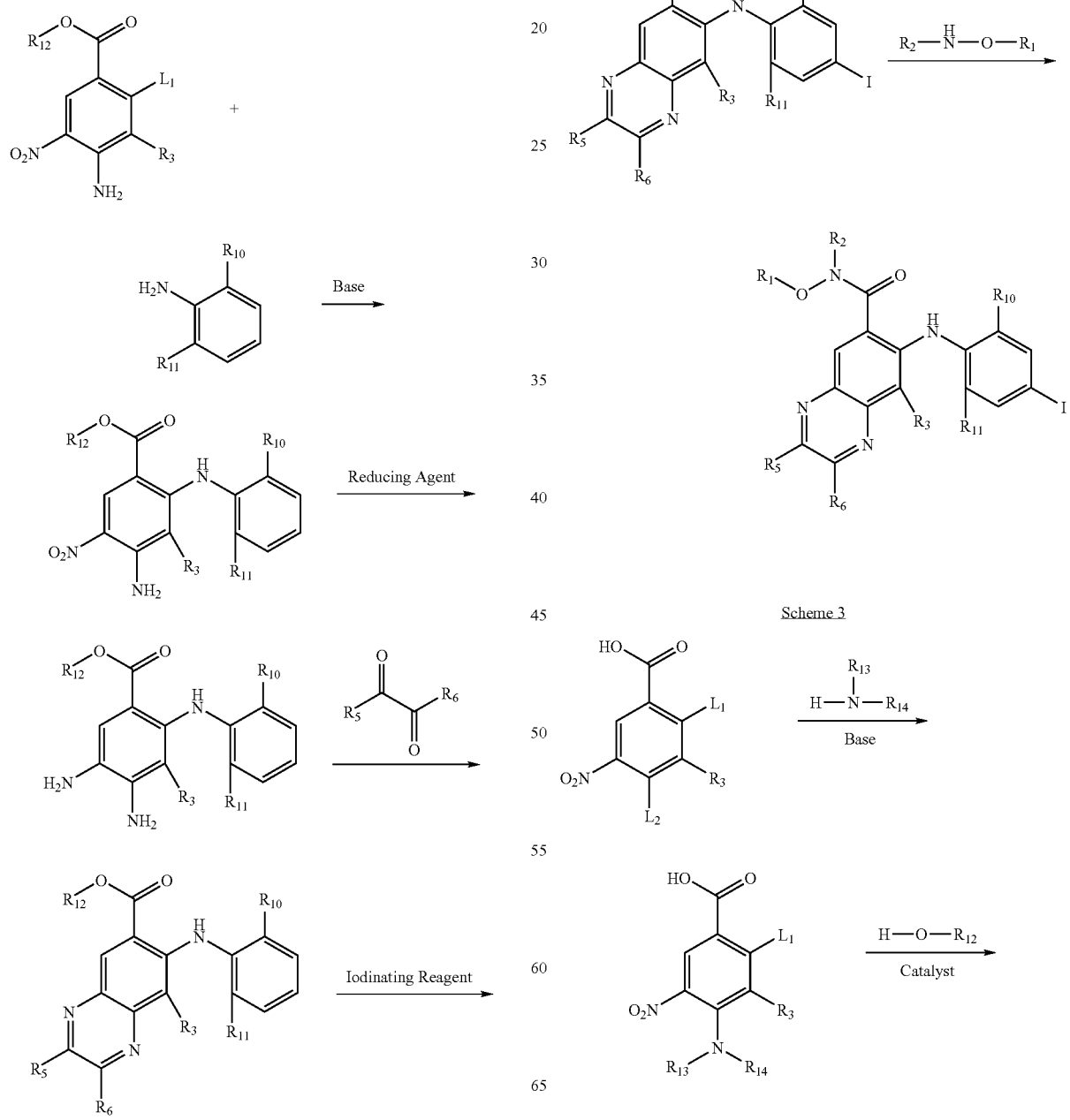

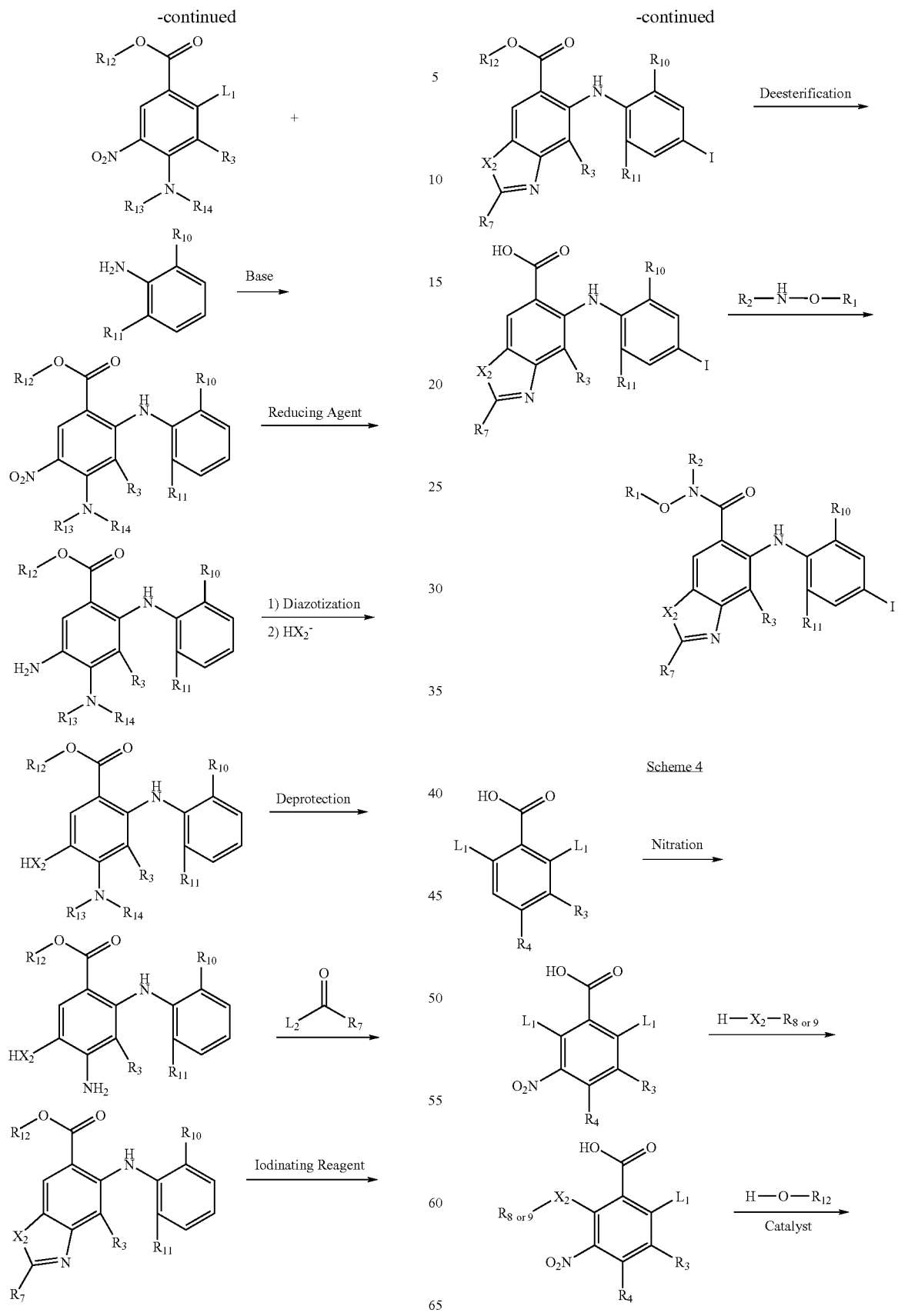

-continued
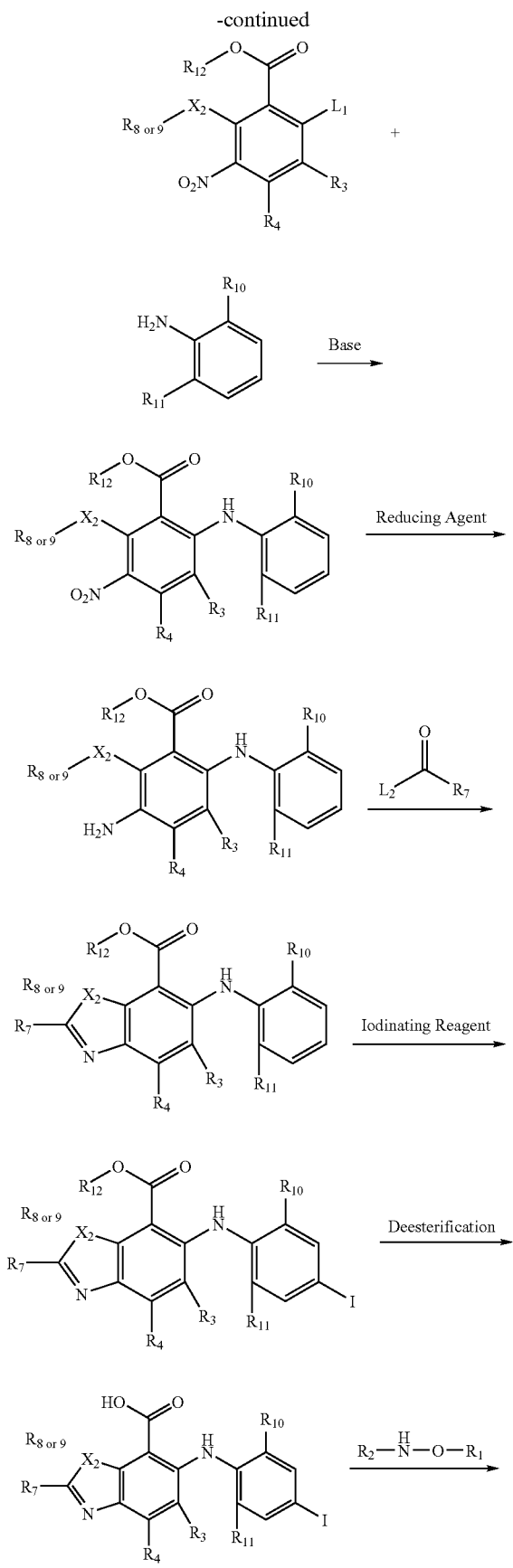
-continued
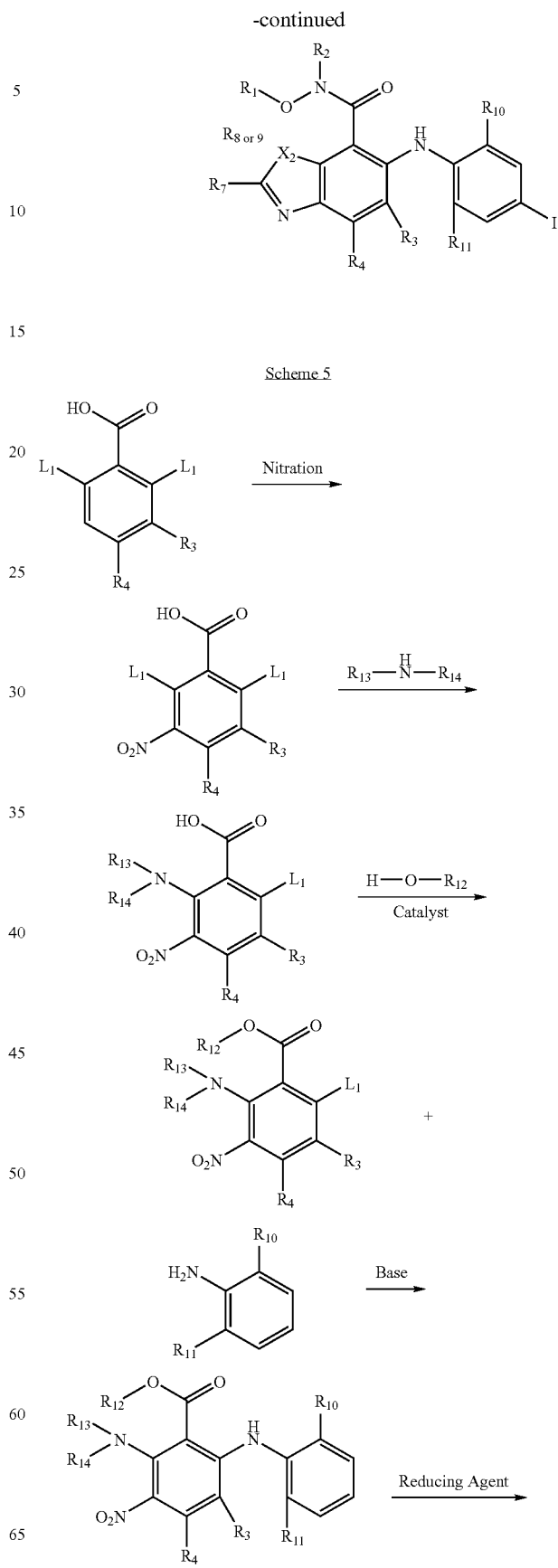
Scheme 5

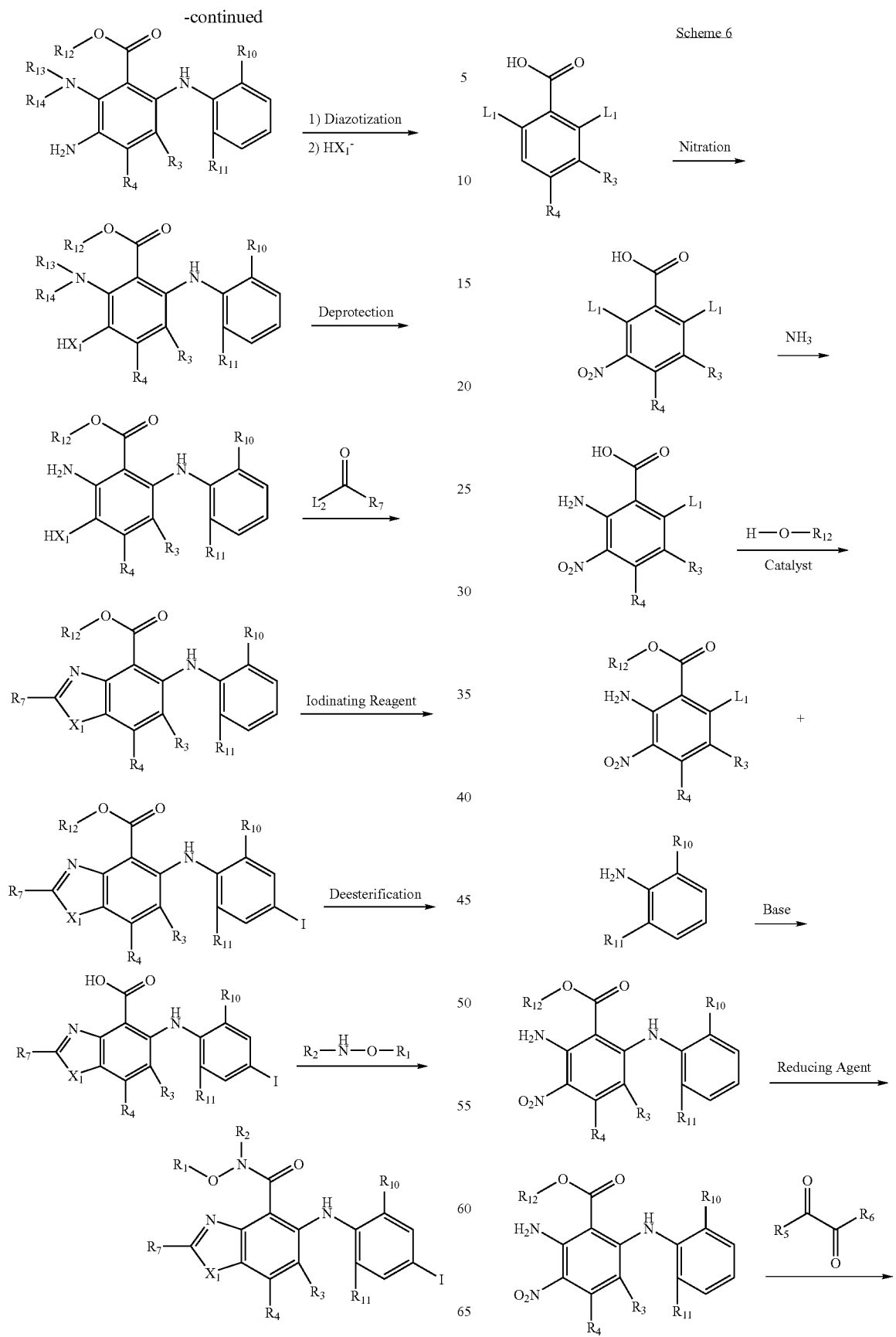

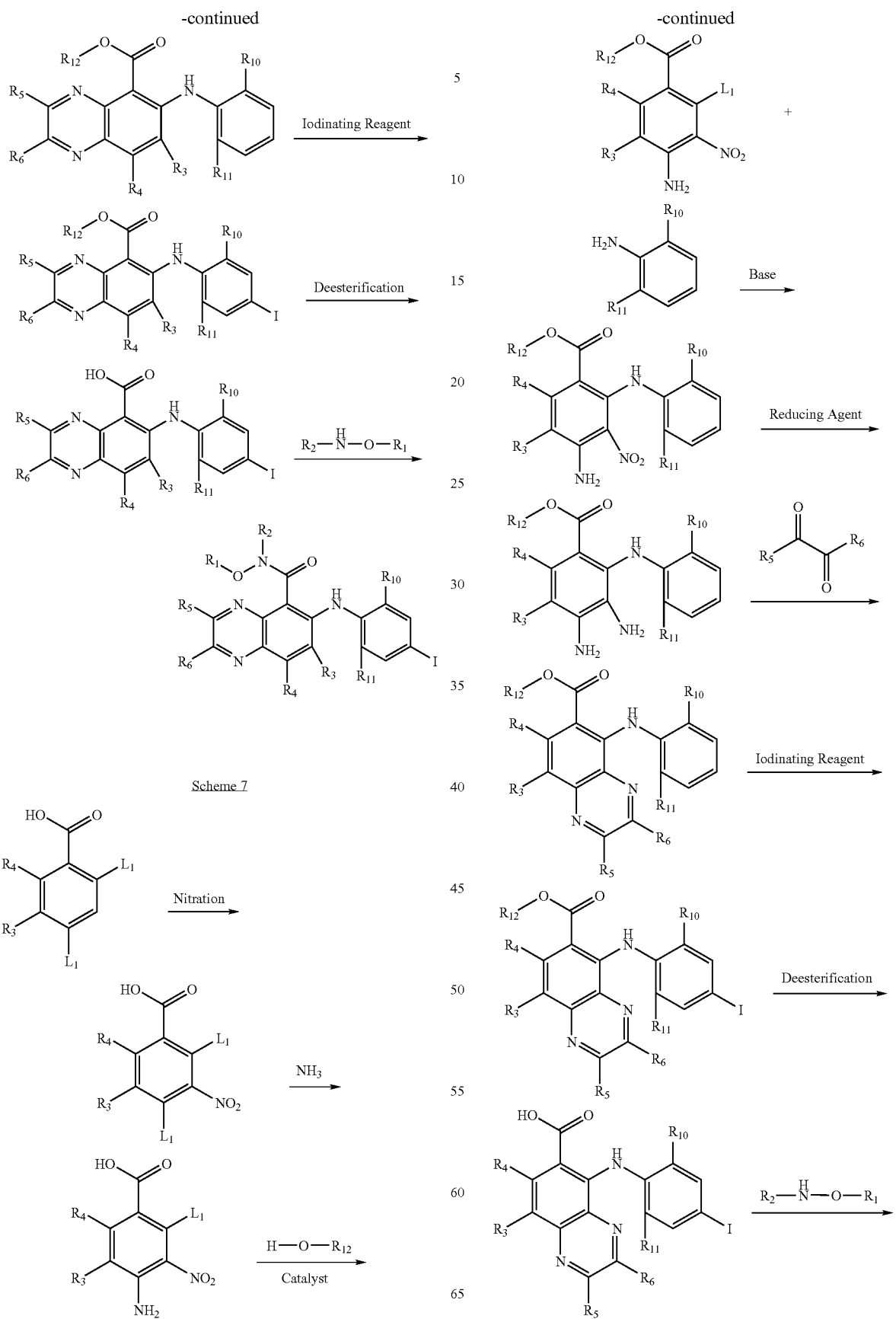

-continued
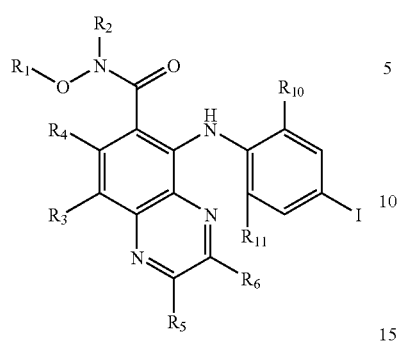
Scheme 8
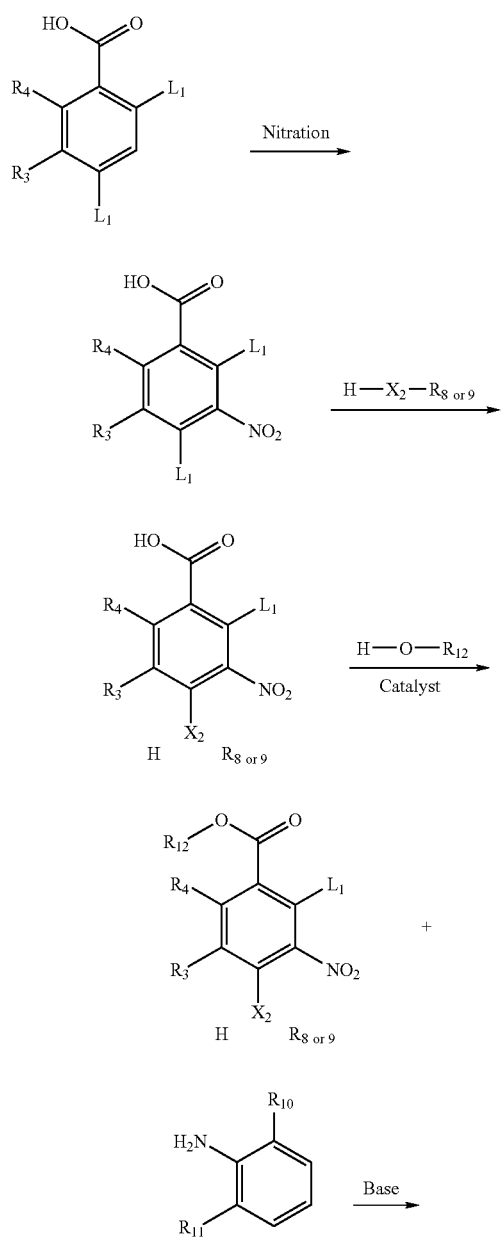
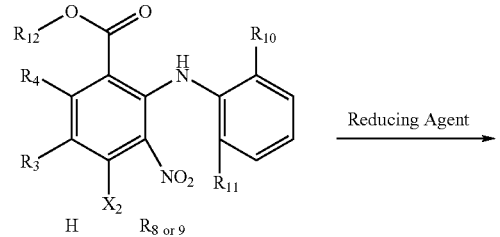
Reducing Agent →
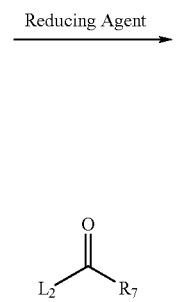
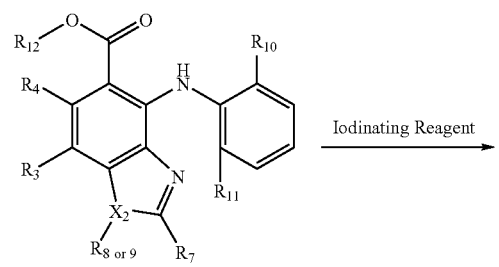
Iodinating Reagent →
Deesterification →

Scheme 9
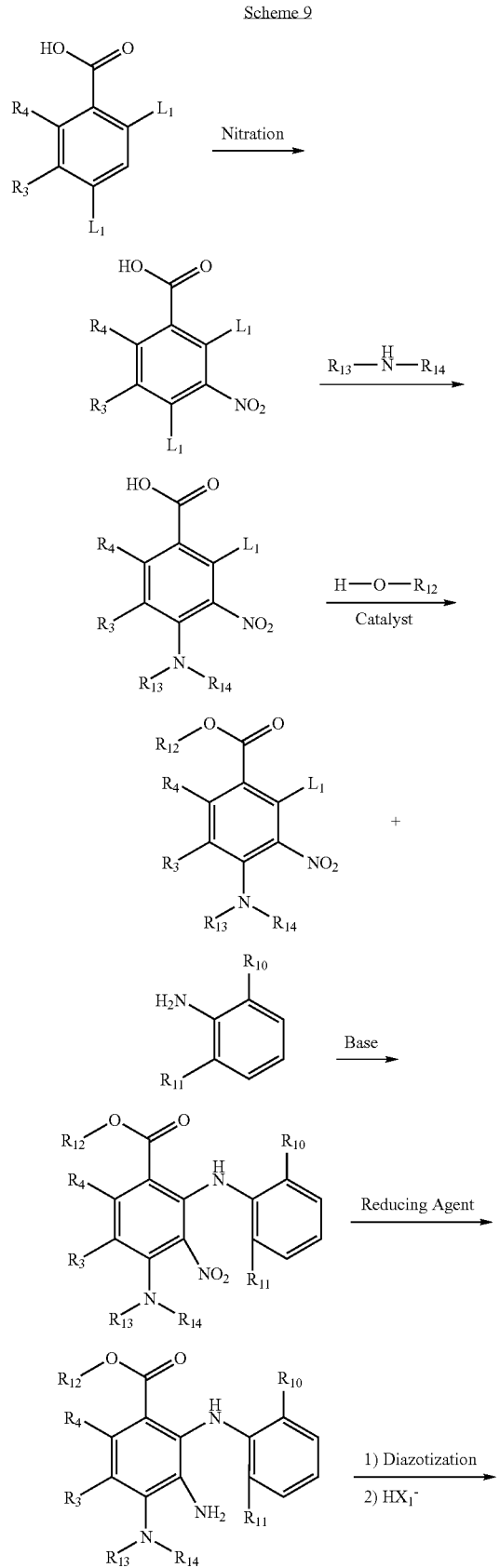
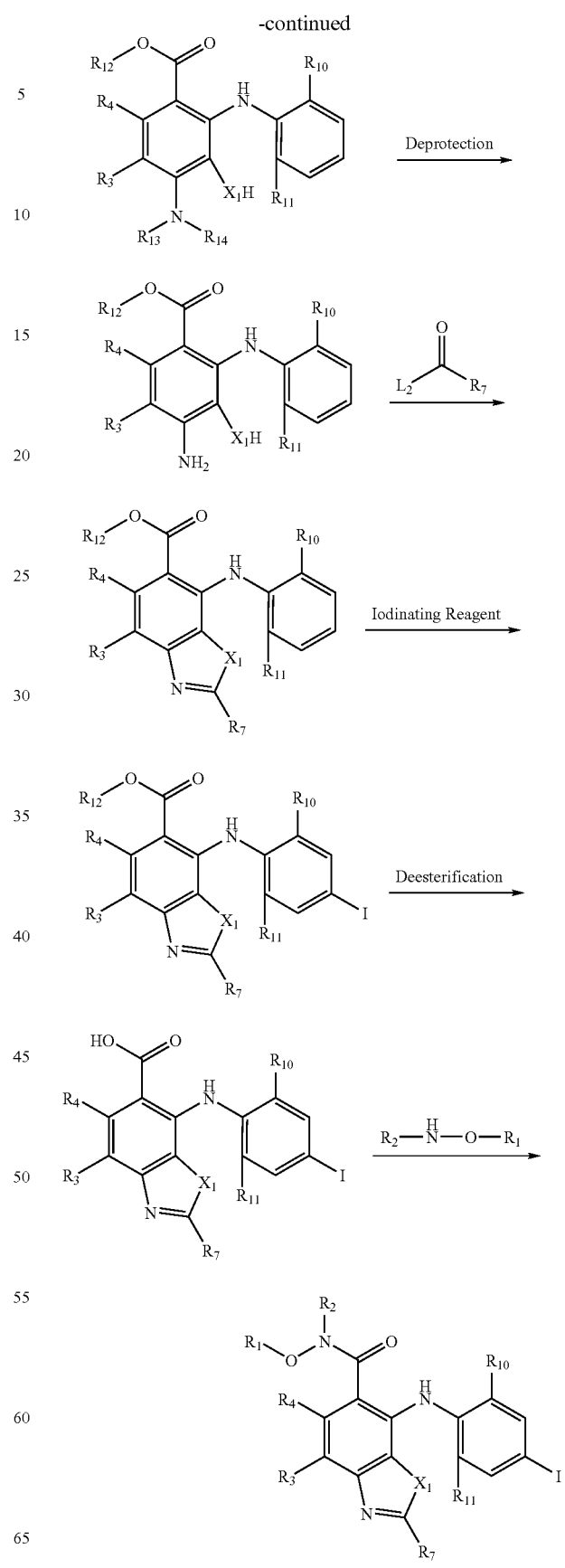

Scheme 10
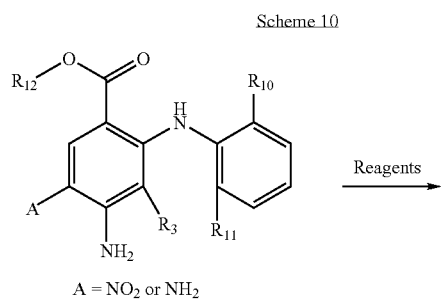
A = NO₂ or NH₂
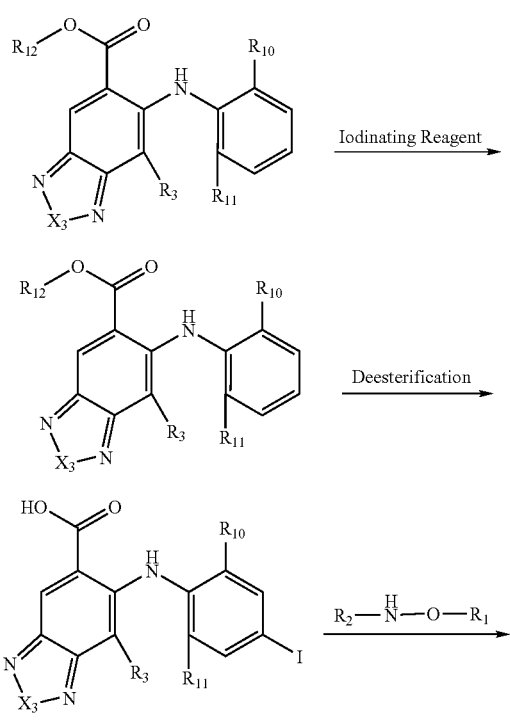
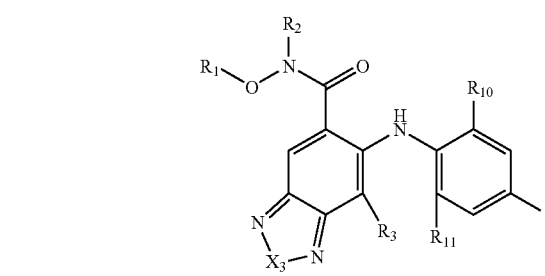
Scheme 11
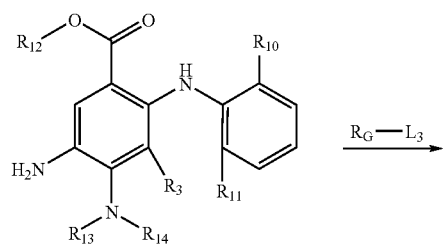
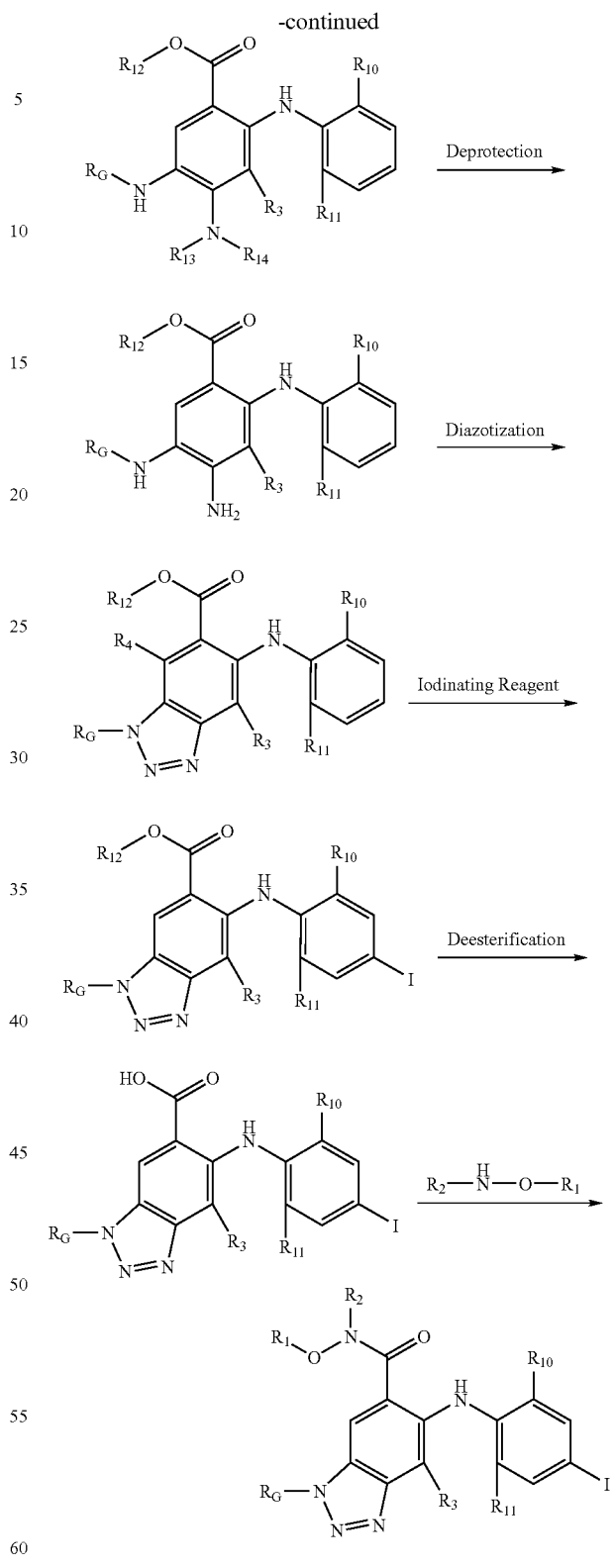
D. Uses
The disclosed compositions are useful as both prophylactic and therapeutic treatments for diseases or conditions relating to chronic pain, including neuropathic pain, as provided in the Summary section, as well as diseases or conditions modulated by the MEK cascade. For example, in one embodiment, the disclosed method relates to postoperative pain, phantom limb pain, burn pain, gout, trigeminal neuralgia, acute herpetic and postherpetic pain, causalgia, diabetic neuropathy, plexus avulsion, neuroma, vasculitis, crush injury, constriction injury, tissue injury, post-surgical pain, arthritis pain, or limb amputation For example, local injuries can be treated with local or topical administration. Chronic pain affecting the entire body, such as diabetic neuropathy can be treated with systemic administration (injection or orally) of a disclosed composition. Treatment for chronic pain (e.g., post-operative pain) confined to the lower body can be administered centrally, e.g., epidurally. Formulations and methods of administration can include the use of more than one MEK inhibitor, or a combination of a MEK inhibitor and another pharmaceutical agent, such as an anti-inflammatory, analgesic, muscle relaxing, or anti-infective agent. Preferred routes of administration are oral, intrathecal or epidural, subcutaneous, intravenous, intramuscular, and, for non-human mammals, intraplantar, and are preferably epidural.

1. Dosages

Those skilled in the art will be able to determine, according to known methods, the appropriate dosage for a patient, taking into account factors such as age, weight, general health, the type of pain requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight. Commercially available capsules or other formulations (such as liquids and film-coated tablets) of 100 mg, 200 mg, 300 mg, or 400 mg can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Related Compounds

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$alkyl, cycloalkyl, aryl, heteroaryl, or non-aromatic heterocyclic), amino acid addition salts, esters, and amides which are within a reasonable benefit/risk ratio, pharmacologically effective, and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See, for example, S. M. Berge, et al., "Pharmaceutical Salts," *J. Pharm. Sci.,* 1977, 66:1–19 which is incorporated herein by reference. Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters.

The invention also includes disclosed compounds having one or more functional groups (e.g., hydroxyl, amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Hydroxyl protecting groups include: ethers, esters, and protection for 1,2- and 1,3-diols. The ether protecting groups include: methyl, substituted methyl ethers, substituted ethyl esters, substituted benzyl ethers, silyl ethers and conversion of silyl ethers to other functional groups.

Substituted Methyl Ethers

Substituted methyl ethers include: methoxymethyl, methylthiomethyl, t-utylthiomethyl, (phenyldimethylsilyl)methoxymethyl, benzyloxymethyl, p-ethoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydro-pyranyl, tetrahydrothiopyranyl, 1-methoxycyclohexyl, 4-methoxytetrahydropyranyl, 4-methoxytetrahydrothio-pyranyl, 4-methoxytetrahydrothiopyranyl S,S-dioxido, 1-[(2-chloro-4-methyl) phenyl]-4-methoxypiperidin-4-yl, 1,4-dioxan-2-yl, tetrahydrofuranyl, tetrahydrothiofuranyl, and 2,3,3a,4,5,6,7,7a-octahydro-7,8,8-trimethyl-4,7-ethanobenzofuran-2-yl.

Substituted Ethyl Ethers

Substituted ethyl ethers include: 1-ethoxyethyl, 1-(2,chloroethoxy)ethyl, 1-methyl-1-methoxyethyl, 1-methyl-1-benzyloxyethyl, 1-methyl-1-benzyloxy-2-fluoroethyl, 2,2,2- trichloroethyl, 2-trimethylsilyethyl, 2-(phenylselenyl)ethyl, t-butyl, allyl, p-chlorophenyl, p-methoxyphenyl, 2,4-dinitrophenyl, and benzyl.

Substituted Benzyl Ethers

Substituted benzyl ethers include: p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri-(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"tris(benzoyloxyphenyl)methyl, 3-(imidazol-1-ylmethyl)bis(4',4"-dimethoxyphenyl)-methyl, 1,1-bis(4 -methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Silyl ethers include: trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl tri-p-xylylsilyl, triphenylsilyl, diphenylmethylsilyl, and t-butylmethoxyphenylsilyl.

Esters

Esters protecting groups include: esters, carbonates, assisted cleavage, miscellaneous esters, and sulfonates.

Esters

Examples of protective esters include: formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivoloate, adamantoate,crotonate,4-methoxycrotonate, benzoate, p-phenylbenzoate, and 2,4,6-trimethylbenzoate(mesitoate).

Carbonates

Carbonates include: methyl, 9-fluorenylmethyl, ethyl, 2,2, 2-trichloroethyl, 2-(trimethylsilyl)ethyl, 2-(phenylsulfonyl) ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage protecting groups include: 2-iodobenzoate, 4-azido-butyrate, 4-nitro-4-methylpentanoate, o-(dibromomethyl)benzoate, 2-formylbenzene-sulfonate, 2-(methylthiomethoxy)ethyl carbonate, 4-(methylthiomethoxymethyl)benzoate, and 2-(methylthiomethoxymethyl)benzoate.

Miscellaneous Esters

In addition to the above classes, miscellaneous esters include: 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N'N'-tetramethylphosphorodiamidate, N-phenylcarbamate, borate, dimethylphosphinothioyl, and 2,4-dinitrophenylsulfenate.

Sulfonates

Protective sulfates includes: sulfate, methanesulfonate (mesylate), benzylsulfonate, and tosylate.

Protection for 1,2- and 1,3-Diols

The protection for 1,2 and 1,3-diols group includes: cyclic acetals and ketals, cyclic ortho esters, and silyl derivatives.

Cyclic Acetals and Ketals

Cyclic acetals and ketals include: methylene, ethylidene, 1-t-butylethylidene, 1-phenylethylidene, (4-methoxyphenyl)ethylidene, 2,2,2-trichloroethylidene, acetonide(isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Cyclic ortho esters include: methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Protection for the Carboxyl Group Esters

Ester protecting groups include: esters, substituted methyl esters, 2-substituted ethyl esters, substituted benzyl esters, silyl esters, activated esters, miscellaneous derivatives, and stannyl esters.

Substituted Methyl Esters

Substituted methyl esters include: 9-fluorenylmethyl, methoxymethyl, methylthiomethyl, tetrahydropyranyl, tetrahydrofuranyl, methoxyethoxymethyl, 2-(trimethylsilyl) ethoxy-methyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

2-Substituted ethyl esters include: 2,2,2-trichloroethyl, 2-haloethyl, α-chloroalkyl, 2-(trimethylsilyl)ethyl, 2-methylthioethyl, 1,3-dithianyl-2-methyl, 2-(p-nitrophenylsulfenyl)-ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsily)-2-buten-1-yl, cinnamyl, α-methylcinnamyl, phenyl, p-(methylmercapto)-phenyl, and benzyl.

Substituted Benzyl Esters

Substituted benzyl esters include: triphenylmethyl, diphenylmethyl, bis(o-nitrophenyl)methyl, 9-anthrylmethyl, 2-(9, 10-dioxo)anthrylmethyl, 5-dibenzo-suberyl, 1-pyrenylmethyl,2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, and 4-P-benzyl.

Silyl Esters

Silyl esters include: trimethylsilyl, triethylsilyl, t-butyldimethylsilyl, i-propyldimethylsilyl, phenyldimethylsilyl, and di-t-butylmethylsilyl.

Miscellaneous Derivatives

Miscellaneous derivatives includes: oxazoles, 2-alkyl-1, 3-oxazolines, 4-alkyl-5-oxo-1,3-oxazolidines, 5-alkyl-4-oxo-1,3-dioxolanes, ortho esters, phenyl group, and pentaaminocobalt(III) complex.

Stannyl Esters

Examples of stannyl esters include: triethylstannyl and tri-n-butylstannyl.

Amides and Hydrazides

Amides include: N,N-dimethyl, pyrrolidinyl, piperidinyl, 5,6-dihydrophenanthridinyl, o-nitroanilides, N-7-nitroindolyl, N-8-nitro-1,2,3,4-tetrahydroquinolyl, and p-P-benzenesulfonamides. Hydrazides include: N-phenyl, N,N'-diisopropyl and other dialkyl hydrazides.

Protection for the Amino Group

Carbamates

Carbamates include: carbamates, substituted ethyl, assisted cleavage, photolytic cleavage, urea-type derivatives, and miscellaneous carbamates.

Carbamates

Carbamates include: methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydro-thioxanthyl)]methyl, and 4-methoxyphenacyl.

Substituted Ethyl

Substituted ethyl protective groups include: 2,2,2-trichloroethyl, 2-trimethylsilylethyl, 2-phenylethyl, 1-(1-adamantyl)-1-methylethyl, 1,1-dimethyl-2-haloethyl, 1,1dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'-and 4'-pyridyl)ethyl, 2-(N,N-icyclohexylcarboxamido)-ethyl, t-butyl, 1-adamantyl, vinyl, allyl, 1-isopropylallyl, connamyl, 4-nitrocinnamyl, quinolyl, N-hydroxypiperidinyl, alkyldithio, benzyl, p-methoxybenzyl, p-nitrobenzyl, p-bromobenzyl, p-chlorobenzyl, 2,4dichlorobenzyl, 4-methylsulfinylenzyl, 9-anthrylmethyl, and diphenylmethyl.

Assisted Cleavage

Protection via assisted cleavage includes: 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2cyanoethyl, m-chloro-p-acyloxybenzyl, p-(dihydroxyboryl)benzyl, 5-benzisoxazolyl-methyl, and 2-(trifluoromethyl)-6-chromonylmethyl.

Photolytic Cleavage

Photolytic cleavage methods use groups such as: m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of of urea-type derivatives includes: phenothiazinyl-(10)-carbonyl derivative, N'-p-toluenesulfonylaminocarbonyl, and N'-phenylaminothiocarbonyl.

Miscellaneous Carbamates

In addition to the above, miscellaneous carbamates include: t-amyl, S-benzyl thiocarbamate, p-cyanobenzyl, cyclobutyl, cyclohexyl, cyclopentyl, cyclopropylmethyl, p-decyloxy-benzyl, diisopropylmethyl, 2,2-dimethoxycarbonylvinyl, o-(N,N-dimethyl-carboxamido)-benzyl, 1,1-dimethyl-3(N,N-dimethylcarboxamido)propyl, 1,1-dimethyl-propynyl, di(2-pyridyl)methyl, 2-furanylmethyl, 2-iodoethyl, isobornyl, isobutyl, isonicotinyl, p(p'-methoxyphenyl-azo)benzyl, 1-methylcyclobutyl, 1-methylcyclohexyl, 1-methyl-1-cyclopropyl-methyl, 1-methyl-(3,5-dimethoxyphenyl)ethyl, 1-methyl-1(p-henylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Amides

Amides

Amides includes: N-formyl, N-acetyl, N-chloroacetyl, N-trichloroacetyl, N-trifluoroacetyl, N-phenylacetyl, N-3-phenylpropionyl, N-picolinoyl, N-3-pyridyl-carboxamide, N-benzoylphenylalanyl derivative, N-benzoyl, and N-p-phenylbenzoyl.

Assisted Cleavage

Assisted cleavage groups include: N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy) propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

Cyclic imide derivatives include: N-phthalimide, N-dithiasuccinoyl, N-2,3-diphenyl-maleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special —NH Protective Groups

Protective groups for —NH include: N-alkyl and N-aryl amines, imine derivatives, enamine derivatives, and N-hetero atom derivatives (such as N-metal, N-N, N-P, N-Si, and N-S), N-sulfenyl, and N-sulfonyl.

N-Alkyl and N-Aryl Amines

N-alkyl and N-aryl amines include: N-methyl, N-allyl, N-[2-(trimethylsilyl)ethoxyl]-methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

Imine derivatives include: N-1,1-dimethylthiomethylene, N-benzylidene, N-p-methoxybenzylidene, N-diphenylmethylene, N-[(2-pyridyl)mesityl]methylene, N-(N',N'-dimethylaminomethylene), N,N'-isopropylidene, N-p-nitrobenzylidene, N-salicylidene, N-5-chlorosalicylidene, N-(5-chloro-2-hydroxyphenyl)phenylmethylene, and N-cyclohexylidene.

Enamine Derivative

An example of an enamine derivative is N-(5,5-dimethyl-3-oxo-1-cyclohexenyl).

N-Hetero Atom Derivatives

N-metal derivatives include: N-borane derivatives, N-diphenylborinic acid derivative, N-[phenyl(pentacarbonylchromium- or -tungsten)]carbenyl, and N-copper or N-zinc chelate. Examples of N-N derivatives include: N-nitro, N-nitroso, and N-oxide. Examples of N-P derivatives include: N-diphenylphosphinyl, N-dimethylthiophosphinyl, N-diphenylthiophosphinyl, N-dialkyl phosphoryl, N-dibenzyl phosphoryl, and N-diphenyl phosphoryl. Examples of N-sulfenyl derivatives include: N-benzenesulfenyl, N-o-nitrobenzenesulfenyl, N-2,4-dinitrobenzenesulfenyl, N-pentachlorobenzenesulfenyl, N-2-nitro-4-methoxy-benzenesulfenyl, N-triphenylmethylsulfenyl, and N-3-nitropyridinesulfenyl. N-sulfonyl derivatives include: N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzene-sulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilylethanesulfonyl, N-9-anthracenesulfonyl, N-4-(4',8'-dimethoxynaphthylmethyl)-benzenesulfonyl, N-benzylsulfonyl, N-trifluoromethylsulfonyl, and N-phenacylsulfonyl.

Disclosed compounds which are masked or protected may be prodrugs, compounds metabolized or otherwise transformed in vivo to yield a disclosed compound, e.g., transiently during metabolism. This transformation may be a hydrolysis or oxidation which results from contact with a bodily fluid such as blood, or the action of acids, or liver, gastrointestinal, or other enzymes.

Features of the invention are further described in the examples below.

E. Examples

BIOLOGICAL EXAMPLES

Example 1

Effect of PD 198306 on Streptozocin-Induced Static Allodynia

Animals

Male Sprague Dawley rats (250–300 g), obtained from Bantin and Kingman, (Hull, U.K.) were housed in groups of 3. All animals were kept under a 12 h light/dark cycle (lights on at 07 h 00 min) with food and water ad libitum. All experiments were carried out by an observer blind to drug treatments.

Development of Diabetes in the Rat

Diabetes was induced in rats by a single i.p. injection of streptozocin (50 mg/kg) as described previously (Courteix et al., 1993).

Evaluation of Static Allodynia

Mechanical hypersensitivity was measured using Semmes-Weinstein von Frey hairs (Stoelting, Ill., U.S.A.). Animals were placed into wire mesh bottom cages allowing access to the underside of their paws. Animals were habituated to this environment prior to the start of the experiment. Mechanical hypersensitivity was tested by touching the plantar surface of the animals right hind paw with von Frey hairs in ascending order of force (0.7, 1.2, 1.5, 2, 3.6, 5.5, 8.5, 11.8, 15.1 and 29 g) for up to 6 sec. Once a withdrawal response was established, the paw was re-tested, starting with the next descending von Frey hair until no response occurred. The highest force of 29 g lifted the paw as well as eliciting a response, thus represented the cut off point. The lowest amount of force required to elicit a response was recorded as the paw withdrawal threshold (PWT) in grams.

Drugs

PD 198306 [N-Cyclopropylmethoxy-3,4,5-trifluoro-2-(4-iodo-2-methyl-phenylamino)-benzamide] and Cl-1008 (pregabalin) were synthesized at Parke-Davis (Ann Arbor, Mich., USA). PD 198306 was suspended in cremophor:ethanol:water (1:1:8) vehicle. Pregabalin was dissolved in water. Both compounds were administered orally. Streptozocin (Aldrich, UK) was dissolved in 0.9% w/v NaCl and administered intraperitoneally. Drug administrations were made in a volume of 1 ml/kg.

Statistics

The static allodynia data were analysed using a Kruskall-Wallis ANOVA for non-parametric results, followed when significant by Mann-Whitney's t test.

Experimental Protocol

Static allodynia was assessed with von Frey hairs, before (baseline, BL) and 1 h after oral administration of PD 198306 (30 mg/kg, p.o.), vehicle (cremophor:ethanol:water, 1:1:8) or pregabalin (30 mg/kg, p.o.) (test). Animals were administered again the same compounds on the following day, both in the morning and the afternoon. Static allodynia was assessed only before and 1 h after the afternoon administration, in order to minimise the habituation of the animals to the testing conditions. Animals treated with pregabalin received water in the morning administration, in order to avoid the potential development of tolerance to the compound with repeated administration.

| Day 1: | Day 2: |
|---|---|
| | a.m.: PD 198306 |
| | Water |
| | Vehicle |
| p.m.: BL | p.m.: BL |
| PD 198306 | PD 198306 |
| Pregabalin | Pregabalin |
| Vehicle | Vehicle |
| Test | Test |

Results

A single administration of pregabalin (30 mg/kg, p.o.) significantly blocked streptozocin-induced static allodynia 1 h after administration. In contrast, a single administration of PD 198306 (30 mg/kg, p.o) had no effect on streptozocin-induced static allodynia 1 h after administration (see below). However, after the compound had been administered twice more on the following day, it significantly blocked streptozocin-induced static allodynia 1 h after the third administration. The effects had disappeared by the following day (see FIG. 1).

Example 2

Materials and Methods

Animals

Male Sprague Dawley rats (250–300 g), obtained from Charles River, Margate, U.K.) were housed in groups of 3–6. All animals were kept under a 12 h light/dark cycle (lights on at 07 h 00 min) with food and water ad libitum. All experiments were carried out by an observer blind to drug treatments.

Diabetes was induced in rats by a single i.p. injection of streptozocin (50 mg/kg) as described previously (Courteix et al., 1993).

Development of Chronic Constriction Injury in the Rat

Animals were anaesthetised with 2% isoflurane 1:4 $O_2/N_2O$ mixture maintained during surgery via a nose cone. The sciatic nerve was ligated as previously described by Bennett and Xie, 1988. Animals were placed on a homeothermic blanket for the duration of the procedure. After surgical preparation the common sciatic nerve was exposed at the middle of the thigh by blunt dissection through biceps femoris. Proximal to the sciatic trifurcation, about 7 mm of nerve was freed of adhering tissue and 4 ligatures (4-0 silk) were tied loosely around it with about 1 mm spacing. The incision was closed in layers and the wound treated with topical antibiotics.

Intrathecal Injections

PD 198306 and pregabalin were administered intrathecally in a volume of 10 μl using a 100 μl Hamilton syringe by exposing the spine of the rats under brief isoflurane anaesthesia. Injections were made into the intrathecal space between lumbar region 5–6 with a 10 mm long 27 gauge needle. Penetrations were judged successful if there was a tail flick response. The wound was sealed with an autoclip and rats appeared fully awake within 2–3 min following injection.

Evaluation of Static Allodynia

Mechanical hypersensitivity was measured using Semmes-Weinstein von Frey hairs (Stoelting, Ill., U.S.A.). Animals were placed into wire mesh bottom cages allowing access to the underside of their paws. Animals were habituated to this environment prior to the start of the experiment. Mechanical hypersensitivity was tested by touching the plantar surface of the animals right hind paw with von Frey hairs in ascending order of force (0.7, 1.2, 1.5, 2, 3.6, 5.5, 8.5, 11.8, 15.1 and 29 g) for up to 6 sec. Once a withdrawal response was established, the paw was re-tested, starting with the next descending von Frey hair until no response occurred. The highest force of 29 g lifted the paw as well as eliciting a response, thus represented the cut off point. The lowest amount of force required to elicit a response was recorded as the paw withdrawal threshold (PWT) in grams.

Experimental Protocol

Static allodynia was assessed with von Frey hairs, before (baseline, BL) and 0.5 h, 1 h and 2 h after intrathecal or intraplantar administration of PD 198306 (1–30 μg, i.t.), vehicle (cremophor:ethanol:water, 1:1:8) or pregabalin (10 μg, i.t.). For oral administration experiments, static allodynia was assessed with von Frey hairs, before (baseline, BL) and 1 h after oral administration of PD 198306 (3–30 mg/kg, p.o.), vehicle (cremophor:ethanol:water, 1:1:8) or pregabalin (30 mg/kg, p.o.). Animals were administered again the same compounds on the following day, both in the morning and the afternoon. Static allodynia was assessed before and 1 h after the morning administration. In the afternoon static allodynia was assessed before, 1 h, 2 h and 3 h after administration for streptozocin treated animals. CCI animals were assessed before, 1 h and 2 h after administration Drugs Used PD 198306 and pregabalin were synthesised at Parke-Davis (Ann Arbor, Mich., USA). PD 198306 was suspended in cremophor:ethanol:water (1:1:8) vehicle. Pregabalin was dissolved in water. Both compounds were administered orally, intrathecally or intraplantar in volumes of 1 ml/kg, 10 μl and 100 μl respectively. Streptozocin (Aldrich, UK) was dissolved in 0.9% w/v NaCl and administered intraperitoneally in a volume of 1 ml/kg.

Statistics

Data were analysed using a Kruskall-Wallis ANOVA for non-parametric results, followed when significant by Mann-Whitney's t test vs vehicle group.

Results

1. Effects of PD 198306 on Static Allodynia, Following Systemic Administration 1.1. Effect of PD 198306 on Streptozocin-Induced Static Allodynia A single administration of pregabalin (30 mg/kg, p.o.) significantly blocked streptozocin-induced static allodynia 1 h after administration. In contrast, a single administration of PD 198306 (3–30 mg/kg, p.o) had no effect on streptozocin-induced static allodynia 1 h after administration (FIG. 2). However, after the compound had been administered twice more on the following day, PD 198306 (30 mg/kg) significantly blocked streptozocin-induced static allodynia for 2 h after the third administration (FIG. 2).

1.2. Effect of PD198306 on CCI-Induced Static Allodynia

A single administration of pregabalin (30 mg/kg, p.o.) significantly blocked CCI-induced static allodynia 1 h after administration. In contrast, neither a single or multiple administration of PD 198306 (3–30 mg/kg, p.o) had any effect on CCI-induced static allodynia (FIG. 3).

2. Effects of PD 198306 on Static Allodynia, Following Intrathecal Administration Intrathecally administered PD 198306 (1–30 μg) dose-dependently blocked the maintenance of static allodynia in both streptozocin (FIG. 4) and CCI animals (FIG. 5) with respective MEDs of 3 and 10 μg. This antiallodynic effect lasted for 1 h.

3. Effects of PD 198306 on Static Allodynia, Following Intraplantar Administration An intrathecal administration of PD 198306 (30 μg) significantly blocked static allodynia in both neuropathic pain models (FIGS. 6,7). In contrast, a single administration of PD 198306 at a dose 100-fold higher (3 mg/100 μl) directly into the paw had no effect on streptozocin (FIG. 6) or CCI-induced static allodynia (FIG. 7).

References

Bennett G J, Xie Y-K. A peripheral mononeuropathy in rat that produces disorders of pain sensation like those seen in man. Pain 1988;33:87–107.

Courteix C, Eschalier A and Lavarenne J. Streptozocin-induced rats: behavioural evidence for a model of chronic pain. Pain 1993;53:81–8

Example 3

Effect of Other MEK Inhibitors in a Neuropathic Pain Model in the Rat

Summary

The effect of several MEK inhibitors, with different binding affinities, has been investigated in the CCI model of neuropathic pain in the rat, by assessing static allodynia with von Frey hairs. Intrathecal administration of PD219622 or PD297447 (30 μg) had no significant effect on allodynia. This lack of effect may reflect the low affinity or solubility of the compounds. However, intrathecal administration of PD 254552 or PD 184352 (30 μg), which posses higher binding affinities, blocked the maintenance of static allodynia in CCI animals. The antiallodynic affect was only evident for 30 min post-injection and thus, shorter than the one observed for pregabalin (100 μg). The magnitude of the effect was similar for 30 μg of PD 184352 and 100 μg of pregabalin. From this study it is concluded that MEK inhibitors exert an antiallodynic effect in CCI-induced neuropathic rats when administered intrathecally, and that the antiallodynic effect correlates with the affinity of the compounds.

The animals and methods for developing chronic constriction injury in the rat, injecting test compounds, and evaluation of static allodynia were according to Example 2 above. PD219622, PD297447, PD 184352, PD 254552 and pregabalin were administered intrathecally at doses of 30 μg for all PD compounds and 100 μg for pregabalin. Static allodynia was assessed with von Frey hairs, before (baseline, BL) and 0.5 h, 1 h and 2 h after intrathecal administration of the compounds Drugs Used PD297447, PD219622, PD 254552, PD 184352 (CI-1040), and pregabalin were synthesised at Parke-Davis (Ann Arbor, Mich., USA). PD297447, PD219622, PD 254552 and PD 184352 were suspended in cremophor:ethanol:water (1:1:8) vehicle. Pregabalin was dissolved in water. All compounds were administered intrathecally in a 10 μl volume.

Statistics

Data were analysed using a Kruskall-Wallis ANOVA for non-parametric results, followed when significant by Mann-Whitney's t test vs vehicle group.

Results

Intrathecally administered PD297447 or PD219622 (30 μg) had no significant effect on allodynia. This lack of effect may reflect the low affinity of the compounds (965 nM and 100 nM respectively). However, intrathecal administration of PD 184352 or PD 254552 (30 μg) blocked the maintenance of static allodynia in CCI animals (see FIG. 8). These compounds possess higher affinity (2 and 5 nM respectively). The antiallodynic effect was only evident for 30 min post-injection and thus, shorter than the one observed for pregabalin (100 μg). The magnitude of the effect was similar for 30 μg of PD 184352 and 100 μg of pregabalin.

The results indicate that MEK inhibitors exert an antiallodynic effect in CCI-induced neuropathic rats when administered intrathecally, and that the antiallodynic effect correlates with the affinity of the compounds.

CHEMICAL EXAMPLES

Example 1

Preparation of 7-fluoro-6-(4-iodo-2-methyl-phenylamino)-1H-benzoimidazole-5-carboxylic acid (PD 205293)

(APK $IC_{50}$=14 nM; colon 26 cells, $IC_{50}$=>10 micromolar)

Step a: Preparation of 5-nitro-2,3,4-trifluorobenzoic acid

To gently stirring concentrated sulfuric acid (50 ml) was added fuming nitric acid (3.4 ml, 0.076 mol). Solid 2,3,4-trifluorobenzoic acid (10.00 g, 0.05565 mol) was added directly in increments. After stirring 45 minutes, the reaction mixture had become an orange homogeneous solution which was then poured over chilled water (400 ml). The resulting aqueous suspension was extracted with diethyl ether (3×200 ml). The combined extracts were dried with anhydrous magnesium sulfate and concentrated in vacuo to yield 12.30 g of a dull, light-yellow solid. Recrystallization from chloroform (50 ml) afforded 9.54 g of the pale yellow microcrystalline product; 78% yield; m.p.; $^1$H-NMR (400 MHz; DMSO) δ 14.29 (broad s, 1H), 8.43–8.38 (m, 1H); $^{13}$C-NMR (100 MHz; DMSO) δ 162.41, 154.24 (dd, $J_{C-F}$=270.1, 10.7 Hz), 148.35 (dd, $J_{C-F}$=267.0, 9.2 Hz), 141.23 (dt, $J_{C-F}$=253.4 Hz), 133.95, 123.30 (d, $J_{C-F}$=2.2 Hz), 116.92 (dd, $J_{C-F}$=18.2, 3.8 Hz); $^{19}$F-NMR (376 MHz; DMSO) δ −120.50 to −120.63 (m), −131.133 to −131.27 (m), −153.63 to −153.74 (m).

Step b: Preparation of 4-amino-2,3-difluoro-5-nitrobenzoic acid

Solid 5-nitro-2,3,4-trifluorobenzoic acid (0.75 g, 0.00339 mol) was dissolved in concentrated ammonium hydroxide (25 ml) to give instantly a yellow solution. A precipitate began to form within five minutes, after which time the mixture was acidified to pH 0 with concentrated aqueous hydrochloric acid. A yellow precipitate rapidly formed. The mixture was heated to boiling and was filtered hot. The yellow solids were washed with 10% aqueous hydrochloric acid and were suction dried to afford 0.47 g of a yellow powder; 64% yield; $^1$H-NMR (400 MHz; DMSO) δ 13.32 (s, 1H), 8.36 (d, 1H, J=7.6 Hz), 7.98 (s, 2H); $^{19}$F-NMR (376 MHz; DMSO) δ −128.69 to −128.76 (m), −153.60 (d).

Step c: Preparation of methyl 4-amino-2,3-difluoro-5-nitrobenzoate

Hydrogen chloride gas was dissolved in anhydrous methanol (30 ml) until the solution was warm. The solid 4-amino-2,3-difluoro-5-nitrobenzoic acid (0.47 g; 0.00215 mol) was dissolved in this solution and the reaction mixture was brought to reflux with vigorous stirring for 23 hours under a nitrogen atmosphere. The reaction mixture was allowed to cool slowly on the bench. A yellow precipitate formed and was collected by vacuum filtration and dried with suction to afford 0.35 g of yellow microfilaments; 70% yield; m.p. 183.5–184° C.; $^1$H-NMR (400 MHz; DMSO) δ 8.36 (dd, 1H, J=7.3, 1.7 Hz), 8.06 (s, 2H), 3.78 (s, 3H); $^{19}$F-NMR (376 MHz; DMSO) δ −128.85 to −128.92 (m), −153.29 (d); MS (APCl−) 231 (M−1, 100); IR (KBr) 3433, 3322, 1700, 1650, 1549, 1343, 1285 cm$^{-1}$; Anal. calcd/found for: $C_8H_6F_2N_2O_4$ C, 41.39/41.40; H, 2.61/2.50; N, 12.07/11.98; F, 16.37/16.58.

Step d: Preparation of methyl 4-amino-3-fluoro-2-(2-methyl-phenylamino)-5-nitrobenzoate The solid methyl 4-amino-2,3-difluoro-5-nitrobenzoate (0.087 g, 3.7×10$^{-4}$ mol) was dissolved in ortho-toluidine (3 ml, 0.028 mol). The reaction mixture was stirred at 200° C. for 35 minutes under a nitrogen atmosphere. The mixture was then partitioned between diethyl ether (150 ml) and 10% aqueous hydrochloric acid (150 ml). The ether phase was dried with anhydrous magnesium sulfate and was concentrated in vacuo to a crude solid. The crude product was dissolved in 5 ml of dichloromethane and was filtered through a flash silica plug. Elution with dichloromethane afforded 0.0953 g of a yellow solid; 81% yield; m.p. 164–168° C.; $^1$H-NMR (400 MHz; DMSO) δ 9.20 (s, 1H), 8.52 (d, 1H, J=1.7 Hz), 7.57 (s, 2H), 7.19 (d, 1H, J=7.3 Hz), 7.12–7.08 (m, 1H), 7.02–6.98 (m, 1H), 6.95–6.91 (m, 1H), 3.78 (s, 3H), 2.21 (s, 3H); $^{19}$F-NMR (376 MHz; DMSO) δ −141.13 (s); MS (APCl+) 320 (M+1, 100); (APCl−) 318 (M−1, 100); IR (KBr) 3467, 3346, 1690, 1305 cm$^{-1}$; Anal. calcd/found for: $C_{15}H_{14}FN_3O_4$·0.21 $H_2O$ C, 55.77/55.97; H, 4.50/4.55; N, 13.01/12.61; F, 5.88/5.95.

Step e: Preparation of methyl 4,5-diamino-3-fluoro-2-(2-methyl-phenylamino)benzoate To a mixture comprised of methyl 4-amino-3-fluoro-2-(2-methyl-phenylamino)-5-nitrobenzoate (2.52 g, 0.00789 mol), tetrahydrofuran (50 ml), methanol (50 ml) and washed Raney nickel (0.5 g) was initially applied 48.6 psi of hydrogen gas at 30.2° C. in a shaker for 4 hours 48 minutes. The mixture was filtered and the filtrate concentrated in vacuo to afford 2.20 g of a salmon-colored amorphous solid; 96% yield; $^1$H-NMR (400 MHz; DMSO) δ 7.84 (s, 1H), 7.04 (d, 1H, J=7.1 Hz), 6.98 (d, 1H, J=1.2 Hz), 6.95–6.91 (m, 1H), 6.68–6.64 (m, 1H), 6.40–6.36 (m, 1H), 5.39 (s, 2H), 4.73 (s 2H), 3.66 (s, 3H), 2.21 (s, 3H); $^{19}$F-NMR (376 MHz; DMSO) δ −139.66 (s).

Step f: Preparation of methyl 7-fluoro-6-(2-methyl-phenylamino)-1H-benzoimidazole-5-carboxylate A stirring solution comprised of methyl 4,5-diamino-3-fluoro-2-(2-methyl-phenylamino)-benzoate (1.78 g, 0.00615 mol) in formic acid (Aldrich, 95–97%, 100 ml, 2.5 mol) was brought to reflux for 3 hours followed by concentration in vacuo to give a crude brown solid. The crude product was triturated with chloroform (40 ml) and subsequently collected by vacuum filtration. The solids were dried with suction to afford 1.09 g of a light-lavender powder. The filtrate was concentrated in vacuo to a crude solid which was triturated with 10 ml of chloroform-dichloromethane. These solids were collected by vacuum filtration, rinsed with dichloromethane, and were suction-dried to give an additional 0.55 g of a light-lavender powder (total yield: 1.64 g); 87% yield; m.p. 259–262° C.; $^1$H-NMR (400 MHz; DMSO) δ 8.42 (s, 1H), 8.03 (s, 1H), 7.93 (broad s, 1H), 7.12 (d, 1H), J=7.0 Hz), 6.99–6.95 (m, 1H), 6.75–6.71 (m, 1H), 6.48–6.44 (m, 1H), 3.81 (s, 3H), 2.30 (s, 3H); $^{19}$F-NMR (376 MHz; DMSO) δ −132.84 (s); MS (APCl+) 300 (M+1, 100); (APCl−) 298 (M−1, 100); IR (KBr) 3322, 1689, 1437, 1326, 1218 cm$^{-1}$; Anal. calcd/found for: $C_{16}H_{14}FN_3O_2 \cdot 0.32 H_2O$ C, 62.99/63.01; H, 4.84/4.61; N, 13.77/13.70.

Step g: Preparation of methyl 7-fluoro-6-(4-iodo-2-methyl-phenylamino)-1H-benzoimidazole-5-carboxylate A stirring mixture comprised of methyl 7-fluoro-6-(2-methyl-phenylamino)-1H-benzoimidazole-5-carboxylate (0.2492 g, 8.326×10$^{-4}$ mol), benzyltrimethylammonium dichloroiodinate (Aldrich, 95%, 0.3934 g, 0.00113 mol), and zinc chloride (0.1899 g, 0.00139 mol) in glacial acetic acid (20 ml) was brought to reflux for 15 minutes. The hot suspension was filtered to isolate the precipitate which was dried in the vacuum oven (90° C., ca. 10 mm Hg) overnight to afford 0.2392 g of a green powder; 68% yield; m.p. 219–220° C. DEC; $^1$H-NMR (400 MHz; DMSO) δ 8.71 (s, 1H), 8.02 (s, 1H), 7.85 (broad s, 1H), 7.43 (d, 1H, J=1.7 Hz), 7.24 (dd, 1H, J=8.5, 2.2 Hz), 6.24 (dd, 1H, J=8.5, 5.4 Hz), 3.76 (s, 3H), 2.22 (s, 3H); $^{19}$F-NMR (376 MHz; DMSO) δ −132.86 (s); MS (APCl+) 426 (M+1, 48), 169 (100); (APCl−) 424 (M−1, 100); IR (KBr) 1704, 1508, 1227 cm$^{-1}$.

Step h: Preparation of 7-fluoro-6-(4-iodo-2-methyl-phenylamino)-1H-benzoimidazole-5-carboxylic acid To a stirring solution comprised of methyl 7-fluoro-6-(4-iodo-2-methyl-phenylamino)-1H-benzoimidazole-5-carboxylate (0.2035 g, 4.786×10$^{-4}$ mol) in tetrahydrofuran (20 ml) was added solid potassium trimethylsilanolate (0.315 g, 0.00246 mol). The reaction mixture was stirred at ambient temperature under argon for 16 hours. An additional 0.082 g (6.39×10$^{-4}$ mol) of potassium trimethylsilanolate was added and the mixture stirred 30 minutes. The reaction mixture was concentrated in vacuo to one-third volume and was treated with diethyl ether (50 ml). The off-white precipitate formed was collected by vacuum filtration, giving a hygroscopic solid. The wet solid was dissolved in a 4:1 (v/v) ethyl acetate-methanol solution (500 ml). The solution was washed with 0.84 M aqueous citric acid (50 ml), dried (MgSO$_4$), and concentrated in vacuo to a yellow liquid. The liquid was redissolved in fresh ethyl acetate-methanol. The solution was washed with brine, dried (MgSO$_4$), and concentrated in vacuo. The residue was redissolved in chloroform and reconcentrated to afford 1.55 g of a viscous yellow residue which was comprised mainly of citric acid; MS (APCl−) 191 (M−1, 100). The residue was dissolved in water (50 ml). Insoluble material was extracted into 1:1 (v/v) ethyl acetate-diethyl ether (250 ml). Upon separation, the aqueous phase remained strongly acidic (pH 0). The organic phase was washed with a fresh portion of water (150 ml). Upon separation, this wash was only slightly acidic (pH 4.5). The organic phase was dried (MgSO$_4$), concentrated in vacuo, and chased with chloroform to give a tan semisolid. The product was triturated with hexanes. Vacuum filtration and suction-drying afforded 0.0839 g of a tan powder. A portion of the product (0.050 g) was recrystallized from boiling ethanol (1 ml). While cooling and moderate scratching, an off-white solid formed. This product was isolated by vacuum filtration and dried under high vacuum (23° C.) to afford 0.018 g of an off-white powder; 9% yield; m.p. 247–248° C. DEC; $^{19}$F-NMR (376 MHz; DMSO) δ −132.87 (s); MS (APCl+) 412 (M+1, 100); (APCl−) 410 (M−1, 100); IR (KBr) 3322, 1437, 1326, 1218 cm$^{-1}$; Anal. calcd/found for: $C_{15}H_{11}FIN_3O_2 \cdot 0.61 C_2H_6O \cdot 0.59 H_2O$ (91.4% parent) C, 43.30/43.30; H, 3.55/3.34; N 9.34/9.15.

Example 2

Preparation of 7-fluoro-6-(4-iodo-2-methyl-phenylamino)-1H-benzoimidazole-5-carboxylic acid cyclopropylmethoxy-amide (PD 254552)

(APK IC$_{50}$<10 nM (n=2); colon 26 cells, 1 hour pretreatment, IC$_{50}$=20 nM)

Step a: Preparation of 7-fluoro-6-(4-iodo-2-methyl-phenylamino)-1H-benzoimidazole-5-carboxylic acid pentafluorophenyl ester (PD 254551) (APK IC$_{50}$=120 nM (n=2))

To a stirring suspension comprised of 7-fluoro-6-(4-iodo-2-methyl-phenylamino)-1H-benzoimidazole-5-carboxylic acid (0.844 g, 2.05×10$^{-3}$ mol) in ethyl acetate (4 ml) was added a solution comprised of pentafluorophenol (0.375 g, 2.04×10$^{-3}$ mol) in N,N-dimethylformamide (10 ml). Solid dicyclohexylcarbo-diimide (0.415 g, 1.99×10$^{-3}$ mol) was then added and the reaction mixture was stirred for 22 hours. The reaction mixture was vacuum filtered to remove the precipitate that had formed. The filtrate was diluted with ethyl acetate (400 ml), and that solution was washed with water (3×400 ml), was dried (MgSO$_4$), and was concentrated in vacuo to afford 1.7 g of a yellow foam. The crude product was purified by flash silica column chromatography. Elution with a gradient (CHCl$_3$ to 0.5% methanol in CHCl$_3$) afforded 0.69 g of the yellow amorphous product; 60% yield; $^1$H-NMR (400 MHz; CDCl$_3$) δ 8.54 (s, 1H), 8.28 (s, 1H), 8.04 (s, 1H), 7.49 (d, 1H, J=1.7 Hz), 7.36 (dd, 1H, J=8.2, 1.7 Hz), 6.57 (dd, 1H, J=8.4, 6.5 Hz), 2.31 (s, 3H); $^{19}$F-NMR (376 MHz; CDCl$_3$) δ −132.02 (s), −152.35 (d, J=18.3 Hz), −157.26 (t, J=21.4 Hz), −161.96 (dd, J=21.3, 18.3 Hz); MS (APCl+) 578 (M+1, 57), 394 (100); (APCl−) 576 (M−1, 44), 409 (100), 393 (95), 392 (82), 378 (55), 183 (97), 165 (68), 127 (53); IR (KBr) 1731 cm$^{-1}$ (C=O stretch).

Step b: Preparation of 7-fluoro-6-(4-iodo-2-methyl-phenylamino)-1H-benzoimidazole-5-carboxylic acid cyclopropylmethoxy-amide To a stirring solution comprised of 7-fluoro-6-(4-iodo-2-methyl-phenylamino)-1H-benzoimidazole-5-carboxylic acid pentafluorophenyl ester (0.63 g, 1.09×10$^{-3}$ mol) in anhydrous tetrahydrofuran (5 ml) was added solid cyclopropylmethoxyamine hydrochloride (0.14 g, 1.13×10$^{-3}$ mol) and diisopropylethylamine (0.6 ml, 3.4×10$^{-3}$ mol). The reaction mixture was stirred for one week. The solvent was removed and the evaporate was treated with 10% aqueous hydrochloric acid (200 ml) and was extracted with diethyl ether (200 ml). A biphasic suspension resulted, and the precipitate was isolated by vacuum filtration. The crude product was recrystallized from absolute ethanol to afford 0.18 g of a green-yellow powder; 35% yield; mp 168–172° C.; $^1$H-NMR (400 MHz; DMSO) δ 11.48 (s, 1H), 8.37 (s, 1H), 7.50 (broad s, 1H), 7.45 (s, 1H), 7.24 (s, 1H), 7.07 (d, 1H, J=8.4 Hz), 6.03–5.97 (m, 1H), 3.38 (d, 2H, J=6.5 Hz), 2.04 (s, 3H), 0.85–0.75 (m, 1H), 0.30–0.22 (m, 2H), 0.00 (s, 2H); $^{19}$F-NMR (376 MHz; DMSO) δ −133.23 (s); MS (APCl+) 481 (M+1, 77), 409 (100); (APCl−) 480 (M, 22), 407 (100); IR (KBr) 1659, 1632, 1493 cm$^{-1}$; Anal. calcd/found for: $C_{19}H_{18}FIN_4O_2 \cdot 0.50$ HCl (96.3% parent) C, 45.78/45.74; H, 3.74/3.84; N, 11.24/10.88.

Example 3

Preparation of 7-fluoro-6-(4-iodo-2-methyl-phenylamino)-1H-benzoimidazole-5-carboxylic acid hydroxyamide Step a: Preparation of 7-fluoro-6-(4-iodo-2-methyl-phenylamino)-1H-benzoimidazole-5-carboxylic acid O-(tetrahydro-2H-pyran-2-yl)-oxyamide A solution comprised of 7-fluoro-6-(4-iodo-2-methyl-phenylamino)-1H-benzoimidazole-5-carboxylic acid, O-(tetrahydro-2H-pyran-2-yl)-hydroxylamine (1.25 equiv.), benzotriazole-1-yl-oxy-tris-pyrrolidino-phosphonium hexafluorophosphate (1.25 equiv.), and a diisopropylethylamine (3 equiv.) in 1:1 v/v tetrahydrofuran-dichloromethane is stirred for 30 minutes. The reaction mixture is concentrated in vacuo and the residue is purified by flash chromatography; elution with dichloromethane affords the desired product. The product may be recrystallized with an appropriate solvent like methanol if further purification is necessary.

Step b: Preparation of 7-fluoro-6-(4-iodo-2-methyl-phenylamino)-1H-benzoimidazole-5-carboxylic acid hydroxyamide The compound 7-fluoro-6-(4-iodo-2-methyl-phenylamino)-1H-benzoimidazole-5-carboxylic acid O-(tetrahydro-2H-pyran-2-yl)-oxyamide is dissolved in an appropriate hydrogen chloride-saturated solvent like methanol or ethanol. Once homogeneous, the solution is concentrated in vacuo to give the desired product. The product may be triturated with an appropriate solvent like chloroform or dichloromethane if further purification is necessary.

Example 4

Preparation of 7-fluoro-6-(4-iodo-2-methyl-phenylamino)-1H-benzoimidazole-5-carboxylic acid cyclopropylmethoxy-amide Step a: Preparation of O-cyclopropylmethylhydroxylamine hydrochloride Step i: Preparation of 2-cyclopropylmethoxy-isoindole-1,3-dione To a stirring solution/suspension comprised of N-hydroxyphthalimide (Aldrich, 57.15 g, 339.8 mmol), cyclopropanemethanol (Aldrich, 25.10 g, 341.1 mmol), and triphenylphosphine ("DEAD," Aldrich, 91.0 g, 344 mmol) in 1.00 L of tetrahydrofuran under a nitrogen atmosphere and cooled to 6° C. (internal mixture temperature) with an ice-water bath was added diethyl azodicarboxylate (Aldrich, 56 ml, 356 mmol) dropwise over 20 minutes via addition funnel. The reaction mixture temperature was kept below 20° C. during the addition. Following addition of the DEAD, the cold bath was removed and the reaction mixture was stirred for 15 hours. The mixture was concentrated to a paste under reduced pressure. Chloroform (ca. 300 ml) was added and the mixture swirled to loosen all solids. Vacuum filtration removed the insolubles. The filtrate was likewise filtered to remove white precipitate that formed and to give a clear filtrate. Concentration under reduced pressure afforded a clear oil. Flash filtration through silica gel (100% chloroform) gave filtrates containing unseparated product. These filtrates were combined and concentrated under reduced pressure to afford 127.4 g of a clear oil. The oil was dissolved in absolute ethanol (400 ml) and the solution was refrigerated for two hours. A white crystalline solid had precipitated and was subsequently collected by vacuum filtration. The product was dried in the vacuum oven (60° C.) to afford 42.66 g (58%) of the desired material; m.p. 71–77° C.; $^1$H-NMR (400 MHz; CDCl$_3$ signal offset to δ 6.96) δ 7.54–7.43 (m, 4H), 3.74 (d, 2H, J=7.6 Hz), 1.02–0.95 (m, 1H), 0.34–0.30 (m, 1H), 0.04–0.00 (m, 1H).

Step ii: Preparation of O-cyclopropylmethylhydroxylamine hydrochloride

To a stirring solution comprised of 2-cyclopropyl-methoxy-isoindole-1,3-dione (42.64 g, 196.3 mmol) in 150 ml of dichloromethane under ambient conditions was carefully added methylhydrazine (Aldrich, 10.7 ml, 197 mmol). A white precipitate began to form almost instantly. After 15 minutes of vigorous stirring, the suspension was vacuum filtered. The filtrate was likewise filtered to remove additional precipitate. The resulting clear filtrate was concentrated carefully (volatile product) under reduced pressure to afford a clear liquid/solid mixture. The white solids were removed when an ether (200 ml) solution of the product was made and vacuum filtered. The filtrate was acidified with gaseous hydrogen chloride, affording instantly a white precipitate. Collection of the solid by vacuum filtration and vacuum-oven drying (55° C.) afforded 18.7 g (77%) of the white powder product; m.p. 165–168° C.; $^1$H-NMR (400 MHz; DMSO) δ 10.77 (broad s, 2H), 3.57 (d, 2H, J=7.3 Hz), 0.84–0.74 (m, 1H), 0.31–0.25 (m, 2H), 0.04–0.00 (m, 1H); $^{13}$C-NMR (100 MHz; DMSO) δ 75.39, 5.52, 0.00.

Step b: Preparation of 7-fluoro-6-(4-iodo-2-methyl-phenylamino)-1H-benzoimidazole-5-carboxylic acid cyclopropylmethoxy-amide A solution comprised of 7-fluoro-6-(4-iodo-2-methyl-phenylamino)-1H-benzoimidazole-5-carboxylic acid, O-cyclopropylmethylhydroxylamine hydrochloride (1.25 equiv.), benzotriazole-1-yl-oxy-tris-pyrrolidino-phosphonium hexafluorophosphate (1.25 equiv.), and diisopropylethylamine (3 equiv.) in 1:1 v/v tetrahydrofuran-dichloromethane is stirred for 30 minutes. The reaction mixture is concentrated in vacuo and the residue is taken up into diethyl ether. The ether phase is washed with dilute aqueous hydrochloric acid, saturated aqueous sodium bicarbonate, and brine, is dried (MgSO$_4$), and is concentrated in vacuo to afford the desired product. The product may be recrystallized with an appropriate solvent like methanol or chloroform if further purification is necessary.

Example 5

Preparation of 7-fluoro-6-(4-iodo-2-methyl-phenylamino)-1H-benzooxazole-5-carboxylic acid Step a: Preparation of 5-nitro-2,3,4-trifluorobenzoic acid
Same as for Example 1, Step a.

Step b: Preparation of 2,3-difluoro-4-hydroxy-5-nitrobenzoic acid

The solid 5-nitro-2,3,4-trifluorobenzoic acid (1.00 g, 0.00452 mol) was dissolved in 10 wt. % aqueous sodium hydroxide solution. The mixture was clear deep orange. After standing under ambient conditions for several minutes, the mixture was quenched with concentrated aqueous hydrochloric acid until strongly acidic (pH 0). A white solid precipitated which was isolated by vacuum filtration and dried with suction to afford 0.40 g of an off-white solid. This solid was recrystallized from chloroform (20 ml) to afford 0.22 g of an off-white crystalline powder; 22% yield; MS (APCl−) 218 (M−1, 100).

Step c: Preparation of methyl 2,3-difluoro-4-hydroxy-5-nitrobenzoate

Anhydrous hydrogen chloride gas was dissolved in anhydrous methanol (50 ml) until the solution was warm. The microcrystalline solid 2,3-difluoro-4-hydroxy-5-nitrobenzoic acid 0.22 g, 0.00100 mol) was dissolved in the methanolic hydrogen chloride solution. The stirring reaction mixture was brought to reflux under nitrogen for 16 hours. The mixture was concentrated in vacuo to give a white solid. The product was dried under high vacuum to afford 0.213 g of a white powder; 91% yield; m.p. 108–109.5° C.; $^1$H-NMR (400 MHz; DMSO) δ 8.25 (dd, 1H, J=7.7, 2.2 Hz), 3.83 (s, 3H); (CDCl$_3$) δ 10.83 (s, 1H), 8.66 (dd, 1H, J=7.0, 2.2 Hz), 3.98 (s, 3H); $^{19}$F-NMR (376 MHz; DMSO) δ −127.85 (s), −154.32 (d, J=19.8 Hz); (CDCl$_3$) δ −118.31 to −118.37 (m), −152.38 (d, J=18.3 Hz); MS (APCl−) 232 (M−1, 100); IR (KBr) 3264, 1731, 1640, 1546, 1307, 1286, 1160 cm$^{-1}$.

Step d: Preparation of 1-adamantyl 4-carboxymethyl-2,3-difluoro-6-nitrophenyl carbonate To a solution comprised of 1-adamantyl fluoroformate (2.0 M) and pyridine (2.0 M) in tetrahydrofuran is added a stirred solution comprised of methyl 2,3-difluoro-4-hydroxy-5-nitrobenzoate (0.96 equiv., 0.384 M) in anhydrous tetrahydrofuran at ambient temperature. The reaction mixture is stirred for 6 hours and the solvent is removed in vacuo. The residue is dissolved in dichloromethane. The organic solution is washed with dilute aqueous hydrochloric acid, dilute aqueous sodium carbonate, and water, is dried (MgSO$_4$), and is concentrated in vacuo to give the desired product.

Step e: Preparation of 1-adamantyl 4-carboxymethyl-2-fluoro-3-(2-methyl-phenylamino)-6-nitrophenyl carbonate The compound 1-adamantyl 4-carboxymethyl-2,3-difluoro-6-nitrophenyl carbonate is dissolved in excess ortho-toluidine. The reaction mixture is stirred at 200° C. for 6 hours. The mixture is allowed to cool and is dissolved in diethyl ether. The organic phase is washed with dilute aqueous hydrochloric acid, saturated aqueous sodium bicarbonate, and brine, is dried (MgSO$_4$), and is concentrated in vacuo to afford the desired product. The product is purified by flash chromatography as necessary.

Step f: Preparation of methyl 3-fluoro-4-hydroxy-2-(2-methyl-phenylamino)-5-nitrobenzoate The compound 1-adamantyl 4-carboxymethyl-2-fluoro-3-(2-methyl-phenylamino)-6-nitrophenyl carbonate is dissolved in excess trifluoroacetic acid at ambient temperature. The mixture is stirred for 20 minutes. The TFA is removed under reduced pressure. The residue is subjected to vacuum pump to remove adamantan-1-ol to give the desired product.

Step g: Preparation of methyl 5-amino-3-fluoro-4-hydroxy-2-(2-methyl-phenylamino)-benzoate The compound methyl 3-fluoro-4-hydroxy-2-(2-methyl-phenylamino)-5-nitrobenzoate is treated as in Step e, Example 1.

Step h: Preparation of methyl 7-fluoro-6-(2-methyl-phenylamino)-1H-benzooxazole-5-carboxylate The compound 5-amino-3-fluoro-4-hydroxy-2-(2-methyl-phenylamino)-benzoate is treated as in Step f, Example 1. The product may be recrystallized with an appropriate solvent like chloroform or ethanol if further purification is necessary.

Step i: Preparation of methyl 7-fluoro-6-(4-iodo-2-methyl-phenylamino)-1H-benzooxazole-5-carboxylate A stirring mixture comprised of methyl 7-fluoro-6-(2-methyl-phenylamino)-1H-benzooxazole-5-carboxylate (0.042 M), benzyltrimethylammonium dichloroiodinate (Aldrich, 95%, 0.057 M, 1.36 equiv.), and zinc chloride (0.070 M, 1.67 equiv.) in glacial acetic acid is brought to reflux for 15 minutes. The mixture is concentrated in vacuo and the residue taken up into diethyl ether. The ether solution is washed with dilute aqueous hydrochloric acid, water, and brine, is dried (MgSO$_4$), and is concentrated in vacuo to obtain the desired product. The product may be purified by recrystallization with an appropriate solvent like ethanol.

Step j: Preparation of 7-fluoro-6-(4-iodo-2-methyl-phenylamino)-1H-benzooxazole-5-carboxylic acid To a stirring solution comprised of methyl 7-fluoro-6-(4-iodo-2-methyl-phenylamino)-1H-benzooxazole-5-carboxylate (0.024 M) in tetrahydrofuran is added solid potassium trimethylsilanolate (5.14 equiv.). The reaction mixture is stirred at ambient temperature under argon for 16 hours. An additional equivalent of potassium trimethylsilanolate is added and the mixture stirred 30 minutes. The reaction mixture is concentrated in vacuo to give a residue that is then taken up into 1:1 (v/v) ethyl acetate-diethyl ether. The organic phase is washed with dilute aqueous hydrochloric acid, water, and brine, is dried (MgSO$_4$), is concentrated in vacuo, and chased with chloroform to give a crude product. Recrystallization from an appropriate solvent like ethanol gives the purified desired product.

Example 6

Preparation of 7-fluoro-6-(4-iodo-2-methyl-phenylamino)-1H-benzooxazole-5-carboxylic acid hydroxyamide Step a: Preparation of 7-fluoro-6-(4-iodo-2-methyl-phenylamino)-1H-benzooxazole-5-carboxylic acid O-(tetrahydro-2H-pyran-2-yl)-oxyamide The compound 7-fluoro-6-(4-iodo-2-methyl-phenylamino)-1H-benzooxazole-5-carboxylic acid is treated as in Step a, Example 2.

Step b: Preparation of 7-fluoro-6-(4-iodo-2-methyl-phenylamino)-1H-benzooxazole-5-carboxylic acid hydroxyamide The compound 7-fluoro-6-(4-iodo-2-methyl-phenylamino)-1H-benzooxazole-5-carboxylic acid O-(tetrahydro-2H-pyran-2-yl)-oxyamide is treated as in Step b, Example 2.

Example 7

Preparation of 7-fluoro-6-(4-iodo-2-methyl-phenylamino)-1H-benzooxazole-5-carboxylic acid cyclopropylmethoxy-amide The compound 7-fluoro-6-(4-iodo-2-methyl-phenylamino)-1H-benzooxazole-5-carboxylic acid is treated as in Step b, Example 3.

Example 8

Preparation of 7-fluoro-6-(4-iodo-2-methyl-phenylamino)-1H-benzothiazole-5-carboxylic acid Step a: Preparation of 5-nitro-2,3,4-trifluorobenzoic acid Same as for Example 1, Step a.

Step b: Preparation of 2,3-difluoro-4-hydroxy-5-nitrobenzoic acid

Same as for Example 4, Step b.

Step c: Preparation of methyl 2,3-difluoro-4-hydroxy-5-nitrobenzoate

Same as for Example 4, Step c.

Step d: Preparation of 4-dimethylthiocarbamoyloxy-2,3-difluoro-5-nitrobenzoic acid methyl ester A solution of methyl 2,3-difluoro-4-hydroxy-5-nitrobenzoate in N,N-dimethylformamide is treated with one molar equivalent of cesium carbonate and warmed to 85° C. for 30 minutes. The stirring mixture is then treated dropwise rapidly with a solution comprised of a slight excess of N,N-dimethylthiocarbamoyl chloride in N,N-dimethylformamide. The reaction mixture is stirred at room temperature for one hour, or may be warmed over a steam bath for one hour. The mixture is then poured into water and extracted with ethyl acetate. The organic phase is washed with 5% aqueous sodium hydroxide, water, and brine, and is then dried with a drying agent like magnesium sulfate of sodium sulfate. The solvent is then removed in vacuo to give a crude product. The compound is purified by ordinary methods such as chromatography or crystallization from an appropriate solvent.

Step e: Preparation of 4-Dimethylthiocarbamoyloxy-3-fluoro-5-nitro-2-o-tolylamino-benzoic acid methyl ester The compound 4-dimethylthiocarbamoyloxy-2,3-difluoro-5-nitro-benzoic acid methyl ester is dissolved in excess o-toluidine. The stirring mixture is brought to 200° C. for one hour. The mixture is then poured into 5% aqueous hydrochloric acid. The aqueous mixture is extracted with diethyl ether. The organic phase is washed with water and brine, is dried over magnesium sulfate, and is concentrated in vacuo. The crude product is purified by ordinary methods such as chromatography or crystallization from an appropriate solvent.

Step f: Preparation of methyl 7-fluoro-6-(2-methyl-phenylamino)-1H-benzothiazole-5-carboxylate The compound methyl 5-amino-3-fluoro-4-mercapto-2-(2-methyl-phenylamino)-benzoate is treated as in Step h, Example 4.

Step g: Preparation of methyl 7-fluoro-6-(4-iodo-2-methyl-phenylamino)-1H-benzothiazole-5-carboxylate The compound methyl 7-fluoro-6-(2-methyl-phenylamino)-1H-benzothiazole-5-carboxylate is treated as in Step i, Example 4.

Step h: Preparation of 7-fluoro-6-(4-iodo-2-methyl-phenylamino)-1H-benzothiazole-5-carboxylic acid The compound methyl 7-fluoro-6-(4-iodo-2-methyl-phenylamino)-1H-benzothiazole-5-carboxylate is treated as in Step j, Example 4.

Example 9

Preparation of 7-fluoro-6-(4-iodo-2-methyl-phenylamino)-1H-benzothiazole-5-carboxylic acid hydroxyamide Step a: Preparation of 7-fluoro-6-(4-iodo-2-methyl-phenylamino)-1H-benzothiazole-5-carboxylic acid O-(tetrahydro-2H-pyran-2-yl)-oxyamide The compound 7-fluoro-6-(4-iodo-2-methyl-phenylamino)-1H-benzothiazole-5-carboxylic acid is treated as in Step a, Example 2.

Step b: Preparation of 7-fluoro-6-(4-iodo-2-methyl-phenylamino)-1H-benzothiazole-5-carboxylic acid hydroxyamide The compound 7-fluoro-6-(4-iodo-2-methyl-phenylamino)-1H-benzothiazole-5-carboxylic acid O-(tetrahydro-2H-pyran-2-yl)-oxyamide is treated as in Step b, Example 2.

Example 10

Preparation of 7-fluoro-6-(4-iodo-2-methyl-phenylamino)-1H-benzothiazole-5-carboxylic acid cyclopropylmethoxy-amide The compound 7-fluoro-6-(4-iodo-2-methyl-phenylamino)-1H-benzothiazole-5-carboxylic acid is treated as in Step b, Example 3.

Example 11

Preparation of 8-fluoro-7-(4-iodo-2-methyl-phenylamino)-quinoxaline-6-carboxylic acid Step a: Preparation of 8-fluoro-7-(2-methyl-phenylamino)-quinoxaline-6-carboxylic acid The compound methyl 4,5-diamino-3-fluoro-2-(2-methyl-phenylamino)-benzoate (from Step e, Example 1) is dissolved in 2:1:1.2 v/v/v of 2.0 M acetic acid-4.0 M sodium acetate-methanol. The suspension is warmed to 65° C. (or until homogeneous) and the clear solution is poured into a 0.078 M aqueous sodium glyoxal bisulfite (Aldrich, monohydrate, 1.05 equiv.) solution which is warmed to 70° C. The reaction mixture is stirred gently between 55–75° C. for one hour, and is then cooled to 12° C. with an ice-water bath. Pulverized sodium hydroxide pellets (27 equiv.) are added to the cold solution. The mixture is gently warmed to 30° C. and stirred for 45 minutes. The temperature is raised to 70° C. for 15 minutes. The mixture is allowed to cool and is treated with ethyl acetate. The biphasic mixture is treated with concentrated aqueous hydrochloric acid to achieve pH 0 in the aqueous phase. The organic phase is separated, dried ($MgSO_4$), and concentrated in vacuo to give the desired product. The product may be triturated with an appropriate solvent like dichloromethane or recrystallized from a solvent like ethanol for further purification as necessary.

Step b: Preparation of 8-fluoro-7-(4-iodo-2-methyl-phenylamino)-quinoxaline-6-carboxylic acid The compound 8-fluoro-7-(2-methyl-phenylamino)-quinoxaline-6-carboxylic acid is treated as in Step i, Example 4.

Example 12

Preparation of 8-fluoro-7-(4-iodo-2-methyl-phenylamino)-quinoxaline-6-carboxylic acid hydroxyamide Step a: Preparation of 8-fluoro-7-(4-iodo-2-methyl-phenylamino)-quinoxaline-6-carboxylic acid O-(tetrahydro-2H-pyran-2-yl)-oxyamide The compound 8-fluoro-7-(4-iodo-2-methyl-phenylamino)-quinoxaline-6-carboxylic acid is treated as in Step a, Example 2.

Step b: Preparation of 8-fluoro-7-(4-iodo-2-methyl-phenylamino)-quinoxaline-6-carboxylic acid hydroxyamide The compound 8-fluoro-7-(4-iodo-2-methyl-phenylamino)-quinoxaline-6-carboxylic acid O-(tetrahydro-2H-pyran-2-yl)-oxyamide is treated as in Step b, Example 2.

Example 13

Preparation of 8-fluoro-7-(4-iodo-2-methyl-phenylamino)-quinoxaline-6-carboxylic acid cyclopropylmethoxy-amide The compound 8-fluoro-7-(4-iodo-2-methyl-phenylamino)-quinoxaline-6-carboxylic acid is treated as in Step b, Example 3.

Example 14

Preparation of 7-fluoro-6-(4-iodo-2-methyl-phenylamino)-benzo[1,2,5]thiadiazole-5-carboxylic acid Step a: Preparation of methyl 7-fluoro-6-(2-methyl-phenylamino)-benzo[1,2,5]thiadiazole-5-carboxylate To a stirring solution comprised of methyl 4,5-diamino-3-fluoro-2-(2-methyl-phenylamino)-benzoate (from Step e, Example 1) and diisopropylethylamine (2 equiv.) in an appropriate solvent like diethyl ether or toluene is added a reagent like N-thioaniline or thionyl chloride (1.35 equiv.). The reaction mixture is brought to reflux for one hour. The mixture is quenched with dilute aqueous hydrochloric acid. The organic phase is washed with saturated aqueous sodium bicarbonate and brine, is dried (MgSO$_4$), and is concentrated in vacuo to afford the desired product. The product may be recrystallized with an appropriate solvent like chloroform or ethanol, or may be chromatographed if further purification is necessary.

Alternative method: The compound methyl 4,5-diamino-3-fluoro-2-(2-methyl-phenylamino)-benzoate is added to a stirring solution of sulfur monochloride (6 equiv.) in N,N-dimethylformamide and the mixture is gradually heated to 75–80° C. After 5 hours the mixture is cooled to 10° C., water is slowly added. The mixture is extracted with a solvent like diethyl ether or dichloromethane. The organic extract is dried (MgSO$_4$) and is concentrated in vacuo to afford the desired product. The product may be recrystallized with an appropriate solvent like chloroform or ethanol, or may be chromatographed if further purification is necessary.

Step b: Preparation of methyl 7-fluoro-6-(4-iodo-2-methyl-phenylamino)-benzo[1,2,5]thiadiazole-5-carboxylate The compound methyl 7-fluoro-6-(2-methyl-phenylamino)-benzo[1,2,5]thiadiazole-5-carboxylate is treated as in Step i, Example 4.

Step c: Preparation of 7-fluoro-6-(4-iodo-2-methyl-phenylamino)-benzo[1,2,5]thiadiazole-5-carboxylic acid The compound methyl 7-fluoro-6-(4-iodo-2-methyl-phenylamino)-benzo[1,2,5]thiadiazole-5-carboxylate is treated as in Step j, Example 4.

Example 15

Preparation of 7-fluoro-6-(4-iodo-2-methyl-phenylamino)-benzo[1,2,5]thiadiazole-5-carboxylic acid hydroxyamide Step a: Preparation of 7-fluoro-6-(4-iodo-2-methyl-phenylamino)-benzo[1,2,5]thiadiazole-5-carboxylic acid O-(tetrahydro-2H-pyran-2-yl)-oxyamide The compound 7-fluoro-6-(4-iodo-2-methyl-phenylamino)-benzo[1,2,5]thiadiazole-5-carboxylic acid is treated as in Step a, Example 2.

Step b: Preparation of 7-fluoro-6-(4-iodo-2-methyl-phenylamino)-benzo[1,2,5]thiadiazole-5-carboxylic acid hydroxyamide The compound 7-fluoro-6-(4-iodo-2-methyl-phenylamino)-benzo[1,2,5]thiadiazole-5-carboxylic acid O-(tetrahydro-2H-pyran-2-yl)-oxyamide is treated as in Step b, Example 2.

Example 16

Preparation of 7-fluoro-6-(4-iodo-2-methyl-phenylamino)-benzo[1,2,5]thiadiazole-5-carboxylic acid cyclopropylmethoxy-amide The compound 7-fluoro-6-(4-iodo-2-methyl-phenylamino)-benzo[1,2,5]thiadiazole-5-carboxylic acid is treated as in Step b, Example 3.

Example 17

Preparation of 7-fluoro-6-(4-iodo-2-methyl-phenylamino)-benzo[1,2,5]oxadiazole-5-carboxylic acid Step a: Preparation of methyl 7-fluoro-6-(2-methyl-phenylamino)-benzo[1,2,5]oxadiazole-5-carboxylate 2-oxide See Takakis, I. M.; Hadjimihalakis, P. M., *J. Heterocyclic Chem.*, 27, 177 (1990).

A mixture comprised of methyl 4-amino-3-fluoro-2-(2-methyl-phenylamino)-5-nitrobenzoate (from Step d, Example 1) and iodosobenzenediacetate (1.76 equiv.) in benzene is stirred at ambient temperature for 5 hours. The mixture is concentrated in vacuo and the residue purified by column chromatography to give the desired product.

Alternative method: A solution comprised of methyl 4-amino-3-fluoro-2-(2-methyl-phenylamino)-5-nitrobenzoate (0.86 M) in tetrahydrofuran is diazotized and the diazonium salt is treated in situ with sodium azide as described by Smith, P. A. S.; Boyer, J. H., *Org. Synth.*, 31, 14 (1951) and references 4 and 8 cited therein. Thermolysis of this intermediate in ethylene glycol at 110–120° C. for one hour affords the desired product.

Step b: Preparation of methyl 7-fluoro-6-(2-methyl-phenylamino)-benzo[1,2,5]oxadiazole-5-carboxylate A solution comprised of methyl 7-fluoro-6-(2-methyl-phenylamino)-benzo[1,2,5]oxadiazole-5-carboxylate 2-oxide and sodium azide (1.38 equiv.) in ethylene glycol is heated to 140–150° C. for 30 minutes to obtain, after column chromatography, the desired product.

Step c: Preparation of methyl 7-fluoro-6-(4-iodo-2-methyl-phenylamino)-benzo[1,2,5]oxadiazole-5-carboxylate The compound methyl 7-fluoro-6-(2-methyl-phenylamino)-benzo[1,2,5]oxadiazole-5-carboxylate is treated as in Step i, Example 4.

Step d: Preparation of 7-fluoro-6-(4-iodo-2-methyl-phenylamino)-benzo[1,2,5]oxadiazole-5-carboxylic acid The compound methyl 7-fluoro-6-(4-iodo-2-methyl-phenylamino)-benzo[1,2,5]oxadiazole-5-carboxylate is treated as in Step j, Example 4.

Example 18

Preparation of 7-fluoro-6-(4-iodo-2-methyl-phenylamino)-benzo[1,2,5]oxadiazole-5-carboxylic acid hydroxyamide Step a: Preparation of 7-fluoro-6-(4-iodo-2-methyl-phenylamino)-benzo[1,2,5]oxadiazole-5-carboxylic acid O-(tetrahydro-2H-pyran-2-yl)-oxyamide The compound 7-fluoro-6-(4-iodo-2-methyl-phenylamino)-benzo[1,2,5]oxadiazole-5-carboxylic acid is treated as in Step a, Example 2.

Step b: Preparation of 7-fluoro-6-(4-iodo-2-methyl-phenylamino)-benzo[1,2,5]oxadiazole-5-carboxylic acid hydroxyamide The compound 7-fluoro-6-(4-iodo-2-methyl-phenylamino)-benzo[1,2,5]oxadiazole-5-carboxylic acid O-(tetrahydro-2H-pyran-2-yl)-oxyamide is treated as in Step b, Example 2.

Example 19

Preparation of 7-fluoro-6-(4-iodo-2-methyl-phenylamino)-benzo[1,2,5]oxadiazole-5-carboxylic acid cyclopropylmethoxy-amide The compound 7-fluoro-6-(4-iodo-2-methyl-phenylamino)-benzo[1,2,5]oxadiazole-5-carboxylic acid is treated as in Step b, Example 3.

Example 20

Preparation of 7-fluoro-6-(4-iodo-2-methyl-phenylamino)-1H-benzotriazole-5-carboxylic acid Step a: Preparation of methyl 7-fluoro-6-(2-methyl-phenylamino)-1H-benzotriazole-5-carboxylate The compound methyl 4,5-diamino-3-fluoro-2-(2-methyl-phenylamino)-benzoate (from Step e, Example 1) is diazotized by ordinary methods. Workup gives the desired product.

Step b: Preparation of methyl 7-fluoro-6-(4-iodo-2-methyl-phenylamino)-1H-benzotriazole-5-carboxylate The compound methyl 7-fluoro-6-(2-methyl-phenylamino)-1H-benzotriazole-5-carboxylate is treated as in Step i, Example 4.

Step c: Preparation of 7-fluoro-6-(4-iodo-2-methyl-phenylamino)-1H-benzotriazole-5-carboxylic acid The compound methyl 7-fluoro-6-(4-iodo-2-methyl-phenylamino)-1H-benzotriazole-5-carboxylate is treated as in Step j, Example 4.

Example 21

Preparation of 7-fluoro-6-(4-iodo-2-methyl-phenylamino)-1H-benzotriazole-5-carboxylic acid hydroxyamide Step a: Preparation of 7-fluoro-6-(4-iodo-2-methyl-phenylamino)-1H-benzotriazole-5-carboxylic acid O-(tetrahydro-2H-pyran-2-yl)-oxyamide The compound 7-fluoro-6-(4-iodo-2-methyl-phenylamino)-1H-benzotriazole-5-carboxylic acid is treated as in Step a, Example 2.

Step b: Preparation of 7-fluoro-6-(4-iodo-2-methyl-phenylamino)-1H-benzotriazole-5-carboxylic acid hydroxyamide The compound 7-fluoro-6-(4-iodo-2-methyl-phenylamino)-1H-benzotriazole-5-carboxylic acid O-(tetrahydro-2H-pyran-2-yl)-oxyamide is treated as in Step b, Example 2.

Example 22

Preparation of 7-fluoro-6-(4-iodo-2-methyl-phenylamino)-1H-benzotriazole-5-carboxylic acid cyclopropylmethoxy-amide The compound 7-fluoro-6-(4-iodo-2-methyl-phenylamino)-1H-benzotriazole-5-carboxylic acid is treated as in Step b, Example 3.

F. Other Embodiments

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or an ester, pharmaceutical salt, hydrate, acid, or amide of a disclosed compound. Publications cited herein are hereby incorporated by reference in their entirety.

What is claimed is:

1. A method for treating chronic pain, wherein said chronic pain is a type of neuropathic pain, said method comprising administering to a subject in need of such treatment a composition comprising a MEK inhibitor selected from a compound of the following formula (I):

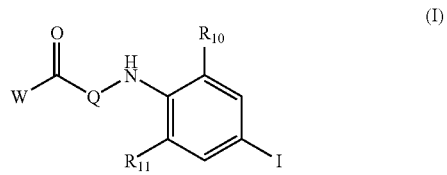

wherein
W is $OR_1$, $NR_2OR_1$, $NR_AR_B$, $NR_2NR_AR_B$, $O(CH_2)_{2-4}NR_AR_B$, or $NR_2(CH_2)_{2-4}NR_AR_B$;
$R_1$ is H, $C_{1-8}$alkyl, $C_{3-8}$alkenyl, $C_{3-8}$alkynyl, $C_{3-8}$cycloalkyl, phenyl, (phenyl)$C_{1-4}$alkyl, (phenyl)$C_{3-4}$alkenyl, (phenyl)$C_{3-4}$alkynyl, ($C_{3-8}$cycloalkyl)$C_{1-4}$alkyl, ($C_{3-8}$cycloalkyl)$C_{3-4}$alkenyl, ($C_{3-8}$cycloalkyl)$C_{3-4}$alkynyl, $C_{3-8}$heterocyclic radical, ($C_{3-8}$heterocyclic radical) $C_{1-4}$alkyl, ($C_{3-8}$heterocyclic radical)-$C_{3-4}$alkenyl, ($C_{3-8}$ heterocyclic radical)$C_{3-4}$alkynyl or $(CH_2)_{2-4}NR_CR_D$;

$R_2$ is H, $C_{1-4}$alkyl, phenyl, $C_{3-6}$cycloalkyl, $C_{3-6}$heterocyclic radical, or ($C_{3-6}$cycloalkyl)methyl;

$R_A$ is H, $C_{1-6}$alkyl, $C_{3-8}$alkenyl, $C_{3-8}$alkynyl, $C_{3-8}$cycloalkyl, phenyl, ($C_{3-8}$cycloalkyl)$C_{1-4}$alkyl, ($C_{3-8}$cycloalkyl)$C_{3-4}$alkenyl, ($C_{3-8}$cycloalkyl)$C_{3-4}$alkynyl, $C_{3-8}$heterocyclic radical, ($C_{3-8}$heterocyclic radical)$C_{1-4}$ alkyl, (aminosulfonyl)phenyl, [(aminosulfonyl)phenyl] $C_{1-4}$alkyl, (aminosulfonyl)$C_{1-6}$alkyl, (aminosulfonyl) $C_{3-6}$cycloalkyl, [(aminosulfonyl)$C_{3-6}$cycloalkyl]$C_{1-4}$ alkyl, or $(CH_2)_{2-4}NR_CR_D$;

$R_B$ is H, $C_{1-8}$alkyl, $C_{3-8}$alkenyl, $C_{3-8}$alkynyl, $C_{3-8}$cycloalkyl, or phenyl;

Q is one of the following formulae (i)–(iii):

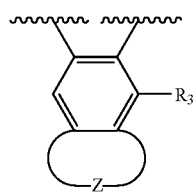 (i)

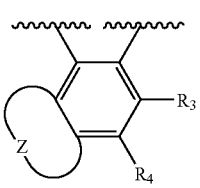 (ii)

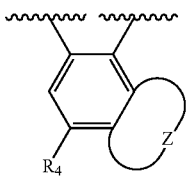 (iii)

$R_3$ is H or F;
$R_4$ is halo, $NO_2$, $SO_2NR_O(CH_2)_{2-4}NR_ER_F$, $SO_2NR_ER_F$, or (CO)T;
T is $C_{1-8}$alkyl, $C_{3-8}$cycloalkyl, $(NR_ER_F)C_{1-4}$alkyl, $OR_F$, $-NR_O(CH_2)_{2-4}NR_ER_F$, or $NR_ER_F$;
Z is one of the following formulae (iv)–(viii):

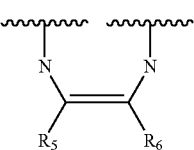 (iv)

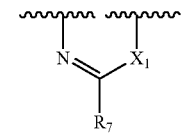 (v)

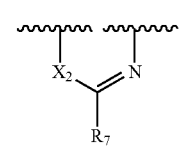 (vi)

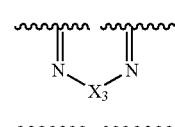 (vii)

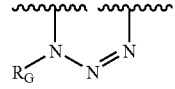 (viii)

one of $R_5$ and $R_6$ is H or methyl and the other of $R_5$ and $R_6$ is H, $C_{1-6}$alkyl, $C_{2-6}$alkenyl, $C_{2-6}$alkynyl, phenyl, benzyl, or —M-E-G;

M is O, CO, $SO_2$, $NR_J$, (CO)$NR_H$, $NR_H$(CO), $NR_H(SO_2)$, $(SO_2)NR_H$, or $CH_2$;

E is $(CH_2)_{1-4}$ or $(CH_2)_mO(CH_2)_p$ where $1\leq$(each of m and p)$\leq 3$ and $2\leq$(m+p)$\leq 4$; or E is absent;

G is $R_K$, $OR_I$ or $NR_JR_K$, provided that if p=1, then G is H;

$R_7$ is H, $C_{1-4}$alkyl, $C_{2-4}$alkenyl, $C_{2-4}$alkynyl, $C_{3-6}$cycloalkyl, phenyl, 2-pyridyl, 3-pyridyl, 4-pyridyl, $(CH_2)_{1-2}Ar$, where Ar is phenyl, 2-pyridyl, 3-pyridyl, or 4-pyridyl, $SO_2NR_H(CH_2)_{2-4}NR_JR_K$, (CO)$(CH_2)_{2-4}NR_JR_K$ or (CO) $NR_H(CH_2)_{2-4}NR_JR_K$;

$X_1$ is O, S, $NR_8$, or $CHR_9$; $X_2$ is O, S, or $CHR_9$; and $X_3$ is O or S; where if $X_1$ or $X_2$ is $CHR_9$, said compound may also be a tautomerized indole;

$R_8$ is H, $C_{1-4}$alkyl, phenyl, 2-pyridyl, 3-pyridyl, 4-pyridyl, $(CH_2)_{1-2}Ar$, where Ar is phenyl, 2-pyridyl, 3-pyridyl, or 4-pyridyl, $C_{2-4}$alkenyl, $C_{2-4}$alkynyl, $C_{3-6}$cycloalkyl, or $(C_{2-4}$alkyl)$NR_LR_M$; provided $R_7$ and $R_8$ together have no more than 14 carbon atoms, exclusive of $R_L$, $R_M$, $R_J$ and $R_K$;

$R_G$ is $C_{1-4}$alkyl, phenyl, 2-pyridyl, 3-pyridyl, 4-pyridyl, $C_{3-4}$alkenyl, $C_{3-4}$alkynyl, $C_{3-6}$cycloalkyl, (CO)$OR_P$, $(C_{2-4}$alkyl)$NR_LR_M$, (CO)$NR_N(CH_2)_{2-4}NR_LR_M$, (CO) $NR_LR_M$, (CO)$(CH_2)_{2-4}$-$NR_LR_M$, or $(CH_2)_{1-2}Ar$, where Ar is phenyl, 2-pyridyl, 3-pyridyl, or 4-pyridyl;

$R_9$ is $C_{1-4}$alkyl, phenyl, 2-pyridyl, 3-pyridyl, 4-pyridyl, $C_{2-4}$alkenyl, $C_{2-4}$alkynyl, $C_{3-6}$cycloalkyl, (CO)$OR_P$, $(C_{2-4}$alkyl)$NR_LR_M$, (CO)$NR_N$ $(CH_2)_{2-4}NR_LR_M$, (CO)$NR_LR_M$, (CO)$(CH_2)_{2-4}$-$NR_LR_M$, or $(CH_2)_{1-2}Ar'$, where Ar' is phenyl, 2-pyridyl, 3-pyridyl, or 4-pyridyl;

$R_P$ is H, $C_{1-6}$alkyl, phenyl, $C_{3-4}$alkenyl, $C_{3-4}$alkynyl, $C_{3-6}$cycloalkyl, or $(CH_2)_{2-4}NR_LR_M$;

$R_{10}$ is H, methyl, halo, or $NO_2$;
$R_{11}$ is H, methyl, halo, or $NO_2$;
each of $R_C$, $R_D$, $R_E$, $R_F$, $R_I$, $R_J$, $R_K$, $R_L$ and $R_M$ is independently selected from H, $C_{1-4}$alkyl, $C_{3-4}$alkenyl, $C_{3-4}$alkynyl, $C_{3-6}$cycloalkyl, and phenyl; each of $NR_CR_D$, $NR_ER_F$, $NR_JR_K$, and $NR_LR_M$ can also independently be morpholinyl, piperazinyl, pyrrolidinyl, or piperidinyl; and each of $R_H$, $R_N$, and $R_O$ is independently H, methyl, or ethyl;

wherein each hydrocarbon radical or heterocyclic radical above is optionally substituted with between 1 and 3 substituents independently selected from halo, $C_{1-4}$alkyl, $C_{3-6}$cycloalkyl, $C_{3-4}$alkenyl, $C_{3-4}$alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$alkyl, hydroxyl, amino, and $NO_2$;

or a pharmaceutically acceptable salt or $C_{1-7}$ ester thereof.

2. The method of claim 1, wherein said neuropathic pain is associated with one of the following: inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, post-operative pain, and arthritis pain, inclusively.

3. A method for treating chronic pain, wherein said chronic pain is associated with inflammation, said method comprising administering to a subject in need of such treatment a composition comprising a MEK inhibitor selected from a compound of the following formula (I):

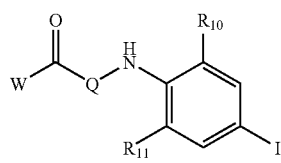

wherein

W is $OR_1$, $NR_2OR_1$, $NR_AR_B$, $NR_2NR_AR_B$, $O(CH_2)_{2-4}NR_AR_B$, or $NR_2(CH_2)_{2-4}NR_AR_B$;

$R_1$ is H, $C_{1-8}$alkyl, $C_{3-8}$alkenyl, $C_{3-8}$alkynyl, $C_{3-8}$cycloalkyl, phenyl, (phenyl)$C_{1-4}$alkyl, (phenyl)$C_{3-4}$alkenyl, (phenyl)$C_{3-4}$alkynyl, ($C_{3-8}$cycloalkyl)$C_{1-4}$alkyl, ($C_{3-8}$cycloalkyl)$C_{3-4}$alkenyl, ($C_{3-8}$cycloalkyl)$C_{3-4}$alkynyl, $C_{3-8}$heterocyclic radical, ($C_{3-8}$heterocyclic radical)$C_{1-4}$alkyl, ($C_{3-8}$heterocyclic radical)-$C_{3-4}$alkenyl, ($C_{3-8}$heterocyclic radical)$C_{3-4}$alkynyl or $(CH_2)_{2-4}NR_CR_D$;

$R_2$ is H, $C_{1-4}$alkyl, phenyl, $C_{3-6}$cycloalkyl, $C_{3-6}$heterocyclic radical, or ($C_{3-6}$cycloalkyl)methyl;

$R_A$ is H, $C_{1-6}$alkyl, $C_{3-8}$alkenyl, $C_{3-8}$alkynyl, $C_{3-8}$cycloalkyl, phenyl, ($C_{3-8}$cycloalkyl)$C_{1-4}$alkyl, ($C_{3-8}$cycloalkyl)$C_{3-4}$alkenyl, ($C_{3-8}$cycloalkyl)$C_{3-4}$alkynyl, $C_{3-8}$heterocyclic radical, ($C_{3-8}$heterocyclic radical)$C_{1-4}$alkyl, (aminosulfonyl)phenyl, [(aminosulfonyl)phenyl]$C_{1-4}$alkyl, (aminosulfonyl)$C_{1-6}$alkyl, (aminosulfonyl)$C_{3-6}$cycloalkyl, [(aminosulfonyl)$C_{3-6}$cycloalkyl]$C_{1-4}$alkyl, or $(CH_2)_{2-4}NR_CR_D$;

$R_B$ is H, $C_{1-8}$alkyl, $C_{3-8}$alkenyl, $C_{3-8}$alkynyl, $C_{3-8}$cycloalkyl, or phenyl;

Q is one of the following formulae (i)–(iii):

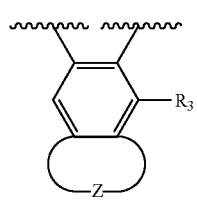

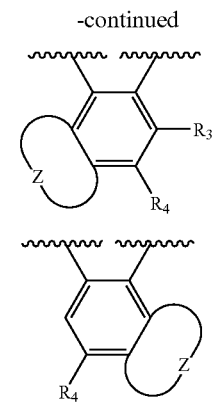

$R_3$ is H or F;

$R_4$ is halo, $NO_2$, $SO_2NR_O(CH_2)_{2-4}NR_ER_F$, $SO_2NR_ER_F$, or (CO)T;

T is $C_{1-8}$alkyl, $C_{3-8}$cycloalkyl, $(NR_ER_F)C_{1-4}$alkyl, $OR_F$, —$NR_O(CH_2)_{2-4}NR_ER_F$, or $NR_ER_F$;

Z is one of the following formula (iv)–(viii):

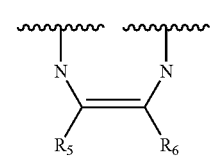

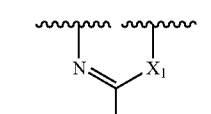

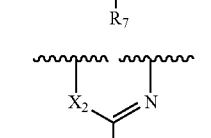

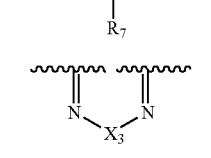

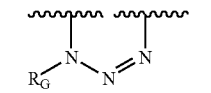

one of $R_5$ and $R_6$ is H or methyl and the other of $R_5$ and $R_6$ is H, $C_{1-6}$alkyl, $C_{2-6}$alkenyl, $C_{2-6}$alkynyl, phenyl, benzyl, or —M-E-G;

M is O, CO, $SO_2$, $NR_J$, (CO)$NR_H$, $NR_H$(CO), $NR_H(SO_2)$, $(SO_2)NR_H$, or $CH_2$;

E is $(CH_2)_{1-4}$ or $(CH_2)_mO(CH_2)_p$ where $1 \leq$ (each of m and p) $\leq 3$ and $2 \leq (m+p) \leq 4$; or E is absent;

G is $R_K$, $OR_I$ or $NR_JR_K$, provided that if p=1, then G is H;

$R_7$ is H, $C_{1-4}$alkyl, $C_{2-4}$alkenyl, $C_{2-4}$alkynyl, $C_{3-6}$cycloalkyl, phenyl, 2-pyridyl, 3-pyridyl, 4-pyridyl, $(CH_2)_{1-2}Ar$, where Ar is phenyl, 2-pyridyl, 3-pyridyl, or 4-pyridyl, $SO_2NR_H(CH_2)_{2-4}NR_JR_K$, (CO)$(CH_2)_{2-4}NR_JR_K$ or (CO)$NR_H(CH_2)_{2-4}NR_JR_K$;

$X_1$ is O, S, $NR_8$, or $CHR_9$; $X_2$ is O, S, or $CHR_9$; and $X_3$ is O or S; where if $X_1$ or $X_2$ is $CHR_9$, said compound may also be a tautomerized indole;

$R_8$ is H, $C_{1-4}$alkyl, phenyl, 2-pyridyl, 3-pyridyl, 4-pyridyl, $(CH_2)_{1-2}Ar$, where Ar is phenyl, 2-pyridyl, 3-pyridyl, 4-pyridyl, $C_{2-4}$alkenyl, $C_{2-4}$alkynyl, $C_{3-6}$cycloalkyl, or $(C_{2-4}alkyl)NR_LR_M$; provided $R_7$ and $R_8$ together have no more than 14 carbon atoms, exclusive of $R_L$, $R_M$, $R_J$ and $R_K$;

$R_G$ is $C_{1-4}$alkyl, phenyl, 2-pyridyl, 3-pyridyl, 4-pyridyl, $C_{3-4}$alkenyl, $C_{3-4}$alkynyl, $C_{3-6}$cycloalkyl, $(CO)OR_P$, $(C_{2-4}alkyl)NR_LR_M$, $(CO)NR_N(CH_2)_{2-4}NR_LR_M$, $(CO)NR_LR_M$, $(CO)(CH_2)_{2-4}$-$NR_LR_M$, or $(CH_2)_{1-2}Ar$, where Ar is phenyl, 2-pyridyl, 3-pyridyl, or 4-pyridyl;

$R_9$ is $C_{1-4}$alkyl, phenyl, 2-pyridyl, 3-pyridyl, 4-pyridyl, $C_{2-4}$alkenyl, $C_{2-4}$alkynyl, $C_{3-6}$cycloalkyl, $(CO)OR_P$, $(C_{2-4}alkyl)NR_LR_M$, $(CO)NR_N(CH_2)_{2-4}NR_LR_M$, $(CO)NR_LR_M$, $(CO)(CH_2)_{2-4}$-$NR_LR_M$, or $(CH_2)_{1-2}Ar'$, where Ar' is phenyl, 2-pyridyl, 3-pyridyl, or 4-pyridyl;

$R_P$ is H, $C_{1-6}$alkyl, phenyl, $C_{3-4}$alkenyl, $C_{3-4}$alkynyl, $C_{3-6}$cycloalkyl, or $(CH_2)_{2-4}NR_LR_M$;

$R_{10}$ is H, methyl, halo, or $NO_2$;

$R_{11}$ is H, methyl, halo, or $NO_2$;

each of $R_C$, $R_D$, $R_E$, $R_F$, $R_J$, $R_J$, $R_K$, $R_L$ and $R_M$ is independently selected from H, $C_{1-4}$alkyl, $C_{3-4}$alkenyl, $C_{3-4}$alkynyl, $C_{3-6}$cycloalkyl, and phenyl; each of $NR_CR_D$, $NR_ER_F$, $NR_JR_K$, and $NR_LR_M$ can also independently be morpholinyl, piperazinyl, pyrrolidinyl, or piperidinyl; and each of $R_H$, $R_N$, and $R_O$ is independently H, methyl, or ethyl;

wherein each hydrocarbon radical or heterocyclic radical above is optionally substituted with between 1 and 3 substituents independently selected from halo, $C_{1-4}$alkyl, $C_{3-6}$cycloalkyl, $C_{3-4}$alkenyl, $C_{3-4}$alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$alkyl, hydroxyl, amino, and $NO_2$;

or a pharmaceutically acceptable salt or $C_{1-7}$ester thereof.

4. A method for treating chronic pain, wherein said chronic pain is associated with arthritis, said method comprising administering to a subject in need of such treatment a composition comprising a MEK inhibitor selected from a compound of the following formula (I):

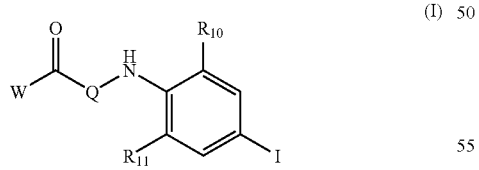
(I)

wherein
W is $OR_1$, $NR_2OR_1$, $NR_AR_B$, $NR_2NR_AR_B$, $O(CH_2)_{2-4}NR_AR_B$, or $NR_2(CH_2)_{2-4}NR_AR_B$;

$R_1$ is H, $C_{1-8}$alkyl, $C_{3-8}$alkenyl, $C_{3-8}$alkynyl, $C_{3-8}$cycloalkyl, phenyl, (phenyl)$C_{1-4}$alkyl, (phenyl)$C_{3-4}$alkenyl, (phenyl)$C_{3-4}$alkynyl, $(C_{3-8}$cycloalkyl)$C_{1-4}$alkyl, $(C_{3-8}$cycloalkyl)$C_{3-4}$alkenyl, $(C_{3-8}$cycloalkyl)$C_{3-4}$alkynyl, $C_{3-8}$heterocyclic radical, ($C_{3-8}$heterocyclic radical)$C_{1-4}$alkyl, ($C_{3-8}$heterocyclic radical)-$C_{3-4}$alkenyl, ($C_{3-8}$heterocyclic radical)$C_{3-4}$alkynyl or $(CH_2)_{2-4}NR_CR_D$;

$R_2$ is H, $C_{1-4}$alkyl, phenyl, $C_{3-6}$cycloalkyl, $C_{3-6}$heterocyclic radical, or $(C_{3-6}$cycloalkyl)methyl;

$R_A$ is H, $C_{1-6}$alkyl, $C_{3-8}$alkenyl, $C_{3-8}$alkynyl, $C_{3-8}$cycloalkyl, phenyl, $(C_{3-8}$cycloalkyl)$C_{1-4}$alkyl, $(C_{3-8}$cycloalkyl)$C_{3-4}$alkenyl, $(C_{3-8}$cycloalkyl)$C_{3-4}$alkynyl, $C_{3-8}$heterocyclic radical, ($C_{3-8}$heterocyclic radical)$C_{1-4}$alkyl, (aminosulfonyl)phenyl, [(aminosulfonyl)phenyl]$C_{1-4}$alkyl, (aminosulfonyl)$C_{1-6}$alkyl, (aminosulfonyl)$C_{3-6}$cycloalkyl, [(aminosulfonyl)$C_{3-6}$cycloalkyl]$C_{1-4}$alkyl, or $(CH_2)_{2-4}NR_CR_D$;

$R_B$ is H, $C_{1-8}$alkyl, $C_{3-8}$alkenyl, $C_{3-8}$alkynyl, $C_{3-8}$cycloalkyl, or phenyl;

Q is one of the following formulae (i)–(iii):

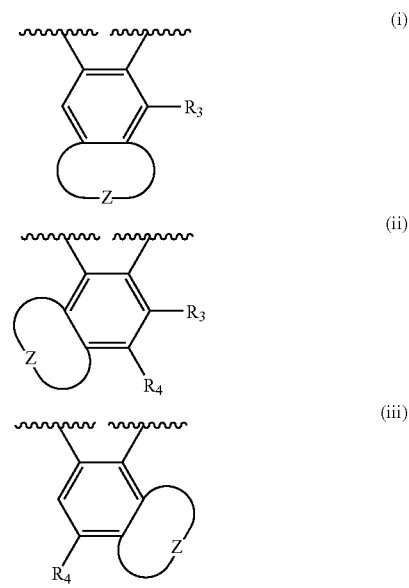

$R_3$ is H or F;

$R_4$ is halo, $NO_2$, $SO_2NR_O(CH_2)_{2-4}NR_ER_F$, $SO_2NR_ER_F$, or (CO)T;

T is $C_{1-8}$alkyl, $C_{3-8}$cycloalkyl, $(NR_ER_F)C_{1-4}$alkyl, $OR_F$, —$NR_O(CH_2)_{2-4}NR_ER_F$, or $NR_ER_F$;

Z is one of the following formula (iv)–(viii):

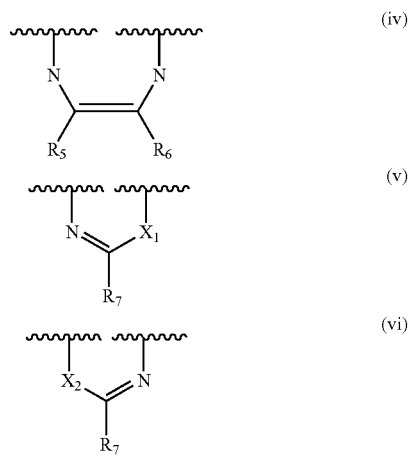

-continued

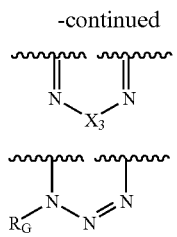

one of $R_5$ and $R_6$ is H or methyl and the other of $R_5$ and $R_6$ is H, $C_{1-6}$alkyl, $C_{2-6}$alkenyl, $C_{2-6}$alkynyl, phenyl, benzyl, or —M-E-G;

M is O, CO, $SO_2$, $NR_J$, (CO)$NR_H$, $NR_H$(CO), $NR_H(SO_2)$, $(SO_2)NR_H$, or $CH_2$;

E is $(CH_2)_{1-4}$ or $(CH_2)_mO(CH_2)_p$ where $1 \leq$ (each of m and p) $\leq 3$ and $2 \leq (m+p) \leq 4$; or E is absent;

G is $R_K$, $OR_J$ or $NR_JR_K$, provided that if p=1, then G is H;

$R_7$ is H, $C_{1-4}$alkyl, $C_{2-4}$alkenyl, $C_{2-4}$alkynyl, $C_{3-6}$cycloalkyl, phenyl, 2-pyridyl, 3-pyridyl, 4-pyridyl, $(CH_2)_{1-2}$Ar, where Ar is phenyl, 2-pyridyl, 3-pyridyl, or 4-pyridyl, $SO_2NR_H(CH_2)_{2-4}NR_JR_K$, (CO)$(CH_2)_{2-4}NR_JR_K$ or (CO)$NR_H(CH_2)_{2-4}NR_JR_K$;

$X_1$ is O, S, $NR_8$, or $CHR_9$; $X_2$ is O, S, or $CHR_9$; and $X_3$ is O or S; where if $X_1$ or $X_2$ is $CHR_9$, said compound may also be a tautomerized indole;

$R_8$ is H, $C_{1-4}$alkyl, phenyl, 2-pyridyl, 3-pyridyl, 4-pyridyl, $(CH_2)_{1-2}$Ar, where Ar is phenyl, 2-pyridyl, 3-pyridyl, or 4-pyridyl, $C_{2-4}$alkenyl, $C_{2-4}$alkynyl, $C_{3-6}$cycloalkyl, or $(C_{2-4}$alkyl)$NR_LR_M$; provided $R_7$ and $R_8$ together have no more than 14 carbon atoms, exclusive of $R_L$, $R_M$, $R_J$ and $R_K$;

$R_G$ is $C_{1-4}$alkyl, phenyl, 2-pyridyl, 3-pyridyl, 4-pyridyl, $C_{3-4}$alkenyl, $C_{3-4}$alkynyl, $C_{3-6}$cycloalkyl, (CO)$OR_P$, $(C_{2-4}$alkyl)$NR_LR_M$, (CO)$NR_N(CH_2)_{2-4}NR_LR_M$, (CO)$NR_LR_M$, (CO)$(CH_2)_{2-4}$-$NR_LR_M$, or $(CH_2)_{1-2}$Ar, where Ar is phenyl, 2-pyridyl, 3-pyridyl, or 4-pyridyl;

$R_9$ is $C_{1-4}$alkyl, phenyl, 2-pyridyl, 3-pyridyl, 4-pyridyl, $C_{2-4}$alkenyl, $C_{2-4}$alkynyl, $C_{3-6}$cycloalkyl, (CO)$OR_P$, $(C_{2-4}$alkyl)$NR_LR_M$, (CO)$NR_N$ $(CH_2)_{2-4}NR_LR_M$, (CO)$NR_LR_M$, (CO)$(CH_2)_{2-4}$-$NR_LR_M$, or $(CH_2)_{1-2}$Ar', where Ar' is phenyl, 2-pyridyl, 3-pyridyl, or 4-pyridyl;

$R_P$ is H, $C_{1-6}$alkyl, phenyl, $C_{3-4}$alkenyl, $C_{3-4}$alkynyl, $C_{3-6}$cycloalkyl, or $(CH_2)_{2-4}NR_LR_M$;

$R_{10}$ is H, methyl, halo, or $NO_2$;

$R_{11}$ is H, methyl, halo, or $NO_2$;

each of $R_C$, $R_D$, $R_E$, $R_F$, $R_I$, $R_J$, $R_K$, $R_L$ and $R_M$ is independently selected from H, $C_{1-4}$alkyl, $C_{3-4}$alkenyl, $C_{3-4}$alkynyl, $C_{3-6}$cycloalkyl, and phenyl; each of $NR_CR_D$, $NR_ER_F$, $NR_JR_K$, and $NR_LR_M$ can also independently be morpholinyl, piperazinyl, pyrrolidinyl, or piperidinyl; and each of $R_H$, $R_N$, and $R_O$ is independently H, methyl, or ethyl;

wherein each hydrocarbon radical or heterocyclic radical above is optionally substituted with between 1 and 3 substituents independently selected from halo, $C_{1-4}$alkyl, $C_{3-6}$cycloalkyl, $C_{3-4}$alkenyl, $C_{3-4}$alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$alkyl, hydroxyl, amino, and $NO_2$;

or a pharmaceutically acceptable salt or $C_{1-7}$ ester thereof.

5. A method for treating chronic pain, wherein said chronic pain is associated with post-operative pain, said method comprising administering to a subject in need of such treatment a composition comprising a MEK inhibitor selected from a compound of the following formula (I):

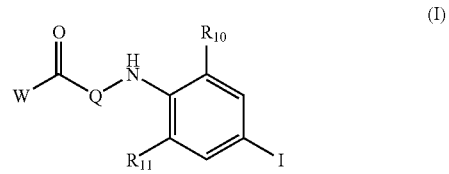

wherein

W is $OR_1$, $NR_2OR_1$, $NR_AR_B$, $NR_2NR_AR_B$, $O(CH_2)_{2-4}$ $NR_AR_B$, or $NR_2(CH_2)_{2-4}NR_AR_B$;

$R_1$ is H, $C_{1-8}$alkyl, $C_{3-8}$alkenyl, $C_{3-8}$alkynyl, $C_{3-8}$cycloalkyl, phenyl, (phenyl)$C_{1-4}$alkyl, (phenyl)$C_{3-4}$alkenyl, (phenyl)$C_{3-4}$alkynyl, $(C_{3-8}$cycloalkyl)$C_{1-4}$alkyl, $(C_{3-8}$cycloalkyl)$C_{3-4}$alkenyl, $(C_{3-8}$cycloalkyl)$C_{3-4}$alkynyl, $C_{3-8}$heterocyclic radical, $(C_{3-8}$heterocyclic radical)$C_{1-4}$alkyl, $(C_{3-8}$heterocyclic radical)-$C_{3-4}$alkenyl, $(C_{3-8}$ heterocyclic radical)$C_{3-4}$alkynyl or $(CH_2)_{2-4}NR_CR_D$;

$R_2$ is H, $C_{1-4}$alkyl, phenyl, $C_{3-6}$cycloalkyl, $C_{3-6}$heterocyclic radical, or $(C_{3-6}$cycloalkyl)methyl;

$R_A$ is H, $C_{1-6}$alkyl, $C_{3-8}$alkenyl, $C_{3-8}$alkynyl, $C_{3-8}$cycloalkyl, phenyl, $(C_{3-8}$cycloalkyl)$C_{1-4}$alkyl, $(C_{3-8}$cycloalkyl)$C_{3-4}$alkenyl, $(C_{3-8}$cycloalkyl)$C_{3-4}$alkynyl, $C_{3-8}$heterocyclic radical, $(C_{3-8}$heterocyclic radical)$C_{1-4}$alkyl, (aminosulfonyl)phenyl, [(aminosulfonyl)phenyl]$C_{1-4}$alkyl, (aminosulfonyl)$C_{1-6}$alkyl, (aminosulfonyl)$C_{3-6}$cycloalkyl, [(aminosulfonyl)$C_{3-6}$cycloalkyl]$C_{1-4}$alkyl, or $(CH_2)_{2-4}NR_CR_D$;

$R_B$ is H, $C_{1-8}$alkyl, $C_{3-8}$alkenyl, $C_{3-8}$alkynyl, $C_{3-8}$cycloalkyl, or phenyl;

Q is one of the following formulae (i)–(iii):

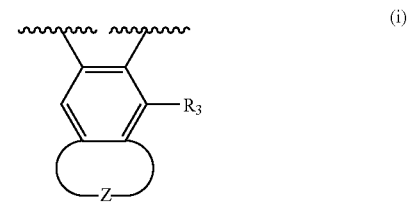

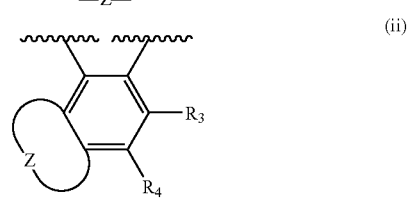

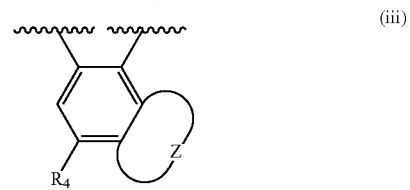

$R_3$ is H or F;

$R_4$ is halo, $NO_2$, $SO_2NR_O(CH_2)_{2-4}NR_ER_F$, $SO_2NR_ER_F$, or (CO)T;

T is $C_{1-8}$alkyl, $C_{3-8}$cycloalkyl, $(NR_ER_F)C_{1-4}$alkyl, $OR_F$, $-NR_O(CH_2)_{2-4}NR_ER_F$, or $NR_ER_F$;

Z is one of the following formula (iv)–(viii):

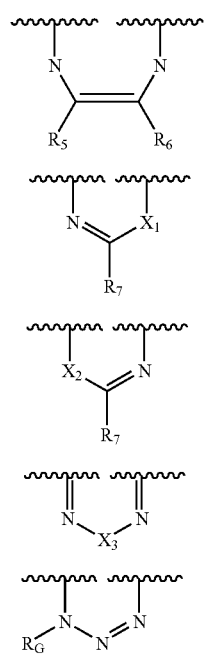

one of $R_5$ and $R_6$ is H or methyl and the other of $R_5$ and $R_6$ is H, $C_{1-6}$alkyl, $C_{2-6}$alkenyl, $C_{2-6}$alkynyl, phenyl, benzyl, or —M-E-G;

M is O, CO, $SO_2$, $NR_J$, $(CO)NR_H$, $NR_H(CO)$, $NR_H(SO_2)$, $(SO_2)NR_H$, or $CH_2$;

E is $(CH_2)_{1-4}$ or $(CH_2)_mO(CH_2)_p$ where $1 \leq$ (each of m and p) $\leq 3$ and $2 \leq (m+p) \leq 4$; or E is absent;

G is $R_K$, $OR_I$ or $NR_JR_K$, provided that if p=1, then G is H;

$R_7$ is H, $C_{1-4}$alkyl, $C_{2-4}$alkenyl, $C_{2-4}$alkynyl, $C_{3-6}$cycloalkyl, phenyl, 2-pyridyl, 3-pyridyl, 4-pyridyl, $(CH_2)_{1-2}$Ar, where Ar is phenyl, 2-pyridyl, 3-pyridyl, or 4-pyridyl,
$SO_2NR_H(CH_2)_{2-4}NR_JR_K$, $(CO)(CH_2)_{2-4}NR_JR_K$ or $(CO)NR_H(CH_2)_{2-4}NR_JR_K$;

$X_1$ is O, S, $NR_8$, or $CHR_9$; $X_2$ is O, S, or $CHR_9$; and $X_3$ is O or S; where if $X_1$ or $X_2$ is $CHR_9$, said compound may also be a tautomerized indole;

$R_8$ is H, $C_{1-4}$alkyl, phenyl, 2-pyridyl, 3-pyridyl, 4-pyridyl, $(CH_2)_{1-2}$Ar, where Ar is phenyl, 2-pyridyl, 3-pyridyl, or 4-pyridyl, $C_{2-4}$alkenyl, $C_{2-4}$alkynyl, $C_{3-6}$cycloalkyl, or $(C_{2-4}$alkyl)$NR_LR_M$; provided $R_7$ and $R_8$ together have no more than 14 carbon atoms, exclusive of $R_L$, $R_M$, $R_J$ and $R_K$;

$R_G$ is $C_{1-4}$alkyl, phenyl, 2-pyridyl, 3-pyridyl, 4-pyridyl, $C_{3-4}$alkenyl, $C_{3-4}$alkynyl, $C_{3-6}$cycloalkyl, $(CO)OR_P$, $(C_{2-4}$alkyl)$NR_LR_M$, $(CO)NR_N(CH_2)_{2-4}NR_LR_M$, $(CO)NR_LR_M$, $(CO)(CH_2)_{2-4}$-$NR_LR_M$, or $(CH_2)_{1-2}$Ar, where Ar is phenyl, 2-pyridyl, 3-pyridyl, or 4-pyridyl;

$R_9$ is $C_{1-4}$alkyl, phenyl, 2-pyridyl, 3-pyridyl, 4-pyridyl, $C_{2-4}$alkenyl, $C_{2-4}$alkynyl,
$C_{3-6}$cycloalkyl, $(CO)OR_P$, $(C_{2-4}$alkyl)$NR_LR_M$, $(CO)NR_N(CH_2)_{2-4}NR_LR_M$, $(CO)NR_LR_M$, $(CO)(CH_2)_{2-4}$-$NR_LR_M$, or $(CH_2)_{1-2}$Ar', where Ar' is phenyl, 2-pyridyl, 3-pyridyl, or 4-pyridyl;

$R_P$ is H, $C_{1-6}$alkyl, phenyl, $C_{3-4}$alkenyl, $C_{3-4}$alkynyl, $C_{3-6}$cycloalkyl, or $(CH_2)_{2-4}NR_LR_M$;

$R_{10}$ is H, methyl, halo, or $NO_2$;

$R_{11}$ is H, methyl, halo, or $NO_2$;

each of $R_C$, $R_D$, $R_E$, $R_F$, $R_I$, $R_J$, $R_K$, $R_L$ and $R_M$ is independently selected from H, $C_{1-4}$alkyl, $C_{3-4}$alkenyl, $C_{3-4}$alkynyl, $C_{3-6}$cycloalkyl, and phenyl; each of $NR_CR_D$, $NR_ER_F$, $NR_JR_K$, and $NR_LR_M$ can also independently be morpholinyl, piperazinyl, pyrrolidinyl, or piperidinyl; and each of $R_H$, $R_N$, and $R_O$ is independently H, methyl, or ethyl;

wherein each hydrocarbon radical or heterocyclic radical above is optionally substituted with between 1 and 3 substituents independently selected from halo, $C_{1-4}$alkyl, $C_{3-6}$cycloalkyl, $C_{3-4}$alkenyl, $C_{3-4}$alkynyl, phenyl, hydroxyl, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$alkyl, hydroxyl, amino, and $NO_2$;

or a pharmaceutically acceptable salt or $C_{1-7}$ ester thereof.

6. A method of claim 4, wherein Q is formula (i).

7. A method of claim 6, wherein $R_3$ is H or fluoro.

8. A method of claim 7, wherein $R_4$ is fluoro, chloro, or bromo.

9. A method of claim 4, wherein $R_{10}$ is hydrogen, methyl, fluoro, or chloro.

10. A method of claim 4, wherein $R_{11}$ is methyl, chloro, fluoro, nitro, or hydrogen.

11. A method of claim 10, wherein $R_{11}$ is H.

12. A method of claim 10, wherein $R_{11}$ is fluoro.

13. A method of claim 9, wherein each of $R_{10}$ and $R_{11}$ is fluoro.

14. A method of claim 4, wherein $R_1$ is H, methyl, ethyl, propyl, isopropyl, isobutyl, benzyl, phenethyl, allyl, $C_{3-5}$alkenyl, $C_{3-6}$cycloalkyl, $(C_{3-5}$cycloalkyl)$C_{1-2}$alkyl, $(C_{3-5}$heterocyclic radical)$C_{1-2}$alkyl, or $(CH_2)_{2-4}NR_CR_D$.

15. A method of claim 14, wherein $R_1$ is H or $(C_{3-4}$cycloalkyl)$C_{1-2}$alkyl.

16. A method of claim 4, wherein $R_2$ is H or methyl.

17. A method of claim 4, wherein $R_A$ has at least one hydroxyl substituent.

18. A compound of claim 4, wherein $R_A$ is H, methyl, ethyl, isobutyl, hydroxyethyl, phenyl, 2-piperidin-1-yl-ethyl, 2,3-dihydroxy-propyl, 3-[4-(2-hydroxyethyl)-piperazin-1-yl]-propyl, 2-pyrrolidin-1-yl-ethyl, or 2-diethylamino-ethyl; and $R_B$ is H; or where $R_B$ is methyl and $R_A$ is phenyl.

19. A method of claim 4, wherein W is $NR_AR_B$ or $NR_2NR_AR_B$.

20. A method of claim 4, wherein W is $NR_2(CH_2)_{2-4}NR_AR_B$ or $O(CH_2)_{2-3}NR_AR_B$.

21. A method of claim 4, wherein W is $NR_2OR_1$.

22. A method of claim 4, wherein W is $OR_1$.

23. A method of claim 4, wherein Z is formula (v).

24. A method of claim 23, wherein $X_1$ is $NR_8$, and $R_7$ is H.

25. A method of claim 4, wherein said MEK inhibitor has a structure selected from: 7-fluoro-6-(4-iodo-2-methyl-phenylamino)-1H-benzoimidazole-5-carboxylic acid.

26. A method of claim 4, wherein said MEK inhibitor has a structure selected from: 7-fluoro-6-(4-iodo-2-methyl-phenylamino)-1H-benzoimidazole-5-carboxylic acid; 7-fluoro-6-(4-iodo-2-methyl-phenylamino)-benzooxazole-5-carboxylic acid; 7-fluoro-6-(4-iodo-2-methyl-phenylamino)-benzothiazole-5-carboxylic acid; 7-fluoro-6-(4-iodo-2-methyl-phenylamino)-benzo[1,2,5]thiadiazole-5-carboxylic acid; 7-fluoro-6-(4-iodo-2-methyl-phenylamino)-benzo[1,2,5]oxadiazole-5-carboxylic acid; 7-fluoro-6-(4-iodo-2-methyl-phenylamino)-2-(2-hydroxyethyl)-1H-benzoimidazole-5-carboxylic acid; 7-fluoro-6-(4-iodo-2-methyl-phenylamino)-2-(2-dimethylamino-ethyl)-1H-benzoimidazole-5-carboxylic acid; 7-fluoro-6-(4-iodo-2-methyl-phenylamino)-1-acetyl-benzoimidazole-5-carboxylic acid; 8-fluoro-7-(4-iodo-2-methyl-phenylamino)-quinoxaline-6-carboxylic acid; and 7-fluoro-6-(4-iodo-2-methyl-phenylamino)-1H-benzotriazole-5-carboxylic acid; and the corresponding hydroxamic acids and cyclopropylmethyl hydroxamates.

27. A method of claim 4, wherein said MEK inhibitor has a structure selected from: 7-fluoro-6-(4-iodo-2-methyl-phenylamino)-1H-benzoimidazole-5-carboxylic acid cyclopropylmethoxy-amide; 7-fluoro-6-(4-iodo-2-methyl-phenylamino)-6,7-dihydro-1H-benzoimidazole-5-carboxylic acid (hydrochloride); 7-fluoro-6-(4-iodo-2-methyl-phenylamino)-1H-benzoimidazole-5-carboxylic acid; 7-fluoro-6-(4-iodo-2-methyl-phenylamino)-3H-benzoimidazole-5-carboxylic acid (2-hydroxy-ethoxy)-amide; 6-(2-chloro-4-iodo-phenylamino)-7-fluoro-1H-benzoimidazole-5-carboxylic acid; and 7-fluoro-6-(4-iodo-2-methyl-phenylamino)-1H-benzoimidazole-5-carboxylic acid pentafluorophenyl ester.

28. The method of claim 4 wherein said MEK inhibitor has a structure selected from: 7-fluoro-6-(4-iodo-2-methyl-phenylamino)-1H-benzoimidazole-5-carboxylic acid cyclopropylmethoxy-amide; and 7-fluoro-6-(4-iodo-2-methyl-phenylamino)-3H-benzoimidazole-5-carboxylic acid (2-hydroxy-ethoxy)-amide.

* * * * *